(12) United States Patent
Hachisu et al.

(10) Patent No.: US 10,301,295 B2
(45) Date of Patent: May 28, 2019

(54) HERBICIDAL COMPOUNDS

(71) Applicant: Syngenta Participations AG, Basel (CH)

(72) Inventors: Shuji Hachisu, Bracknell (GB); Alan Joseph Hennessy, Bracknell (GB); Jeffrey Steven Wailes, Bracknell (GB); Nigel James Willetts, Bracknell (GB); Christopher John Mathews, Bracknell (GB); Janice Black, Bracknell (GB); Suzanna Jane Dale, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 24 days.

(21) Appl. No.: 15/520,302

(22) PCT Filed: Oct. 13, 2015

(86) PCT No.: PCT/EP2015/073703
§ 371 (c)(1),
(2) Date: Apr. 19, 2017

(87) PCT Pub. No.: WO2016/062585
PCT Pub. Date: Apr. 28, 2016

(65) Prior Publication Data
US 2017/0320863 A1    Nov. 9, 2017

(30) Foreign Application Priority Data
Oct. 22, 2014    (GB) .................................. 1418764.5

(51) Int. Cl.
| | |
|---|---|
| *C07D 413/12* | (2006.01) |
| *A01N 35/06* | (2006.01) |
| *C07D 333/34* | (2006.01) |
| *C07D 295/195* | (2006.01) |
| *C07D 263/58* | (2006.01) |
| *C07D 261/18* | (2006.01) |
| *C07D 239/42* | (2006.01) |
| *C07D 231/16* | (2006.01) |

(Continued)

(52) U.S. Cl.
CPC ........... *C07D 413/12* (2013.01); *A01N 35/06* (2013.01); *A01N 37/34* (2013.01); *A01N 37/44* (2013.01); *A01N 37/50* (2013.01); *A01N 41/06* (2013.01); *A01N 41/10* (2013.01); *A01N 43/10* (2013.01); *A01N 43/40* (2013.01); *A01N 43/54* (2013.01); *A01N 43/56* (2013.01); *A01N 43/76* (2013.01); *A01N 43/80* (2013.01); *A01N 43/84* (2013.01); *A01N 47/28* (2013.01); *A01N 47/30* (2013.01); *A01N 47/34* (2013.01); *A01N 47/36* (2013.01); *A01N 47/38* (2013.01); *C07C 225/12* (2013.01); *C07C 225/18* (2013.01); *C07C 251/38* (2013.01); *C07C 255/57* (2013.01); *C07C 255/58* (2013.01); *C07C 275/24* (2013.01); *C07C 275/28* (2013.01);

(Continued)

(58) Field of Classification Search
None
See application file for complete search history.

(56) References Cited

U.S. PATENT DOCUMENTS 4,338,122 A    7/1982    Wheeler

FOREIGN PATENT DOCUMENTS

| WO | 2010000773 A | 1/2010 |
| WO | 2011007146 A1 | 1/2011 |

(Continued)

OTHER PUBLICATIONS

Patani, G. A.; LaVoie, E. J. "Bioisosterism: A rational approach in drug design" Chemical Reviews, 1996, 96(8), 3147-3176 (Year: 1996).*

(Continued)

*Primary Examiner* — Mina Haghighatian
*Assistant Examiner* — Erin E Hirt
(74) *Attorney, Agent, or Firm* — Toni-Junell Herbert; Dinsmore Shohl LLP

(57) ABSTRACT

The present invention relates to a compound of formula (I) wherein: wherein $R^1$, $R^2$, $R^3$, $R^4$, $R^5$, $R^6$, $R^7$, $R^8$, $R^9$, $R^{10}$, $R^{11}$ and G are as defined herein; and wherein the compound of formula (I) is optionally present as an agrochemically acceptable salt thereof. These compounds are thought to be suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

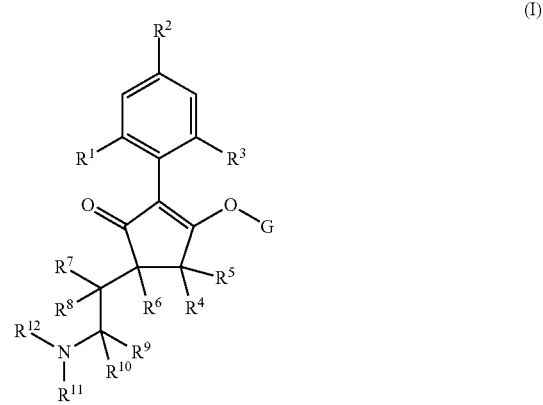

(I)

11 Claims, No Drawings

(51) Int. Cl.

| | |
|---|---|
| *C07D 213/81* | (2006.01) |
| *C07D 213/75* | (2006.01) |
| *C07C 335/26* | (2006.01) |
| *C07C 335/16* | (2006.01) |
| *C07C 311/29* | (2006.01) |
| *C07C 311/16* | (2006.01) |
| *C07C 311/03* | (2006.01) |
| *C07C 275/64* | (2006.01) |
| *C07C 275/28* | (2006.01) |
| *C07C 275/24* | (2006.01) |
| *C07C 255/58* | (2006.01) |
| *C07C 251/38* | (2006.01) |
| *C07C 225/12* | (2006.01) |
| *A01N 47/36* | (2006.01) |
| *A01N 47/34* | (2006.01) |
| *A01N 47/30* | (2006.01) |
| *A01N 47/28* | (2006.01) |
| *A01N 43/84* | (2006.01) |
| *A01N 43/76* | (2006.01) |
| *A01N 43/56* | (2006.01) |
| *A01N 43/40* | (2006.01) |
| *A01N 43/10* | (2006.01) |
| *A01N 41/06* | (2006.01) |
| *A01N 37/50* | (2006.01) |
| *A01N 37/34* | (2006.01) |
| *C07D 401/12* | (2006.01) |
| *C07D 403/12* | (2006.01) |
| *C07D 213/74* | (2006.01) |
| *C07D 213/76* | (2006.01) |
| *C07D 213/78* | (2006.01) |
| *C07D 213/84* | (2006.01) |
| *C07D 233/96* | (2006.01) |
| *C07D 239/28* | (2006.01) |
| *C07D 261/04* | (2006.01) |
| *C07D 261/14* | (2006.01) |
| *C07D 213/61* | (2006.01) |
| *C07C 275/54* | (2006.01) |
| *C07C 225/18* | (2006.01) |
| *C07C 255/57* | (2006.01) |
| *A01N 37/44* | (2006.01) |
| *A01N 41/10* | (2006.01) |
| *A01N 43/54* | (2006.01) |
| *A01N 43/80* | (2006.01) |
| *A01N 47/38* | (2006.01) |

(52) U.S. Cl.
CPC .......... *C07C 275/54* (2013.01); *C07C 275/64* (2013.01); *C07C 311/03* (2013.01); *C07C 311/16* (2013.01); *C07C 311/29* (2013.01); *C07C 335/16* (2013.01); *C07C 335/26* (2013.01); *C07D 213/61* (2013.01); *C07D 213/74* (2013.01); *C07D 213/75* (2013.01); *C07D 213/76* (2013.01); *C07D 213/78* (2013.01); *C07D 213/81* (2013.01); *C07D 213/84* (2013.01); *C07D 231/16* (2013.01); *C07D 233/96* (2013.01); *C07D 239/28* (2013.01); *C07D 239/42* (2013.01); *C07D 261/04* (2013.01); *C07D 261/14* (2013.01); *C07D 261/18* (2013.01); *C07D 263/58* (2013.01); *C07D 295/195* (2013.01); *C07D 333/34* (2013.01); *C07D 401/12* (2013.01); *C07D 403/12* (2013.01); *C07C 2601/08* (2017.05)

(56) References Cited

FOREIGN PATENT DOCUMENTS

| WO | 2011073060 A | 6/2011 |
| WO | 2013079708 A1 | 6/2013 |
| WO | 2014170413 A | 10/2014 |

OTHER PUBLICATIONS

Iowa State University Weed Science; Hartzler, B. "Resolved Isomers explained" http://www.weeds.iastate.edu/mgmt/qtr00-1/isomers.htm (Year: 2000).*
Search Report issued by UKIPO dated Jul. 10, 2015.
Search Report issued by ISA dated Jan. 22, 2016.

* cited by examiner

HERBICIDAL COMPOUNDS

RELATED APPLICATION INFORMATION

This application is a 371 of International Application No. PCT/EP2015/073703, filed 13 Oct. 2015, which claims priority to GB Application No. 1418764.5, filed 22 Oct. 2014, the contents of which are incorporated herein by reference herein.

The present invention relates to novel, herbicidally active cyclopentanedione compounds, specifically 2-(substituted-phenyl)-cyclopentane-1,3-dione compounds, and derivatives thereof (e.g. enol ketone tautomer derivatives thereof), to processes for their preparation, to herbicidal compositions comprising those compounds, and to their use in controlling weeds such as grassy monocotyledonous weeds, especially in crops of useful plants, or in inhibiting undesired plant growth.

U.S. Pat. No. 4,338,122 discloses 2-aryl-1,3-cyclopentanedione compounds exhibiting acaricidal and herbicidal activity. WO 96/01798 discloses 2-aryl-cyclopentane-1,3-dione derivatives and their use as pesticides and herbicides. WO 96/03366 discloses fused 2-(2,4,6-trimethylphenyl)cyclopentane-1,3-dione derivatives and their use as pesticides and herbicides.

WO 99/43649A1 discloses inter alia (4-aryl-phenyl)-substituted or (4-heteroaryl-phenyl)-substituted cyclic keto-enols, including several types of cyclic diones and derivatives thereof. WO 99/48869 A1 discloses inter alia (3-aryl-phenyl)-substituted or (3-heteroaryl-phenyl)-substituted cyclic keto-enols, including several types of cyclic diones and derivatives thereof.

WO01/17972A2 discloses (4-methyl-phenyl)-substituted (such as 4-methyl-2,6-diethyl-phenyl-substituted) heterocycles (e.g. heterocyclic diones) or cyclopentane-1,3-dione derivatives, suitable for use as herbicides. WO 01/74770 discloses $C_2$-phenyl-substituted cyclic ketoenols and their use as pesticides and herbicides.

WO 03/013249 A1 discloses selective herbicidal compositions comprising (a) a (substituted-phenyl)-substituted cyclic ketoenol and (b) a compound which improves crop plant compatibility, in particular cloquintocet-mexyl or mefenpyr-diethyl. In WO 03/013249 A1, the cyclic ketoenol (whose tautomer is a cyclic dione) can for example be a 2-(substituted-phenyl)-cyclopentane-1,3-dione, or a derivative (e.g. ester or carbonate derivative) thereof.

WO 2007/068427 A2 discloses a composition comprising (a) a (substituted-phenyl)-substitutedcyclic ketoenol as a herbicide, and (b) an ammonium and/or phosphonium salt to boost activity. In WO 2007/068427 A2, the cyclic ketoenol (whose tautomer is a cyclic dione) can for example be a 2-(substituted-phenyl)-cyclopentane-1,3-dione or a derivative (e.g. ester or carbonate derivative) thereof.

WO 2009/019005A2 discloses fused bicyclic and oxygen-bridged cyclopentanedione derivatives, specifically 10-oxatricyclo-[5.2.1.0$^{2,6}$]decane-3,5-diones and derivatives, which are substituted by substituted-phenyl and which have herbicidal activity.

WO 2010/000773 A1 discloses 5-(heterocyclylalkyl)-3-hydroxy-2-phenyl-cyclopent-2-enones and certain derivatives thereof as herbicides.

WO 2010/069834 A1 discloses cyclopentane-1,3-diones having both heteroarylmethyl- and 2-(substituted-phenyl)-substituents on the cyclopentane ring, and derivatives thereof containing latentiating groups; these compounds are disclosed as having herbicidal properties.

WO 2011/007146A1 discloses certain 2-(substituted-phenyl)-cyclopentane-1,3-dione derivatives having herbicidal and/or plant-growth-inhibiting properties, in which at the 4-position of the cyclopentane-1,3-dione there is a substituent A-CHR$^4$— in which A is unsubstituted or substituted $C_3$-$C_7$cycloalkyl or A is optionally substituted phenyl.

Other cyclopentane-1,3-dione compounds substituted by substituted-phenyl and having herbicidal activity are described in WO 2010/089210 A1 and WO 2010/102848 A1.

WO 2010/102758 A2 discloses (haloalkylmethoxy-)-phenyl-substituted cyclic keto-enols as pest control agents and/or as herbicides.

WO 2013/079672 A1 discloses that certain substituted spiroheterocyclic pyrrolidine dione compounds, having an alkynyl-phenyl-headgroup, have herbicidal properties.

WO 2013/079708 A1 discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl and at the 2-position by (specifically) either methyl or chlorine, and derivatives of the enol ketone tautomer of such cyclopentanediones, which have herbicidal activity and/or plant-growth-inhibiting properties, especially in the control of grassy monocotyledonous weeds and/or when used post-emergence.

2-(Substituted-phenyl)-cyclopentane-1,3-dione compounds, and derivatives of the enol ketone tautomer of such cyclopentane-1,3-diones, which have an alkynyl-methyl- or similar substituent on the cyclopentane-1,3-dione, and which have herbicidal activity and/or plant-growth-inhibiting properties, especially in the control of grassy monocotyledonous weeds and/or when used post-emergence, have now been found, which are encompassed by the present invention.

Thus, according to the present invention there is provided a compound of formula (I):

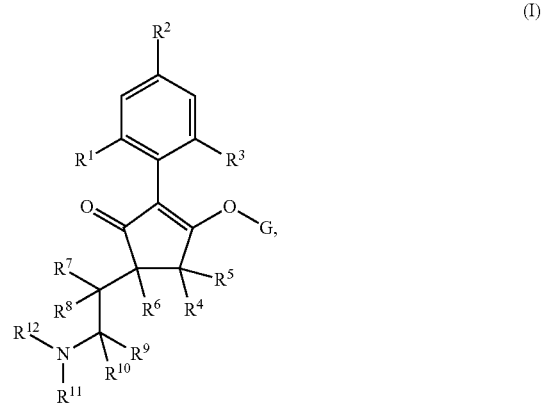

or an agrochemically acceptable salt thereof wherein:

$R^1$ is selected from the group consisting of methyl, ethyl, n-propyl, cyclopropyl, trifluoromethyl, vinyl, ethynyl, fluorine, chlorine, bromine, methoxy, ethoxy and fluoromethoxy;

$R^2$ is selected from the group consisting of hydrogen, methyl, ethyl, n-propyl, isopropyl, cyclopropyl, fluoromethyl, fluoroethyl, vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen, methoxy, prop-2-ynyloxy, and ($C_1$-$C_2$fluoroalkyl)-methoxy-; or $R^2$ is phenyl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro; or $R^2$ is monocyclic heteroaryl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro; and $R^3$ is selected from the group consisting of hydrogen, methyl, ethyl, n-propyl, cyclopropyl, trifluoromethyl, vinyl, ethynyl, fluorine, chlorine, bromine, methoxy, ethoxy, n-propoxy, isopropoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-;

$R^4$, $R^5$ and $R^6$ are independently of each other, selected from the group consisting of hydrogen, $C_1$-$C_5$alkyl, $C_2$-$C_3$alkenyl, $C_2$-$C_3$alkynyl, $C_1$-$C_2$fluoroalkyl and $C_1$-$C_2$alkoxy$C_1$-$C_2$alkyl;

$R^7$ and $R^8$ are independently of each other, selected from the group consisting of hydrogen, fluorine and $C_1$-$C_3$alkyl;

$R^9$ and $R^{19}$ are independently of each other, selected from the group consisting of hydrogen, fluorine and $C_1$-$C_3$alkyl;

$R^{11}$ is selected from the group consisting of, —(C=O)-5,5-dimethyl-4H-isoxazol-2-yl, —(C=X)$NR^{13}R^{14}$, —$SO_2$—$R^{18}$, —(C=O)—C($C_1$-$C_3$alkyl))=N—O—$R^{19}$, —(C=O)—C(CN)=N—O—$R^{19}$ and —$R^{15}$, wherein X=S or O;

R12 is selected from the group consisting of hydrogen, $C_1$-$C_6$alkyl, $C_1$-$C_6$alkoxy and hydroxy;

$R^{13}$ is selected from the group consisting of hydrogen, $C_1$-$C_6$alkyl, $C_3$-$C_8$cycloalkyl, $C_1$-$C_6$haloalkyl, $C_2$-$C_6$alkenyl, $C_2$-$C_6$alkynyl, $C_1$-$C_6$alkoxy$C_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxy$C_1$-$C_6$-alkyl-, $C_1$-$C_6$alkoxy-$C_2$-$C_3$-alkoxy-$C_2$-$C_3$-alkyl-, $C_1$-$C_6$alkylcarbonyl- and $C_1$-$C_6$alkylcarbonyl$C_1$-$C_6$-alkyl-;

$R^{14}$ is selected from the group consisting of hydrogen, $C_1$-$C_6$alkyl, $C_3$-$C_8$cycloalkyl, hydroxyl, $C_1$-$C_6$alkoxy-, $C_1$-$C_6$haloalkyl, $C_2$-$C_6$alkenyl, $C_2$-$C_6$alkynyl, $C_1$-$C_6$alkoxy$C_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxy$C_1$-$C_6$-alkyl-, $C_1$-$C_6$alkoxy-$C_2$-$C_3$-alkoxy-$C_2$-$C_3$-alkyl-, $C_1$-$C_6$alkylcarbonyl-, $C_1$-$C_6$alkylcarbonyl$C_1$-$C_6$-alkyl-; or $R^{14}$ is —(CR'R")$_n$—$X^1$—$R^{15}$ wherein R' and R" are independently selected from the group consisting of is hydrogen, fluorine and $C_1$-$C_2$alkyl, and $X^1$ is a bond or —(C=O)—; or $R^{13}$ and $R^{14}$ together form a morpholinyl group; and $R^{15}$ is a three- to ten-membered mono- or bicyclic ring system, which may be aromatic, saturated or partially saturated and can, optionally, contain from 1 to 4 heteroatoms each independently selected from the group consisting of nitrogen, oxygen and sulphur the ring system being optionally substituted by one or more $R^{16}$ substituents;

$R^{16}$ is selected from the group consisting of halogen, $C_1$-$C_6$alkyl, $C_1$-$C_6$haloalkyl, $C_1$-$C_6$haloalkoxy, $C_1$-$C_6$alkoxy-, nitro, —(CO)$OR^{17}$, cyano, phenyl and pyridyl;

$R^{17}$ is H or $C_1$-$C_6$ alkyl;

$R^{18}$ is selected from the group consisting of hydrogen, $C_1$-$C_6$alkyl and phenyl optionally substituted by one or more $R^{16}$;

$R^{19}$ is selected from the group consisting of hydrogen, $C_1$-$C_6$ alkyl and —$(CH_2)_nR^{15}$;

n=0, 1, 2;

and wherein:

G is hydrogen; an agriculturally acceptable metal, or an agriculturally acceptable sulfonium or ammonium group; or G is —C($X^a$)—$R^a$, —C($X^b$)—$X^c$—$R^b$, —C($X^d$)—N($R^c$)—$R^d$, —$SO_2$—$R^e$, —P($X^e$)($R^f$)—$R^g$, —$CH_2$—$X^f$—$R^h$, or —CH(Me)-$X^f$—$R^h$; or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkyl-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;

wherein $X^a$, $X^b$, $X^c$, $X^d$, $X^e$ and $X^f$ are independently of each other oxygen or sulfur; and wherein $R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_6$alkylamino($C_1$-$C_6$)alkyl, $C_2$-$C_8$dialkylamino($C_1$-$C_6$)alkyl, $C_3$-$C_7$cycloalkyl($C_1$-$C_6$)alkyl, $C_1$-$C_6$alkoxy($C_1$-$C_6$)alkyl, $C_3$-$C_6$alkenyloxy($C_1$-$C_6$)alkyl, $C_3$-$C_6$alkynyloxy($C_1$-$C_6$)alkyl, $C_1$-$C_6$alkylthio($C_1$-$C_6$)alkyl, $C_1$-$C_6$alkylsulfinyl($C_1$-$C_6$)alkyl, $C_1$-$C_6$alkylsulfonyl($C_1$-$C_6$)alkyl, $C_2$-$C_8$alkylideneaminoxy($C_1$-$C_6$)alkyl, $C_1$-$C_6$alkylcarbonyl($C_1$-$C_6$)alkyl, $C_1$-$C_6$alkoxycarbonyl($C_1$-$C_6$)alkyl, aminocarbonyl($C_1$-$C_6$)alkyl, $C_1$-$C_6$alkylaminocarbonyl($C_1$-$C_6$)alkyl, $C_2$-$C_8$dialkylaminocarbonyl($C_1$-$C_6$)alkyl, $C_1$-$C_6$alkylcarbonylamino($C_1$-$C_6$)alkyl, N—($C_1$-$C_6$)alkyl-carbonyl-N—($C_1$-$C_6$)alkylamino($C_1$-$C_6$)alkyl, $C_3$-$C_6$trialkylsilyl($C_1$-$C_6$)alkyl, phenyl($C_1$-$C_6$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_6$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_6$alkylamino($C_1$-$C_6$)alkyl, $C_2$-$C_8$dialkylamino($C_1$-$C_6$)alkyl, $C_3$-$C_7$cycloalkyl($C_1$-$C_6$) alkyl, $C_1$-$C_6$alkoxy($C_1$-$C_6$)alkyl, $C_3$-$C_6$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy; or $R^c$ and $R^d$, together with the nitrogen to which they are bonded, form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C (O)—; $C_1$-$C_6$alkoxy-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine. More preferably, in various aspects and/or embodiments of the invention, halogen is fluorine or chlorine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF—$, $CF_3CH_2—$, $CHF_2CH_2—$, $CH_2FCH_2—$, $CHF_2CF_2—$ or $(CH_3)_2CF—$. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO—$, $CF_3CH_2O—$, $CHF_2CH_2O—$ or $CH_2FCH_2O—$.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a$$R_b$$R_c$$R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e$$R_f$$R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups (i.e. leaving or removeable groups) within G (for example, without limitation, the latentiating groups where G is —C($X^a$)—$R^a$ or —C($X^b$)—$X^c$—$R^b$, et al.) are generally selected to allow their removal, typically by one or a combination of biochemical, chemical or physical processes, to afford the corresponding compound of formula (I) where G is H, before, during or following (preferably during or following) application of the compound of formula (I) to the treated area (e.g. field) or to plants. Examples of these processes include enzymatic cleavage or other in/on-plant cleavage (e.g. cleavage of ester and/or carbonate moieties), chemical hydrolysis, and/or photolysis. Some compounds bearing such groups G occasionally offer certain advantages or different technical properties, such as improved and/or more consistent and/or different penetration of the cuticula of the plants treated, increased and/or different tolerance of certain crops, improved and/or different compatibility or stability in formulated mixtures containing other herbicides, herbicide safeners, plant growth regulators, fungicides or insecticides, or reduced and/or different leaching properties in soils.

The preferred (including more preferred, most preferred, et al.), suitable and/or particular values of the substituents in, or other features of, the compound of formula (I), in particular (and without limitation): G, $R^1$, $R^2$, $R^{2A}$, $R^{2B}$, $R^3$, $R^{3A}$, $R^{3B}$, $R^4$, $R^{4A}$, $R^{4B}$, $R^{4C}$, $R^5$, $R^6$, $R^7$, $R^8$, $R^9$, $R^{10}$, $R^{11}$, $R^{11B}$, $R^{12}$, $R^{12A}$, $R^{12AA}$, $R^{12B}$, $R^{13}$, $R^{13A}$, $R^{13AA}$, $R^{13B}$, $R^{14}$, $R^{14A}$, $R^{14B}$, $R^{15}$, $R^{16}$, $R^a$, $R^b$, $R^c$, $R^d$, $R^e$, $R^f$, $R^g$, $R^h$, $X^a$, $X^b$, $X^c$, $X^d$, $X^e$, and/or $X^f$; are set out below (and/or generally herein), and can be either taken alone or taken together with one or more of any other preferred (including more preferred, most preferred, et al.), suitable and/or particular values of the substituents in, or other features of, the compound of formula (I), in any and all possible combination(s) thereof.

Preferably, e.g. in all aspects and/or embodiments of the invention, G is hydrogen; an agriculturally acceptable metal (e.g. an agriculturally acceptable alkali metal or alkaline earth metal), or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined herein. More preferably, G is hydrogen, or an agriculturally acceptable alkali metal (e.g. lithium, sodium or potassium) or an agriculturally acceptable alkaline earth metal (e.g. calcium or magnesium), or —C($X^a$)—$R^a$ or —C($X^b$)—$X^c$—$R^b$.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, $X^a$, $X^b$, $X^c$, $X^d$, $X^e$ and/or $X^f$ are oxygen; and/or $X^c$ is sulfur. More preferably, $X^a$, $X^b$, $X^c$, $X^d$, $X^e$ and $X^f$ are oxygen; and/or $X^c$ is sulfur.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

More preferably, $R^a$ is $C_1$-$C_{10}$alkyl (e.g. $C_1$-$C_6$alkyl), $C_2$-$C_5$alkenyl (e.g. $C_2$-$C_4$alkenyl), $C_2$-$C_6$alkynyl (e.g. $C_2$-$C_4$alkynyl), $C_3$-$C_6$cycloalkyl, or $C_1$-$C_4$alkoxy$C_1$-$C_4$alkyl.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

More preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, or $C_1$-$C_4$alkoxy$C_1$-$C_4$alkyl.

Preferably, $X^a$, $X^b$ and $X^c$ are oxygen (and/or $X^c$ is sulfur); and $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; and $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

In a particularly preferable embodiment, G is hydrogen, —$C(X^a)$—$R^a$ or —$C(X^b)$—$X^c$—$R^b$.

In another preferable embodiment, G is hydrogen, or an agriculturally acceptable alkali metal or alkaline earth metal, or an agriculturally acceptable sulfonium or ammonium group. In a particular embodiment, G is hydrogen, or an agriculturally acceptable alkali metal (e.g. lithium, sodium or potassium) or an agriculturally acceptable alkaline earth metal (e.g. calcium or magnesium).

Most preferably, G is hydrogen.

In a preferred embodiment of the present invention, $R^1$ is methyl or chlorine, most preferably methyl.

In another preferred embodiment, $R^2$ is selected from the group consisting of methyl, prop-1-ynyl and an optionally substituted monocyclic heteroaryl selected from the group consisting of $R^{2a}$ and $R^{2b}$:

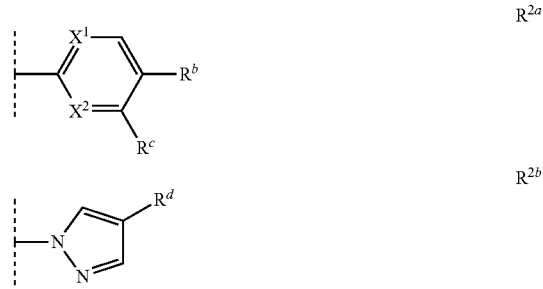

in which:

$X^1$ is N or CH;

$X^2$ is N or $CR^a$;

$R^a$ is selected from the group consisting of hydrogen, fluorine, chlorine and $C_1$fluoroalkyl (preferably trifluoromethyl); more preferably hydrogen or fluorine.

$R^b$ is selected from the group consisting of hydrogen, fluorine, chlorine and $C_1$fluoroalkyl (preferably trifluoromethyl); and $R^c$ is selected from the group consisting of hydrogen, fluorine, chlorine, bromine, methyl, $C_1$fluoroalkyl (preferably trifluoromethyl) and cyano;

$R^d$ is selected from the group consisting of hydrogen, fluorine, chlorine, bromine, methyl, $C_1$fluoroalkyl (preferably trifluoromethyl) and cyano. In a more preferred embodiment, $R^d$ is chlorine.

In a preferred embodiment of the present invention, $R^2$ is methyl. In another preferred embodiment of the present invention, $R^2$ is prop-1-ynyl. In another preferred embodiment of the present invention, $R^2$ is $R^{2b}$ wherein $R^c$ is chlorine.

In another preferred embodiment of the present invention $R^3$ in methyl.

Particularly preferred embodiments of the present invention are compounds of Formula (I) wherein:

(i) $R^1$ is methyl, $R^2$ is prop-1-ynyl and $R^3$ is methyl.

(ii) $R^1$ is methyl, $R^2$ is $R^{2a}$ (wherein $R^a$ is fluorine and $R^b$ is hydrogen) and $R^3$ is methyl.

(iii) $R^1$ is methyl, $R^2$ is $R^{2b}$ (wherein $R^c$ is chlorine) and $R^3$ is methyl.

(iv) $R^1$ is methyl, $R^2$ is methyl and $R^3$ is methyl.

In another preferred embodiment of the present invention, $R^5$, $R^6$, $R^7$, $R^8$, $R^9$ and $R^{10}$ are hydrogen.

In a preferred embodiment, $R^{12}$ is hydrogen or methyl, preferably hydrogen.

In another embodiment of the present invention, $R^{11}$ is —(C=O)-5,5-dimethyl-4H-isoxazol-2-yl.

In another embodiment of the present invention, $R^{11}$ is —(C=O)NR$^{13}$R$^{14}$, wherein $R^{13}$ is selected from the group consisting of hydrogen, $C_1$-$C_6$alkyl, $C_3$-$C_8$cycloalkyl, hydroxyl, $C_1$-$C_6$alkoxy-, $C_1$-$C_6$haloalkyl, $C_2$-$C_6$alkenyl, $C_2$-$C_6$alkynyl, $C_1$-$C_6$alkoxyC$_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxyC$_1$-$C_6$-alkyl-, $C_1$-$C_6$alkoxy-$C_2$-$C_3$-alkoxy-$C_2$-$C_3$-alkyl-, $C_1$-$C_6$alkylcarbonyl- and $C_1$-$C_6$alkylcarbonylC$_1$-$C_6$-alkyl-. More preferably, $R^{13}$ is selected from the group consisting of hydrogen, $C_1$-$C_6$alkyl (preferably methyl or tert-butyl), methoxy and hydroxyl. Even more preferably hydrogen.

In one embodiment of the invention, $R^{14}$ is selected from the group consisting of hydrogen, $C_1$-$C_6$alkyl (preferably methyl), hydroxyl and $C_1$-$C_6$alkoxy- (preferably methoxy-).

In another embodiment of the present invention, $R^{14}$ is —(CH$_2$)$_n$—$R^{15}$ wherein n is 0 (in which case $R^{11}$ is —$R^{15}$) or 1.

In another embodiment of the present invention, $R^{14}$ is —(CH$_2$)$_n$—(C=O)—$R^{15}$ wherein n is 0 or 1.

In each of the embodiments above $R^{15}$ is a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more $R^{16}$ substituents.

$R^{16}$ is selected from the group consisting of halogen, $C_1$-$C_6$alkyl, $C_1$-$C_6$haloalkyl, $C_1$-$C_6$haloalkoxy, $C_1$-$C_6$alkoxy-, nitro, —(CO)OR$^{17}$, cyano, phenyl and pyridyl;

$R^{17}$ is H or $C_1$-$C_6$ alkyl.

In a preferred embodiment, $R^{15}$ is selected from the group consisting of $R^{15a}$, $R^{15b}$, $R^{15c}$, $R^{15d}$, $R^{15e}$ and $R^{15f}$:

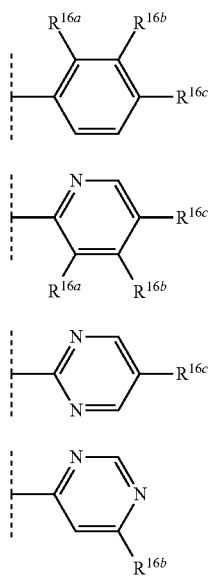

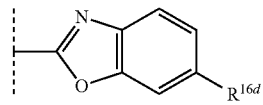

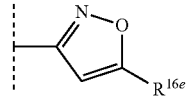

wherein
$R^{16a}$ is selected from the group consisting of hydrogen, $C_1$-$C_4$alkyl, $C_1$-$C_4$haloalkyl (in particular CF$_3$), halogen, $C_1$-$C_4$alkoxy, cyano and nitro;
$R^{16b}$ is selected from the group consisting of hydrogen, $C_1$-$C_4$alkyl, $C_1$-$C_4$haloalkyl (e.g fluoromethyl, trifluoromethyl), halogen, $C_1$-$C_4$alkoxy, nitro and phenyl;
$R^{16c}$ is selected from the group consisting of hydrogen, $C_1$-$C_4$alkyl, halogen (in particular bromine, chlorine, fluorine), $C_1$-$C_4$alkoxy, $C_1$-$C_4$haloalkyl and $C_1$-$C_4$haloalkoxy-;
$R^{16d}$ is hydrogen or halogen (in particular chlorine); and
$R^{16e}$ is hydrogen or $C_1$-$C_6$alkyl (in particular tert-butyl).

In a preferred embodiment, $R^{15}$ is $R^{15b}$ wherein $R^{16a}$, $R^{16b}$ and $R^{16c}$ are hydrogen.

In another embodiment of the present invention, $R^{11}$ is —(C=O)NR$^{13}$R$^{14}$, wherein $R^{13}$ and $R^{14}$ together form a morpholinyl group.

In another embodiment of the present invention, $R^{11}$ is —SO$_2$—$R^{18}$ wherein, $R^{18}$ is selected from the group consisting of hydrogen, $C_1$-$C_6$ alkyl and phenyl wherein the phenyl is optionally substituted by one or more $R^{16}$;

In another embodiment of the present invention, $R^{11}$ is —(C=O)—C(CH$_3$)=N—O—$R^{19}$ or —(C=O)—C(CN)=N—O—$R^{19}$, wherein $R^{19}$ is selected from the group consisting of hydrogen, $C_1$-$C_6$ alkyl and —(CH$_2$)$_n$R$^{15}$;

In another embodiment of the present invention, the compound of Formula (I) is a compound of formula (Ia):

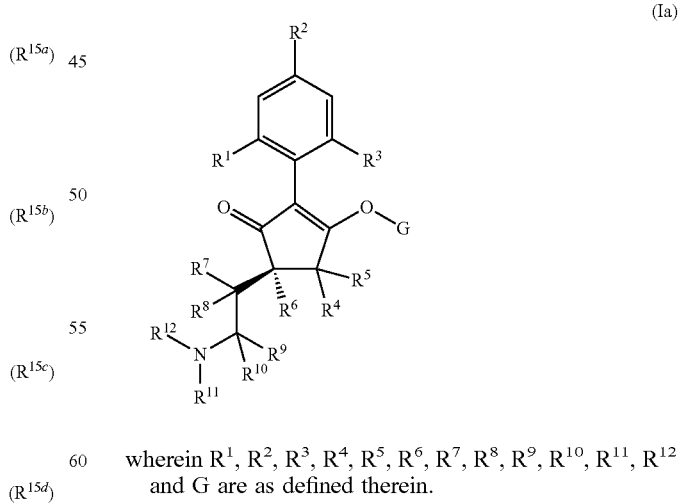

wherein $R^1$, $R^2$, $R^3$, $R^4$, $R^5$, $R^6$, $R^7$, $R^8$, $R^9$, $R^{10}$, $R^{11}$, $R^{12}$ and G are as defined therein.

Preferably, 40% or more (in particular 45% or more) by molarity of the compound of formula (Ia) has the indicated stereochemistry at the ring-carbon atom bonded to $R^6$ and —CR$^7$R$^8$C(R$^9$R$^{10}$)NR$^{11}$R$^{12}$. For example, this broadest definition of formula (Ia) includes compounds which are substantially racemic at the ring-carbon atom bonded to $R^6$ and —CR$^7$R$^8$C(R$^9$R$^{10}$)NR$^{11}$R$^{12}$, and also includes compounds enriched with isomer(s) having the stereochemistry indicated at the ring-carbon atom bonded to R$^6$ and —CR$^7$R$^8$C(R$^9$R$^{10}$)NR$^{11}$R$^{12}$.

More preferably, more than 50% (still more preferably more than 70% or more than 80%, most preferably more than 90% or more than 95%) by molarity of the compound of formula (Ia) has the indicated stereochemistry at the ring-carbon atom bonded to R$^6$ and —CR$^7$R$^8$C(R$^9$R$^{10}$)NR$^{11}$R$^{12}$. This more preferred definition of formula (Ia) includes compounds enriched with isomer(s) having the stereochemistry indicated at the ring-carbon atom bonded to R$^6$ and —CR$^7$R$^8$C(R$^9$R$^{10}$)NR$^{11}$R$^{12}$.

Depending on the nature of the substituents G, R$^1$, R$^2$, R$^3$, R$^4$, R$^5$, R$^6$, R$^7$, R$^8$, R$^9$, and R$^{10}$, compounds of formula (I) may exist in different isomeric or tautomeric forms.

For example, when G is hydrogen, compounds of formula (I) may exist in different tautomeric forms. This invention covers all such isomers and/or tautomers and/or mixtures thereof in all proportions. These isomers and/or tautomers are within the scope of the claimed compounds of formula (I).

Processes for Preparation of Compounds, e.g. Compounds of Formula (I)

Processes for preparation of compounds, e.g. a compound of formula (I) (which optionally can be an agrochemically acceptable salt thereof), are now described, and form further aspects of the present invention.

A compound of formula I, wherein G is:
—C(X$^a$)—R$^a$, —C(X$^b$)—X$^c$—R$^b$, —C(X$^d$)—N(R$^c$)—R$^d$, —SO$_2$—R$^e$, —P(X$^e$)(R$^f$)—R$^g$, —CH$_2$—X$^f$—R$^h$, —CH(Me)-X$^f$—R$^h$; or phenyl-CH$_2$— or phenyl-CH(C$_1$-C$_2$alkyl)- (in each of which the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or heteroaryl-CH$_2$— or heteroaryl-CH(C$_1$-C$_2$alkyl)- (in each of which the heteroaryl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or phenyl-C(O)—CH$_2$— (wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkyl-C(O)—CH$_2$—, C$_1$-C$_6$alkoxy-C(O)—CH=CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;

may be prepared by treating a compound of formula (A), which is a compound of formula I wherein G is H, (a) with a reagent G-Z, wherein G-Z is an alkylating agent (wherein G is an organic group according to G within the compound of formula (I) and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—CH$_2$—X$^f$—R$^h$ wherein X$^f$ is oxygen, a chloromethyl alkyl sulfide Cl—CH$_2$—X$^f$—R$^h$ wherein X$^f$ is sulphur, a suitable optionally substituted benzyl halide (e.g. chloride) such as Cl—CH$_2$-[optionally substituted phenyl], [optionally substituted phenyl]-C(O)—CH$_2$-[halogen e.g. Cl], C$_1$-C$_6$alkoxy-C(O)—CH$_2$-[halogen e.g. Cl], C$_1$-C$_6$alkyl-C(O)—CH$_2$-[halogen e.g. Cl], C$_1$-C$_6$alkoxy-C(O)—CH=CH-[halogen e.g. Cl], a suitable alkenyl or alkynyl halide (e.g. chloride) such as C$_2$-C$_7$alken-1-yl-CH$_2$-[halogen e.g. Cl] or C$_2$-C$_7$alkyn-1-yl-CH$_2$-[halogen e.g. Cl], or another organic halide suitable for preparing a (non-carbonyl, non-thiocarbonyl carbon)-linked G group; or (b) [e.g. to prepare carbonyl-carbon-linked or thiocarbonyl-carbon-linked G groups] with an acylating agent such as a carboxylic acid, HO—C(X$^a$)R$^a$, wherein X$^a$ is oxygen, an acid chloride, Cl—C(X$^a$)R$^a$, wherein X$^a$ is oxygen, or an acid anhydride, [R$^a$C(X$^a$)]$_2$O, wherein X$^a$ is oxygen, or an isocyanate, R$^c$N=C=O, or a carbamoyl chloride, Cl—C(X$^d$)—N(R$^c$)—R$^d$ (wherein X$^d$ is oxygen and with the proviso that neither R$^c$ or R$^d$ is hydrogen), or a thiocarbamoyl chloride Cl—(X$^d$)—N(R$^c$)—R$^d$ (wherein X$^d$ is sulfur and with the proviso that neither R$^c$ or R$^d$ is hydrogen), or a chloroformate, Cl—C(X$^b$)—X$^c$—R$^b$ (wherein X$^b$ and X$^c$ are oxygen), or a chlorothioformate Cl—C(X$^b$)—X$^c$—R$^b$ (wherein X$^b$ is oxygen and X$^c$ is sulfur), or a chlorodithioformate Cl—C(X$^b$)—X$^c$—R$^b$ (wherein X$^b$ and X$^c$ are sulfur), or an isothiocyanate, R$^c$N=C=S; or (c) by sequential treatment with carbon disulfide and an alkylating agent; or (d) with a phosphorylating agent such as a phosphoryl chloride, Cl—P(X$^e$)(R$^f$)—R$^g$; or (e) with a sulfonylating agent such as a sulfonyl chloride Cl—SO$_2$—R$^e$, preferably in the presence of at least one equivalent of base.

Where substituents R$^4$ and R$^5$ are not equal to substituents R$^6$ and —CR$^7$R$^8$—CR$^9$R$^{10}$—NR$^{11}$R$^{12}$, the above-described reactions may produce, in addition to a compound of formula (I), a second compound of formula (IA) (see below).

The present invention covers both a compound of formula (I) and a compound of formula (IA), either (I) alone or (IA) alone or as a mixture of compounds (I) and (IA) in any ratio.

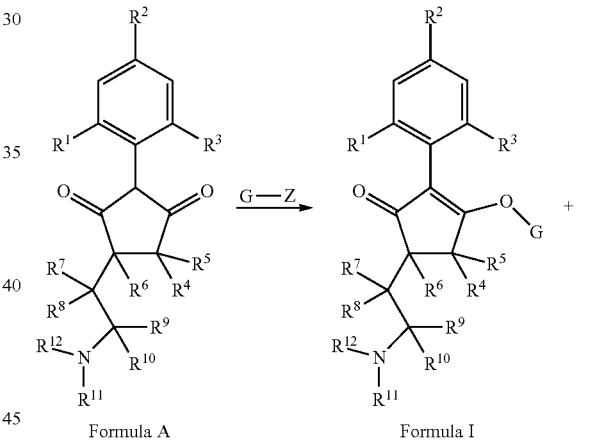

Formula A                    Formula I

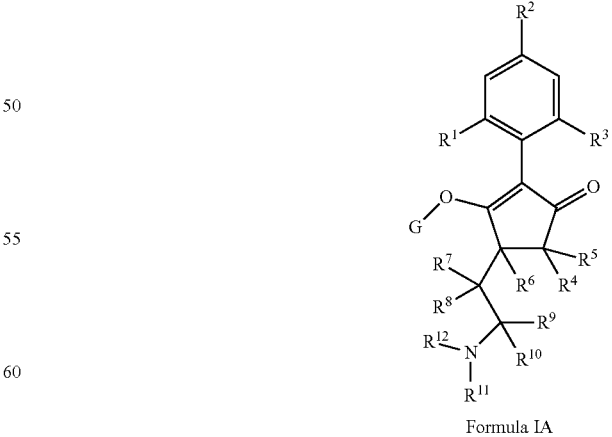

Formula IA

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, or sodium hydride, and suitable organic bases include trialkylamines, such as trimethylamine or triethylamine, pyridines or other amine bases such as 1,4-diazobicyclo[2.2.2]-octane or 1,8-diazabicyclo[5.4.0]undec-7-ene. Preferred bases include triethylamine and pyridine. Suitable solvents for this reaction are selected to be compatible with the reagents and include ethers such as tetrahydrofuran or 1,2-dimethoxyethane or halogenated solvents such as dichloromethane or chloroform. Certain bases, such as pyridine or triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide or N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected e.g. using a phosphoryl halide or thiophosphoryl halide and a base e.g. by procedures analogous to those described by L. Hodakowski, U.S. Pat. No. 4,409,153.

Sulfonylation of a compound of formula (A) may be achieved e.g. using an alkyl or aryl sulfonyl halide, preferably in the presence of at least one equivalent of base, for example by the procedure of C. Kowalski and K. Fields, J. Org. Chem., (1981), 46, 197-201.

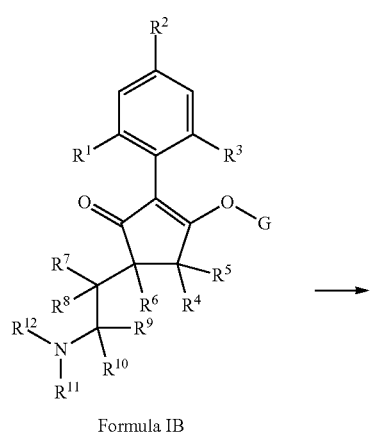

Formula IB

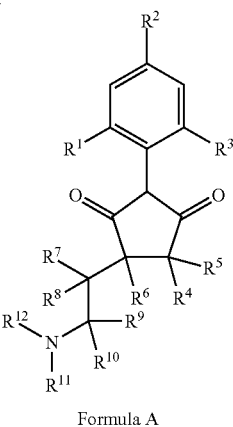

Formula A

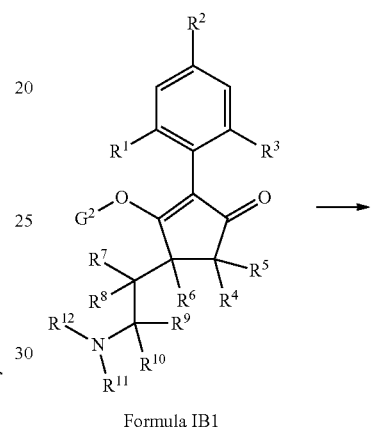

Formula IB1

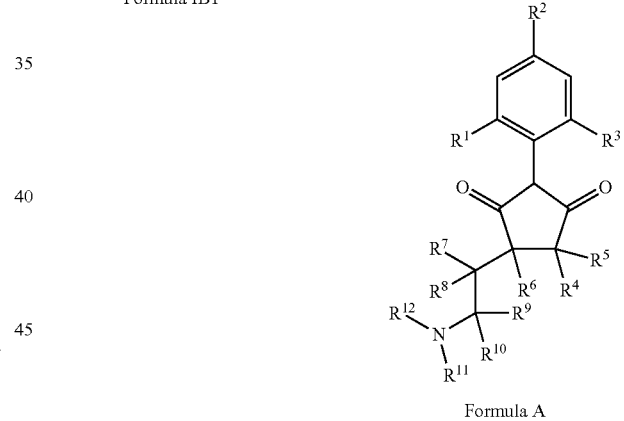

Formula A

A compound of Formula A may be prepared by the deprotection of a compound of Formula IB or 161 (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, e.g. as shown above. The deprotection is typically carried out in the presence of a suitable solvent (e.g. an aqueous solvent, or an organic solvent e.g. non-aqueous organic solvent, and/or a mixture of aqueous and/or organic solvents), in the presence of a suitable base and/or suitable acid. The deprotection is typically carried out either at ambient (room) temperature, or is heated thermally or under microwave irridiation. Suitable solvents may include N,N-dimethylformamide, acetone, tetrahydrofuran, water or dichloromethane or mixtures thereof. Suitable bases may include inorganic or organic bases such as metal hydroxide or tertiary amines such as morpholine. Suitable acids may include aqueous or organic acids such as trifluoroacetic acid, 4-methylbenzenesulfonic acid (p-TSA, para-toluenesulfonic acid), triflic acid (trifluoromethanesulfonic acid) or hydrochloric acid.

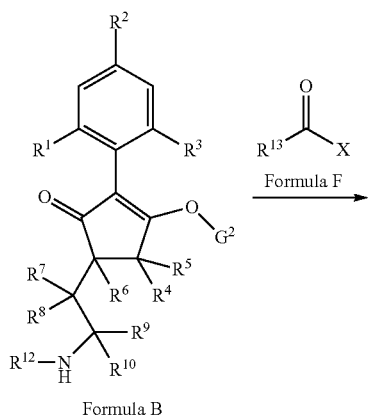

Formula B

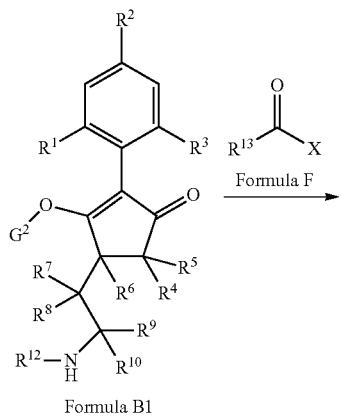

Formula B1

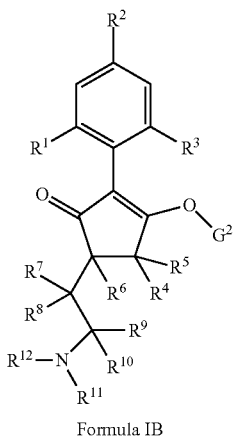

Formula IB

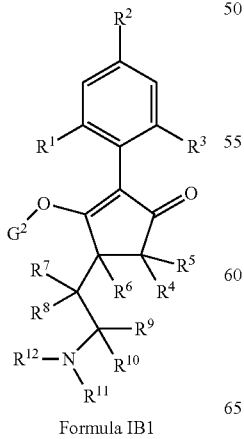

Formula IB1

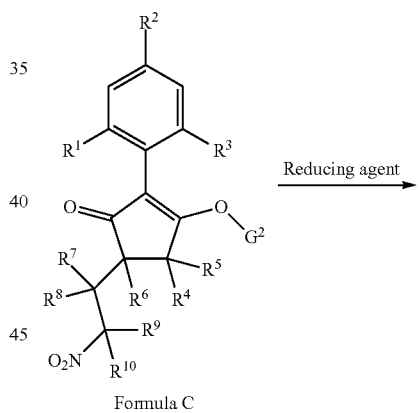

Formula C

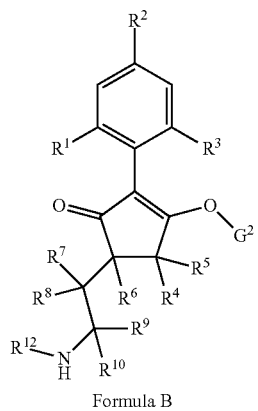

Formula B

A compound of Formula IB or IB1 where $R^{11}=\!\!-\!\!C(O)R^{13}$ (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by an amide bond forming reaction between a compound of Formula B or B1 respectively and a compound of Formula F, wherein X=halogen, OH or OR (OR being a leaving group attached by oxygen, e.g. pentafluorophenoxy, or e.g. an alkyl, fluoroalkyl or aryl sulfonate such as methanesulfonate, trifluoromethanesulfonate or para-toluenesulfonate). The amide bond forming reaction is typically carried out in the presence of a suitable solvent (e.g. an organic and/or non-aqueous solvent), and/or in the presence of a suitable coupling reagent, and/or in the presence of a suitable base. Suitable solvents may include N,N-dimethylformamide or dichloromethane. Suitable coupling reagents may include a carbodiimide (e.g. dicyclohexylcarbodiimide, "DCC") or a phosphonic anhydride (e.g. 2,4,6-tripropyl-1,3,5,2,4,6-trioxatriphosphorinane-2,4,6-trioxide) or a (benzotriazol-1-yloxy)trialkylaminophosphonium salt (e.g. benzotriazol-1-yloxy(tripyrrolidin-1-yl)phosphonium hexafluorophosphate). Suitable bases may include organic non-aqueous bases or tertiary amines such as N,N-diisopropylethylamine or triethylamine.

-continued

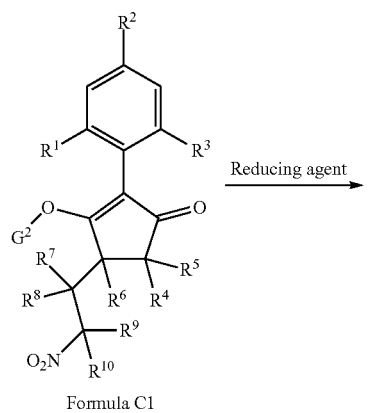

Formula C1

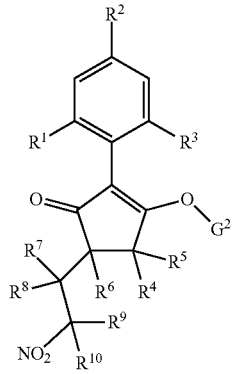

Formula C

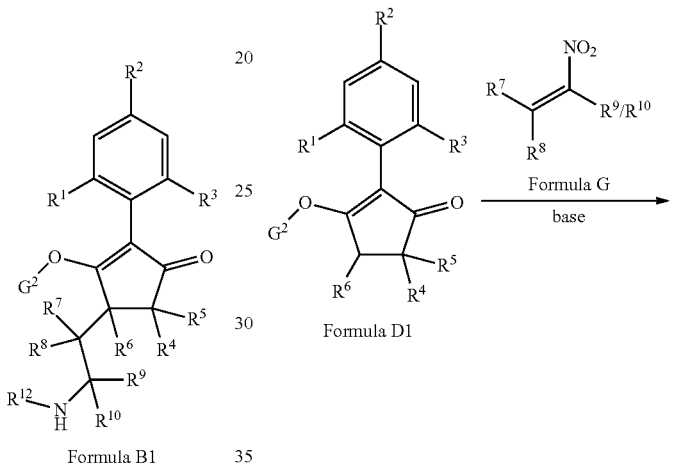

Formula B1

Compounds of Formula B or B1 (where $R^{12}$=H) may be prepared by the reduction of compounds of Formula C or C1 respectively in the presence of a suitable reducing agent, optionally in a suitable (e.g. organic) solvent, and/or in the presence of a suitable catalyst. Suitable reducing agents may include ammonium formate (see for example R. Ballini, F. Papa, C. Abate, *European Journal of Organic Chemistry*, 1, 87-90, 1999) or zinc dust. Suitable solvents may include methanol or acetic acid. Suitable catalysts may include, but are not limited to, palladium on carbon.

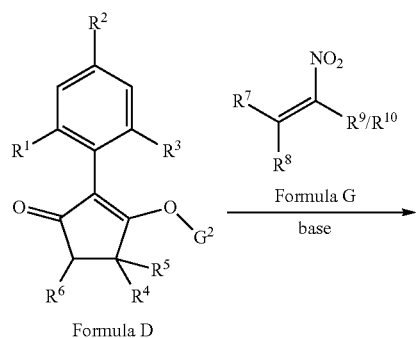

Formula D

Compounds of Formula C or C1 (in which typically at least one of $R^9$ and $R^{19}$ is hydrogen) may be prepared by reaction of a compound of Formula D or D1 respectively with a compound of Formula G, in the presence of a suitable base, at a suitable temperature, optionally in the presence of a suitable (e.g. organic) solvent. Suitable bases may include organic and/or non-aqueous bases, particularly strong organic and/or non-aqueous bases, such as lithium diisopropylamide (see for example T. J. Dickerson, T. Lovell, M. M. Meijler, L. Noodleman, K. D. Janda, *Journal of Organic Chemistry*, (2004) 69(20), 6603-6609) or potassium bis(trimethylsilyl)amide. Suitable temperatures range from −100° C. to 0° C. Suitable solvents may include tetrahydrofuran.

Compounds of Formula G can be prepared by known methods.

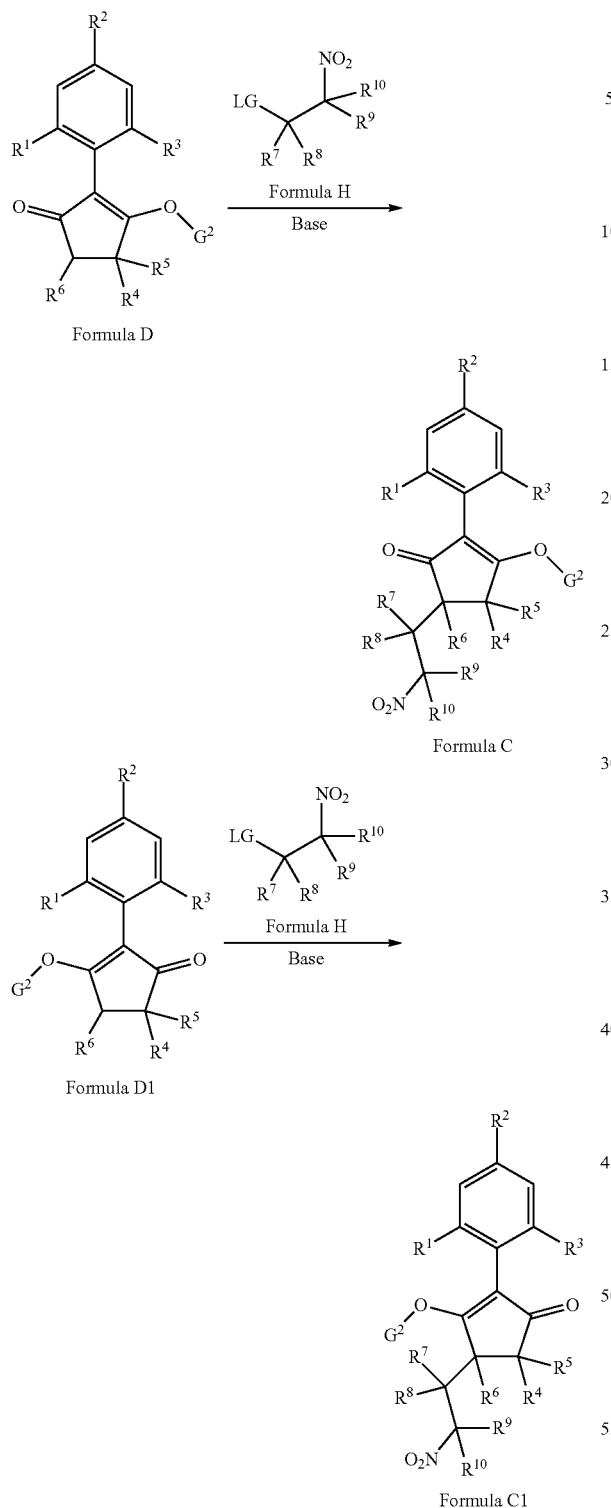

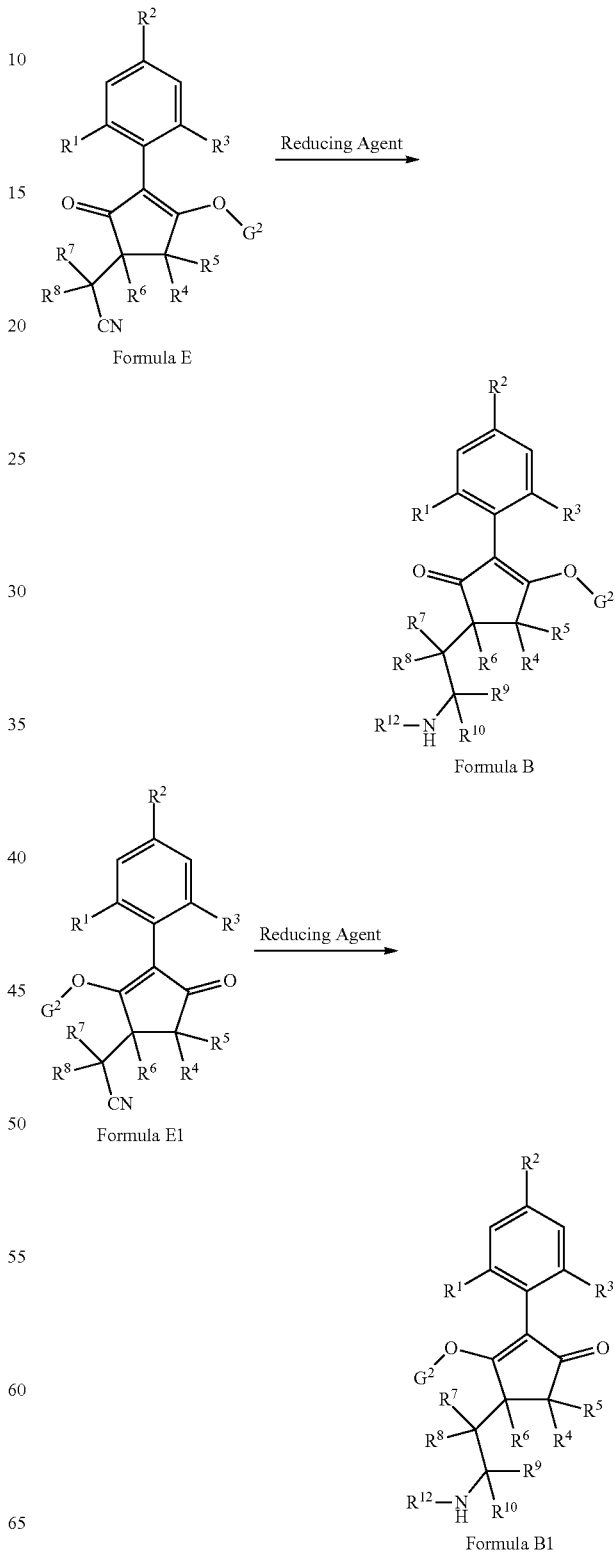

include lithium diisopropylamide. Suitable solvents may include tetrahydrofuran. Suitable temperatures range from −100° C. to 0° C.

Compounds of Formula H can be prepared by known methods.

In an alternative approach, compounds of Formula C or C1 may be prepared by alkylation of a compound of Formula D or D1 respectively with a compound of Formula H, where LG is a suitable leaving group (such as a halogen e.g. Cl or Br, or trifluoromethanesulfonate or acetate) in the presence of a suitable base at a suitable temperature, optionally in the presence of a suitable solvent. Suitable bases may In another alternative approach, compounds of Formula B or B1 (where $R^{12}$=H) may be prepared by reduction of compounds of Formula E or E1 respectively in the presence of a suitable reducing agent, optionally in the presence of a suitable (e.g. organic) solvent and/or in the presence of a suitable catalyst. Suitable reducing agents may include hydrogen gas, suitable solvents may include methanol, tetrahydrofuran or 1,4-dioxane. Suitable catalysts may include Raney®-Nickel (see for example C. Jellimann, M. Mathe-Allainmat, J. Andrieux, S. Kloubert, J. A. Boutin, J-P. Nicolas, C. Bennejean, P. Delagrange, M. Langlois, *Journal of Medicinal Chemistry*, (2000), 43(22), 4051-4062).

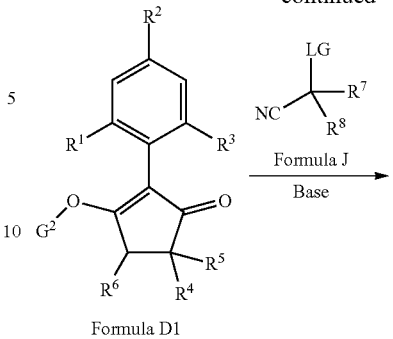

Formula D1

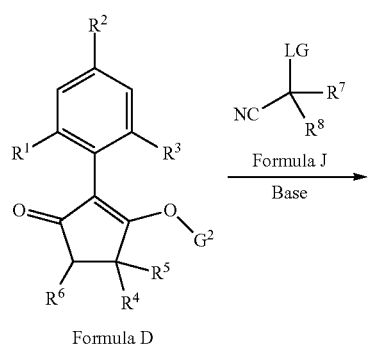

Formula D

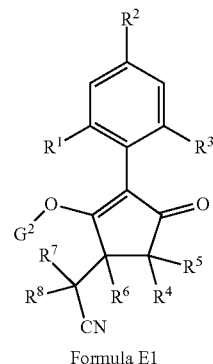

Formula E

Compounds of formula E or E1 may be prepared by alkylation of a compound of Formula D or D1 respectively with a compound of Formula J (wherein LG is a suitable leaving group, such as halogen e.g. Cl or Br, or such as an alkyl, fluoroalkyl or sulfonate e.g. methanesulfonate, trifluoromethanesulfonate or para-toluenesulfonate) in the presence of a suitable base, at a suitable temperature, optionally in the presence of a suitable (e.g. organic and/or non-aqueous) solvent. Suitable bases may include lithium diisopropylamide (LDA) (see for example R. Goswami, M. G. Moloney, *Chemical Communications*, (1999) 23, 2333-2334). Suitable solvents may include tetrahydrofuran. Suitable temperatures range from –100° C. to 0° C.

Compounds of Formula J can be prepared by known methods.

In one embodiment, compounds within Formula D or D1 are made using the processes shown below (these are compounds in which $R^2$ is Br, $R^1$ and $R^3$ are Me; $R^4$, $R^5$, and $R^6$ are H; and $G^2$ is Me).

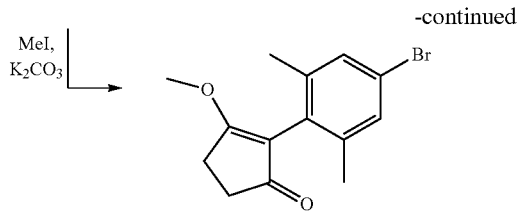

In an alternative embodiment, compounds within Formula D or D1 are made via the following coupling process scheme, as disclosed in Example 1 step 1 on pages 54-55 of WO 2010/000773 A1 and/or as disclosed in WO 2010/069834 A1 and/or WO 2011/073060 A2. The coupling process scheme below is illustrated for compounds of Formula D or D1 in which $R^1$, $R^2$ and $R^3$ are Me; $R^4$, $R^5$, and $R^6$ are H; and $G^2$ is Me:

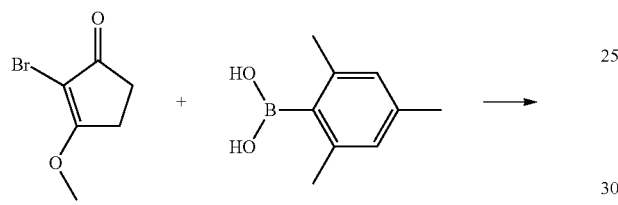

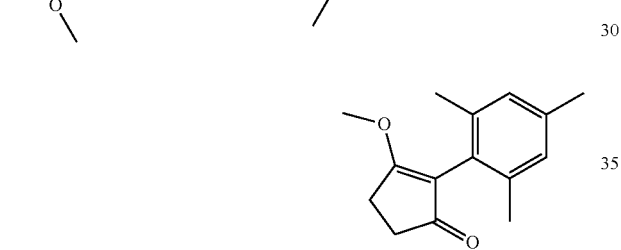

Typical reagents for the above-shown coupling process (the reagents used in Intermediate 1 herein, and in WO 2010/000773 A1) are potassium phosphate, $Pd(OAc)_2$, and S-Phos (which is 2-(dicyclohexylpho'ph'no)-2',6'-dimethoxybiphenyl). The 2,4,6-trimethyl-phenyl boronic acid shown above is commercially available.

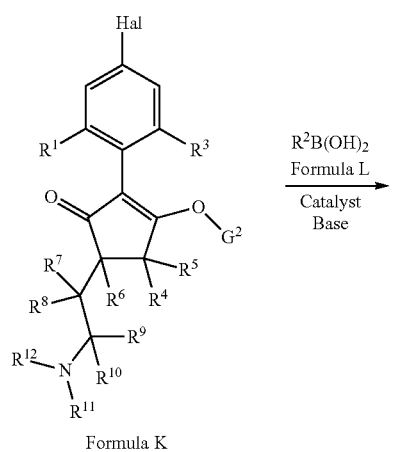

Formula K

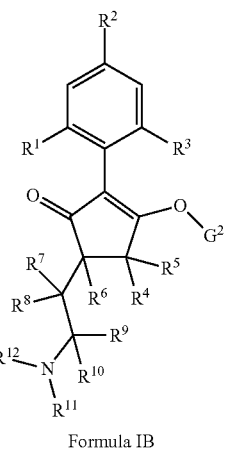

Formula IB

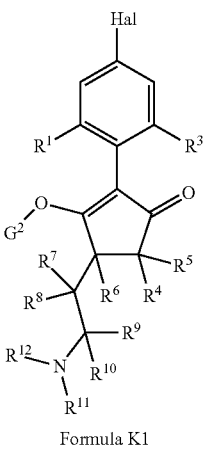

Formula K1

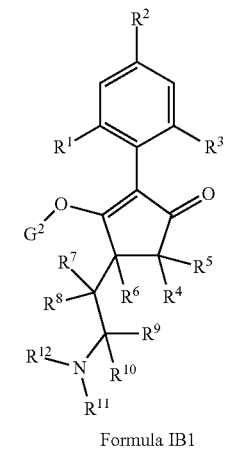

Formula IB1

In another approach, a compound of Formula IB or IB1 (which is sometimes also a compound of Formula (I) or (IA)

respectively), wherein R²=optionally substituted phenyl, $C_1$-$C_3$alkyl or cyclopropyl, and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction of compounds of Formula K or K1 respectively (where Hal=Cl, Br or I or a suitable "pseudohalogen" such as trifluoromethanesulfonate) with compound of Formula L in the presence of a suitable catalyst, and/or in the presence of a suitable base, at a suitable temperature, optionally in the presence of a suitable (e.g. organic and/or non-aqueous) solvent. Suitable catalysts may include bis(diphenylphosphino)ferrocene-dichloropalladium(II) (see for example A. M Thompson, H. S. Sutherland, B. D. Palmer, I. Kmentova, A. Blaser, W. A. Denny, S. G. Franzblau, B. Wan, Y. Wang, Z. Ma, *Journal of Medicinal Chemistry*, (2011), 54(19), 6563-6585). Suitable bases may include cesium fluoride. Suitable solvents may include 1,4-dioxane. Suitable temperatures range from room temperature (e.g. 15-30° C.) to 140° C.

Compounds of Formula L may be prepared by known methods.

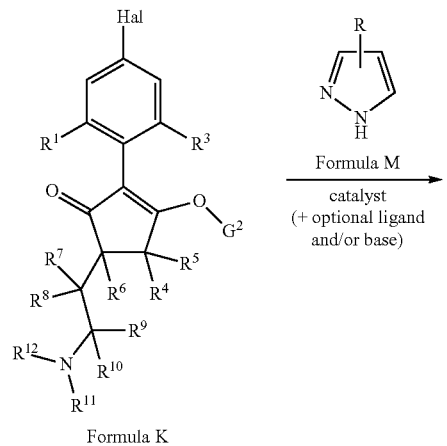

Formula K

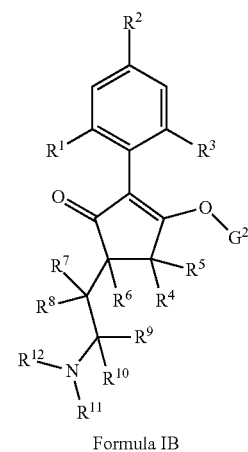

Formula IB

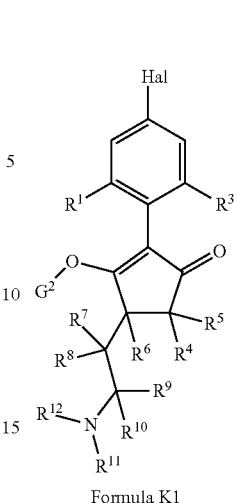

Formula K1

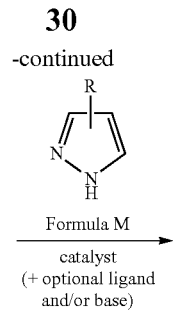

Formula M catalyst
(+ optional ligand and/or base)

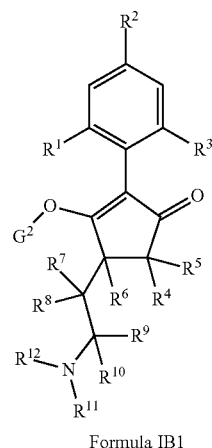

Formula IB1

In a further approach, a compound of Formula IB or IB1 (which is sometimes also a compound of Formula (I) or (IA) respectively), wherein R²=optionally substituted pyrazol-1-yl, and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction of compounds of Formula K or K1 respectively (where Hal=Cl, Br or I or a suitable "pseudohalogen" such as trifluoromethanesulfonate) with compounds of Formula M in the presence of a suitable catalyst, optionally in the presence of a suitable ligand, optionally in the presence of a suitable base, at a suitable temperature, optionally in the presence of a suitable (e.g. organic) solvent. Suitable catalysts may include copper (I) iodide (see for example H. Zhang, Q. Cai, D. Ma, *Journal of Organic Chemistry*, (2005), 70(13), 5164-5173) or tris (dibenzylideneacetone)dipalladium(0) (see for example S. Tasler, J. Mies, M. Lang, *Advanced Synthesis and Catalysis*, (2007), 349(14-15), 2286-2300). Suitable ligands may include dimethyl glycine or 2-di-tert-butylphosphino-2',4',6'-triisopropylbiphenyl. Suitable temperatures range from room temperature to 180° C. Suitable bases may include potassium carbonate or sodium hydride. Suitable solvents may include dimethyl sulfoxide, toluene or diethylene glycol dimethyl ether.

Compounds of Formula M are available or may be prepared by known methods.

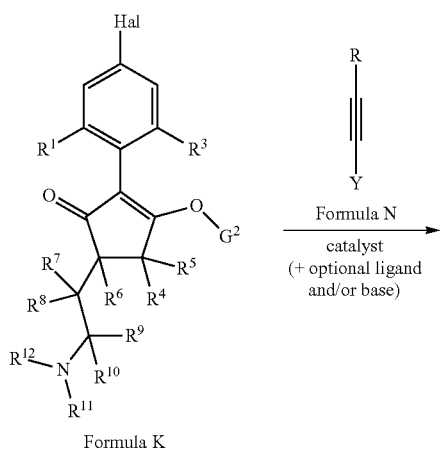

Formula K

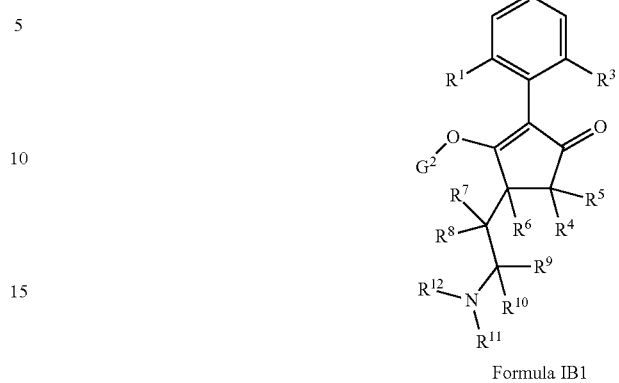

Formula IB1

In another approach, a compound of Formula IB or IB1 (which is sometimes also a compound of Formula (I) or (IA) respectively), wherein $R^2$=optionally substituted alkyn-1-yl (as defined herein), and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction of compounds of Formula K or K1 respectively (wherein R is suitable to form in formula I an $R^2$=optionally substituted alkyn-1-yl as defined herein) with compounds of Formula N (wherein Y is a suitable cross-coupling group such as H, $CO_2$H, $Bu_3$Sn or Grignard reagent) in the presence of a suitable catalyst, typically at a suitable temperature, optionally in the presence of a suitable (e.g. organic) solvent, optionally in the presence of a suitable ligand and/or a suitable base. Suitable catalysts may include [1,1'-Bis(diphenylphosphino)ferrocene]-dichloropalladium(II), copper (I) iodide or bis(triphenylphosphine)palladium(II) dichloride (see for example Y. Okuno, M. Yamashita, K. Nozaki, *European Journal of Organic Chemistry*, (2011), 20-21, 3951-3958). Suitable ligands may include 1,4-bis(diphenylphosphino)butane. Suitable bases may include cesium fluoride or 1,8-diazabicyclo[5.4.0]undec-7-ene. Suitable temperatures range from room temperature (e.g. 15-30° C.) to 140° C. Suitable solvents may include N,N-dimethylformamide or dimethylsulfoxide.

Compounds of Formula N may be prepared by known methods.

Formula IB

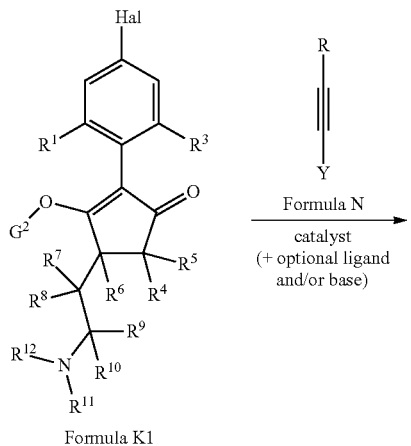

Formula K1

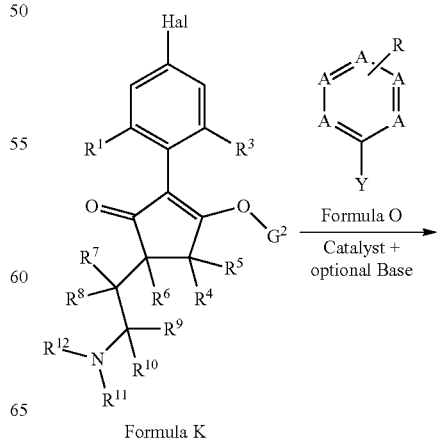

Formula K

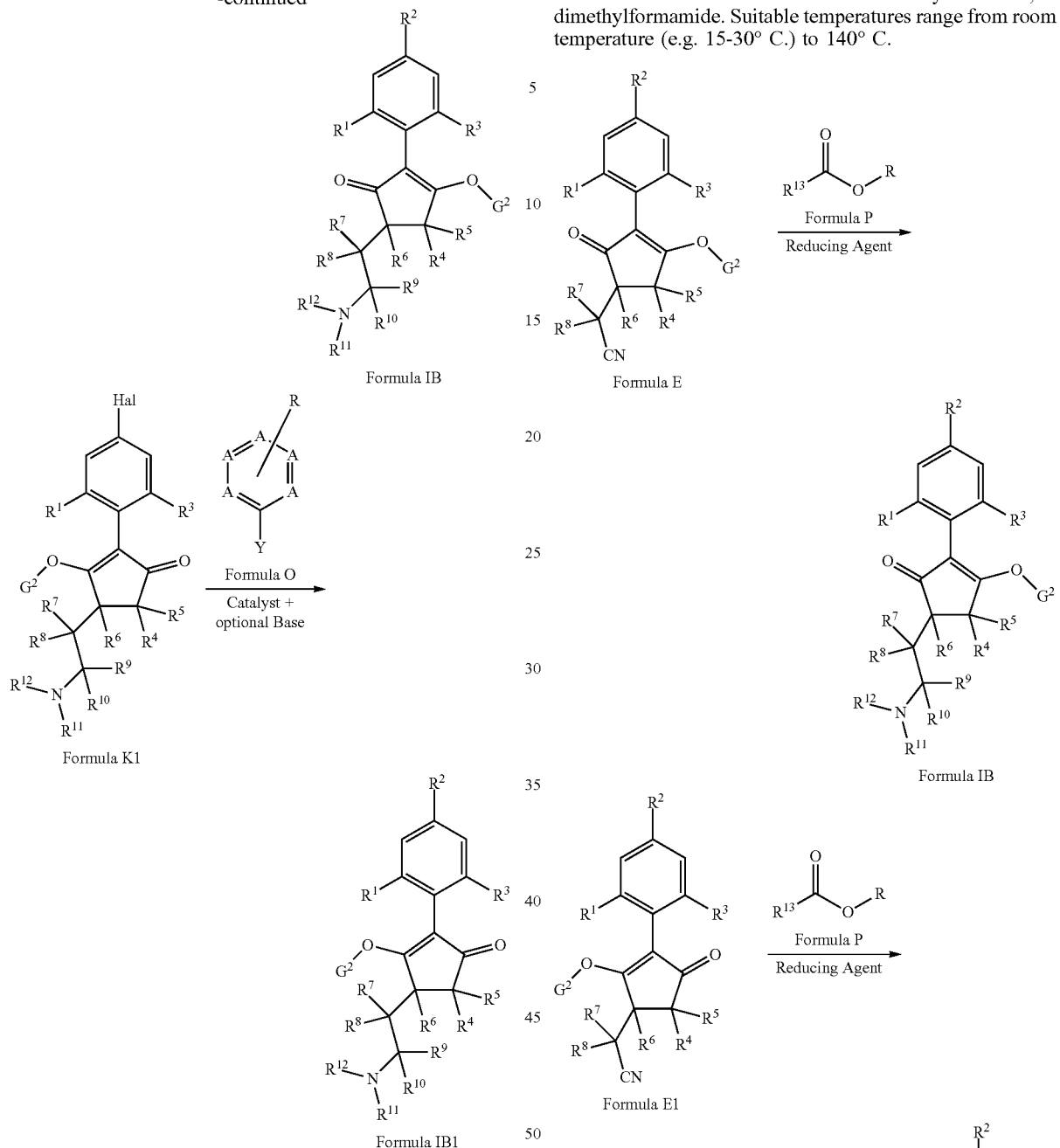

include cesium fluoride. Suitable solvents may include N,N-dimethylformamide. Suitable temperatures range from room temperature (e.g. 15-30° C.) to 140° C.

In a further approach, a compound of Formula IB or IB1 (which is sometimes also a compound of Formula (I) or (IA) respectively), wherein $R^2$=optionally substituted heteroaryl (e.g. optionally substituted 6-membered heteroaryl), and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reactions of compounds of Formula K or K1 respectively with compounds of Formula O (wherein Y is a suitable cross-coupling partner group e.g. B(OH)$_2$ or Bu$_3$Sn, and each A is independently C—R or N) in the presence of a suitable catalyst, at a suitable temperature, optionally in the presence of a suitable (e.g. organic) solvent, optionally in the presence of a suitable ligand and/or a suitable base. Suitable catalysts may include [1,1'-Bis(diphenylphosphino)ferrocene]dichloropalladium(II) (see for example N. Joubert, M. Urban, R. Pohl, M. Hocek, Synthesis, (2008), 12, 1918-1932) and copper (I) iodide. Suitable bases may

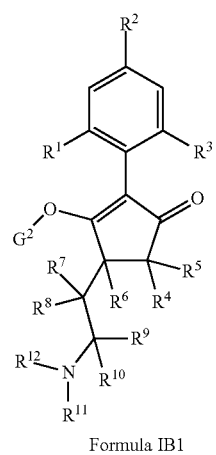

Formula IB1

In yet another approach, a compound of Formula IB or IB1 where $R^{11}$=—C(O)$R^{13}$ and $R^{12}$=H (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_5$alkyl or —C(O)N($C_1$-$C_6$alkyl)$_2$, can be prepared by reduction of compounds of Formula E or E1 in the presence of compounds of Formula P (in which O—R is a suitable leaving group, for example pentafluorophenoxy) in the presence of a suitable reducing agent, optionally in the presence of a suitable (e.g. organic) solvent and/or in the presence of a suitable catalyst. Suitable reducing agents may include sodium borohydride and hydrogen gas. Suitable solvents may include methanol, tetrahydrofuran or 1,4-dioxane. Suitable catalysts may include NiCl$_2$ or Raney®-Nickel (see for example D. E. Gonzalez-Juarez, J. B. Garcia-Vazquez, V. Zuniga-Garcia, J. J. Trujillo-Serrato, P. Joseph-Nathan, M. S. Morales-Rios, O. R. Suarez-Castillo, *Tetrahedron*, (2012), 68 (35), 7187-7195).

Compounds of Formula P can be prepared by known methods.

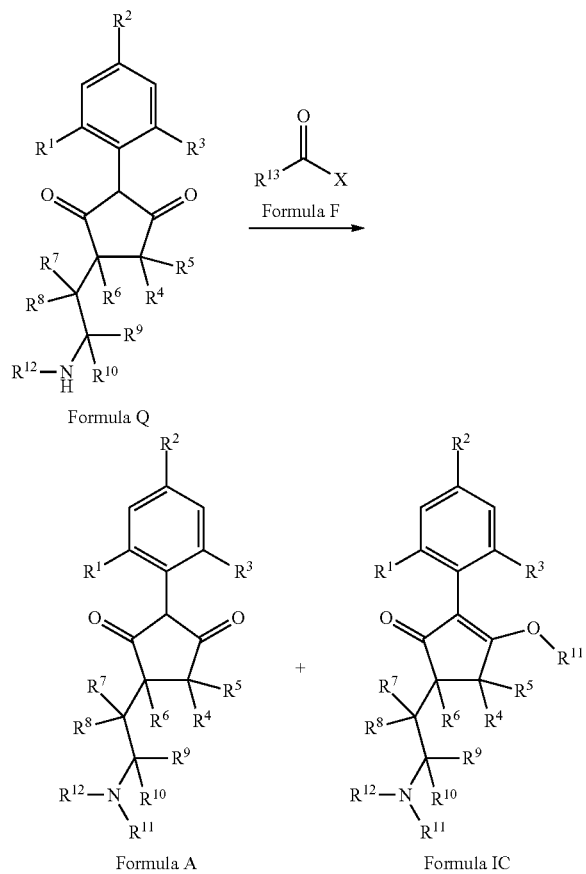

Formula Q

Formula A    Formula IC

A compound of formula (I) which is a compound of Formula A or of Formula IC where $R^{11}$=—C(O)$R^{13}$, may be prepared by an amide and/or ester bond forming reaction between a compound of Formula Q, or a salt thereof in particular an acid addition salt (e.g. HCl salt) thereof, and a compound of Formula F, wherein X=halogen, OH or OR (OR being a leaving group attached by oxygen, e.g. pentafluorophenoxy, or e.g. an alkyl, fluoroalkyl or aryl sulfonate such as methanesulfonate, trifluoromethanesulfonate or para-toluenesulfonate). The amide bond forming reaction is typically carried out in the presence of a suitable solvent (e.g. an organic and/or non-aqueous solvent), and/or in the presence of a suitable coupling reagent, and/or in the presence of a suitable base. Suitable solvents may include N,N-dimethylformamide or dichloromethane. Suitable coupling reagents may include a carbodiimide (e.g. dicyclohexylcarbodiimide, "DCC") or a phosphonic anhydride (e.g. 2,4,6-tripropyl-1,3,5,2,4,6-trioxatriphosphorinane-2,4,6-trioxide) or a (benzotriazol-1-yloxy)trialkylaminophosphonium salt (e.g. benzotriazol-1-yloxy(tripyrrolidin-1-yl)phosphonium hexafluorophosphate). Suitable bases may include organic non-aqueous bases or tertiary amines such as N,N-diisopropylethylamine or triethylamine.

Compounds of Formula F can be prepared by known methods.

The present invention also provides a compound of formula (Q):

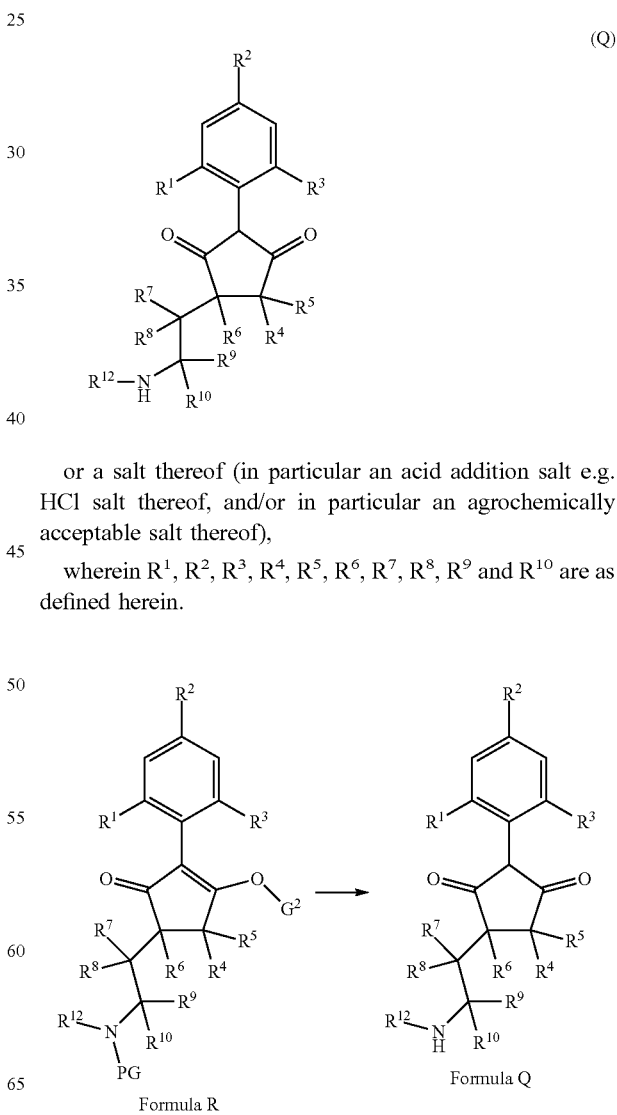

(Q)

or a salt thereof (in particular an acid addition salt e.g. HCl salt thereof, and/or in particular an agrochemically acceptable salt thereof), wherein $R^1$, $R^2$, $R^3$, $R^4$, $R^5$, $R^6$, $R^7$, $R^8$, $R^9$ and $R^{10}$ are as defined herein.

Formula R    Formula Q

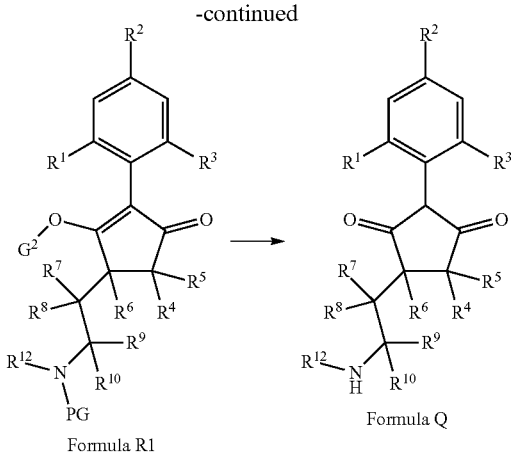

Formula R1 → Formula Q

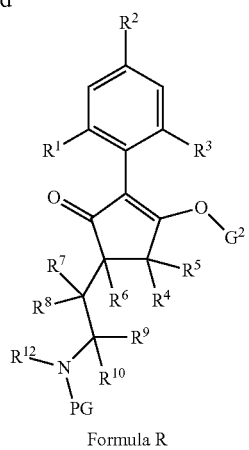

Formula R

A compound of Formula Q or a salt (e.g. acid addition salt, e.g. HCl salt) thereof may be prepared from a compound of Formula R or R1 by removing the protecting group (PG), wherein PG is a suitable protecting group, preferably tert-butyloxycarbonyl (t-Boc), carboxybenzyl (CBz), para-toluenesulfonyl (tosyl, Ts), para-bromobenzenesulfonyl, 2- or 4-nitrobenzenesulfonyl (nosyl, Nos), 2,2,2-trichloroethoxycarbonyl (Troc), benzyl (Bn), p-methoxybenzyl (PMB), fluorenylmethyloxycarbonyl (Fmoc) or any other suitable protecting group. The removal of the protecting group (PG) is typically carried out in the presence of a suitable solvent (e.g. an organic and/or aqueous solvent), in the presence of a suitable acid, base, reducing agent and/or oxidizing agent. Suitable solvents may include N,N-dimethylformamide, dichloromethane, tetrahydrofuran, diethylether, water, ethyl acetate or acetone or mixtures thereof. Suitable acids may include trifluoroacetic acid, hydrochloric acid or triflic acid (trifluoromethanesulfonic acid). Suitable bases may include tertiary amines such as N,N-diisopropylethylamine or triethylamine, or a metal alkoxide, or a metal hydroxide or morpholine. Suitable reducing agents may include zinc, hydrogen gas in the presence of suitable metal catalysts, alkali metals dissolved in ammonia, or a sodium amalgam. Suitable oxidizing agents may include ceric ammonium nitrate (CAN).

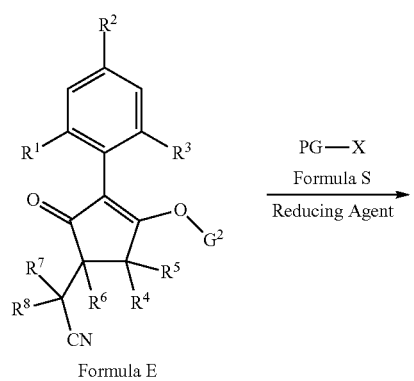

Formula E

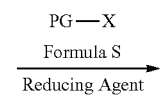

PG—X
Formula S
Reducing Agent

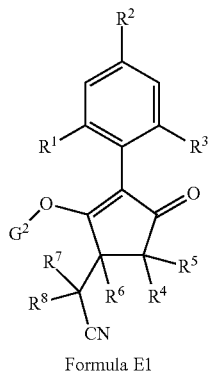

Formula E1

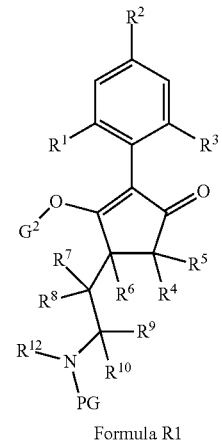

Formula R1

Compounds of Formula R or R1 (where $R^{12}$=H) can be prepared by reduction of compounds of Formula E or E1 respectively in the presence of compounds of Formula S (in which X is a suitable leaving group, for example halogen, or anhydride where X=O—PG) in the presence of a suitable reducing agent, optionally in the presence of a suitable (e.g. organic) solvent and/or in the presence of a suitable catalyst. Suitable reducing agents may include hydrogen gas or sodium borohydride. Suitable solvents may include methanol, tetrahydrofuran or 1,4-dioxane. Suitable catalysts may include $NiCl_2$ or Raney®-Nickel (see for example D. E. Gonzalez-Juarez, J. B. Garcia-Vazquez, V. Zuniga-Garcia, J. J. Trujillo-Serrato, P. Joseph-Nathan, M. S. Morales-Rios, O. R. Suarez-Castillo, *Tetrahedron*, (2012), 68 (35), 7187-7195).

Compounds of Formula S can be prepared by known methods.

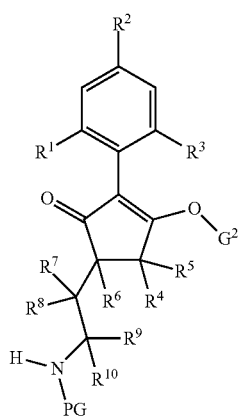

Formula T

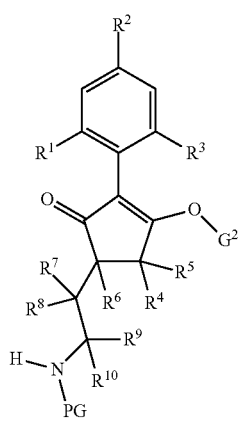

Formula T1

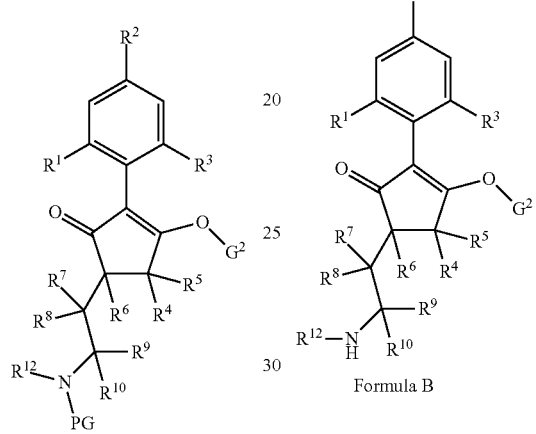

Formula R

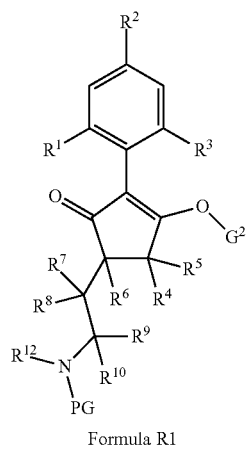

Formula R1

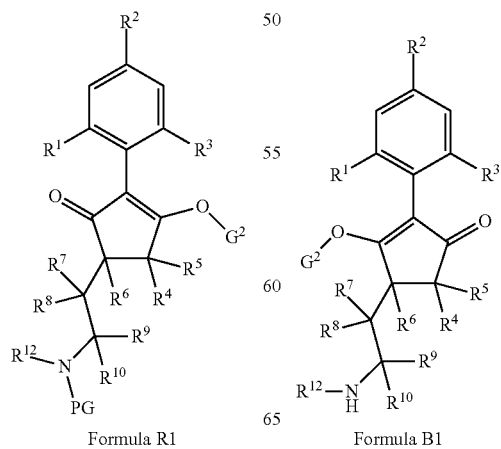

Formula B1

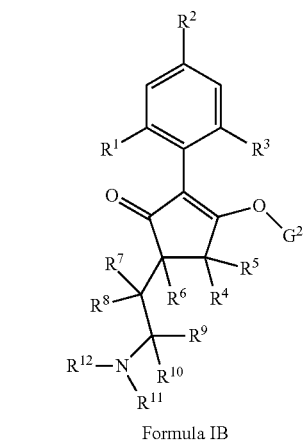

Formula IB

Compounds of Formula R or R1 (where $R^{12}$=alkyl, haloalkyl, alkoxyalkyl) can be prepared by reacting Formula T or T1 respectively in the presence of compounds of Formula U (in which X is a suitable leaving group, for example halogen, in the presence of a suitable base, and in the presence of a suitable (e.g. organic) solvent. Suitable bases may include metal hydride, n-butyl lithium and sodium methoxide. Suitable solvents may include methanol, tetrahydrofuran or 1,4-dioxane.

Compounds of Formula U can be prepared by known methods.

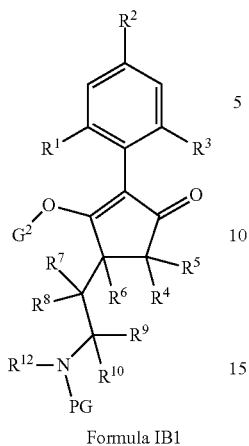

Formula IB1

A compound of Formula IB or IB1 where $R^{11}$=—S(O)$_2$ $R^{14}$ (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by a sulfonamide bond forming reaction between a compound of Formula B or B1 respectively and a compound of Formula V, wherein X=halogen or OR (OR being a leaving group attached by oxygen, e.g. pentafluorophenoxy, or e.g. an alkyl, fluoroalkyl or aryl sulfonate such as methanesulfonate, trifluoromethanesulfonate or para-toluenesulfonate). The sulfonamide bond forming reaction is typically carried out in the presence of a suitable solvent (e.g., an organic and/or non-aqueous solvent) and/or in the presence of a suitable base. Suitable solvents may include N,N-dimethylformamide or dichloromethane. Suitable bases may include organic non-aqueous bases such as tertiary amines for example N,N-diisopropylethylamine or triethylamine.

Compounds of Formula V can be prepared by known methods.

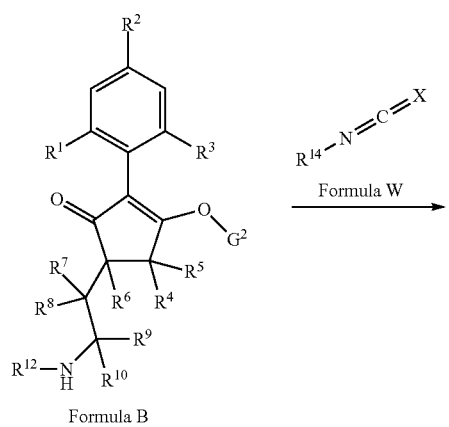

Formula B

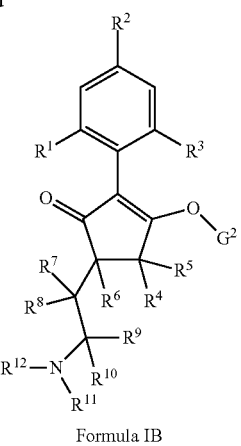

Formula IB $R^{14}$—N=C=X

Formula W

Formula B1

Formula IB1

A compound of Formula IB or IB1 where $R^{11}$=—NC(X)NH$R^{14}$ (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction between a compound of Formula B or B1 and an isocyanate or isothiocyanate compound of Formula W, wherein X=oxygen or sulfur. The reaction is typically carried out at a suitable temperature, including microwave irradiation, in the presence of a suitable solvent (e.g. an organic and/or non-aqueous solvent) and/or in the presence of a suitable base. Suitable solvents may include acetonitrile, N,N-dimethylformamide or dichloromethane. Suitable bases may include organic non-aqueous bases such as tertiary amines for example N,N-diisopropylethylamine or triethylamine. Compounds of Formula W are commercially available or can be prepared by known methods.

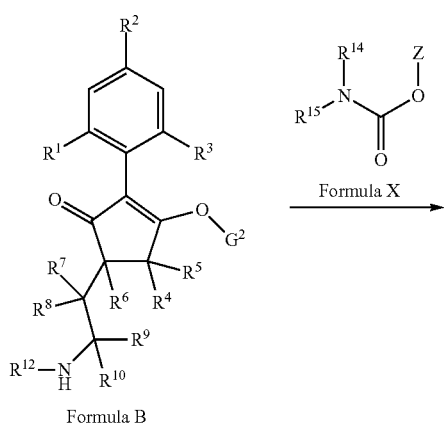

mula (I) or (IA) respectively) may also be prepared by reaction between a compound of Formula B or B1 and an activated carbamate of Formula X, wherein O—Z is a suitable leaving group, for example, phenoxy, 2,4,6-trichlorophenoxy or pentafluorophenoxy. The reaction is typically carried out at a suitable temperature, including microwave irradiation, in the presence of a suitable solvent (e.g. an organic and/or non-aqueous solvent) and/or in the presence of a suitable base. Suitable solvents may include acetonitrile, N,N-dimethylformamide or dichloromethane. Suitable bases may include organic non-aqueous bases such as tertiary amines for example N,N-diisopropylethylamine or triethylamine. Compounds of Formula X are commercially available or can be prepared by known methods.

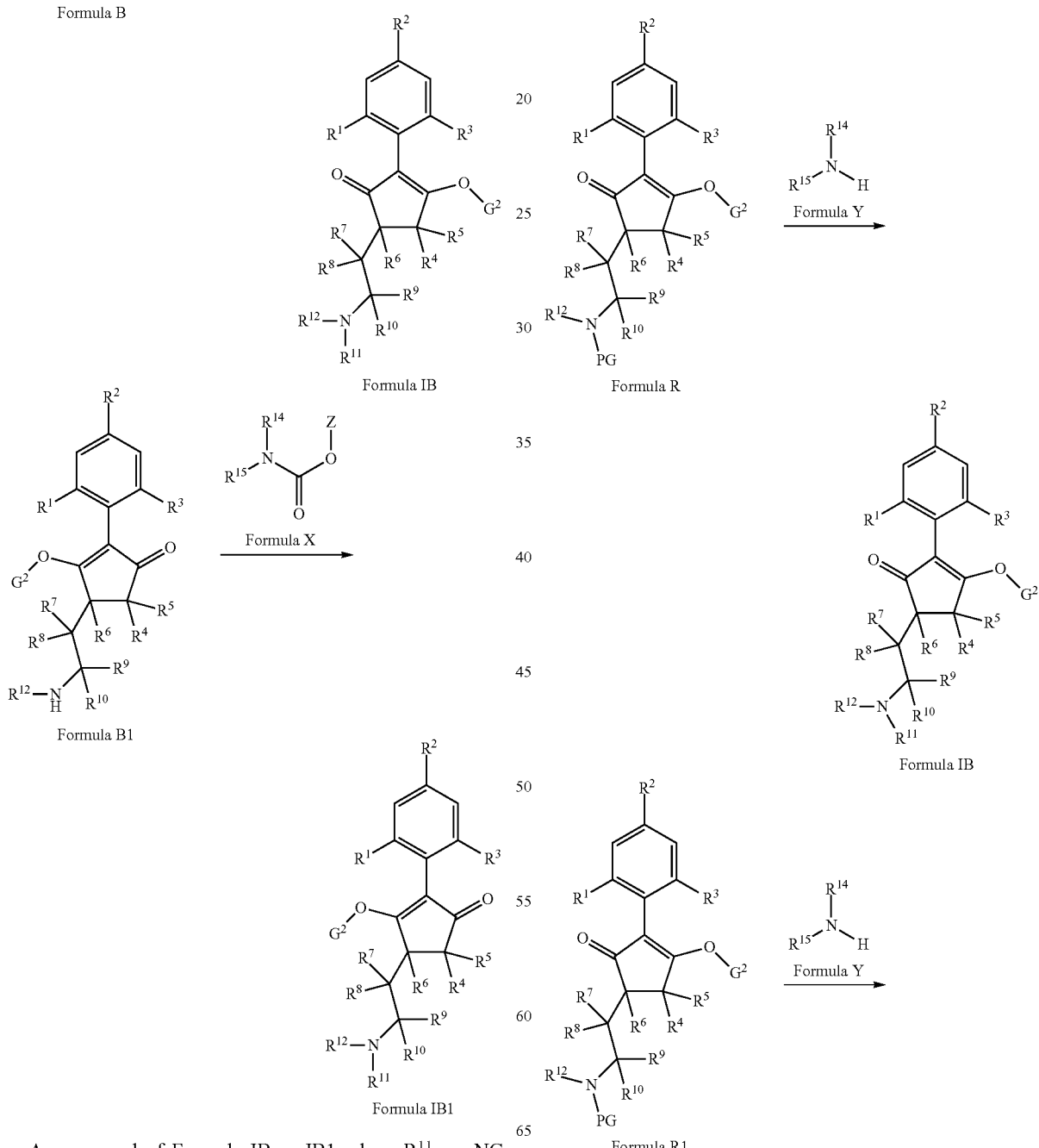

A compound of Formula IB or IB1 where $R^{11}$=—NC(O)$NR^{14}R^{15}$ (which is sometimes also a compound of For-

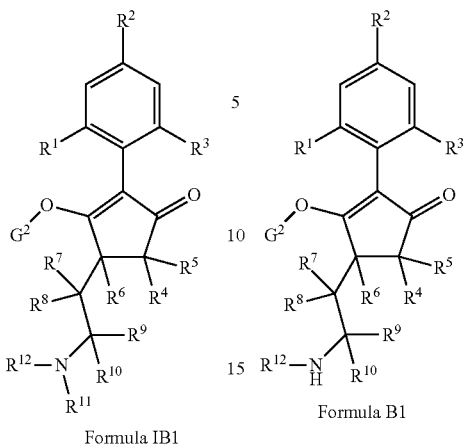

Formula IB1

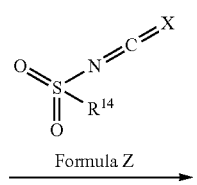

Formula Z

Formula B1

A compound of Formula IB or IB1 where $R^{11}$=—NC(O)$NR^{14}R^{15}$ (which is sometimes also a compound of Formula (I) or (IA) respectively) and where $R^{15}$ could also be —$NR^{16}R^{17}$ or —$OR^{18}$ may also be prepared by reaction between a compound of Formula R or R1, or where $R^{12}$=H, i.e. a compound of formula T or T1, wherein PG is an activated carbamate —C(O)O—Z, wherein O—Z is a suitable leaving group, for example, phenoxy, 2,4,6-trichlorophenoxy or pentafluorophenoxy, and an amine of Formula Y. The reaction is typically carried out at a suitable temperature, including microwave irradiation, in the presence of a suitable solvent (e.g. an organic and/or non-aqueous solvent) and/or in the presence of a suitable base. Suitable solvents may include acetonitrile, N,N-dimethylformamide or dichloromethane. Suitable bases may include organic non-aqueous bases such as tertiary amines for example N,N-diisopropylethylamine or triethylamine. Compounds of Formula Y are commercially available or can be prepared by known methods.

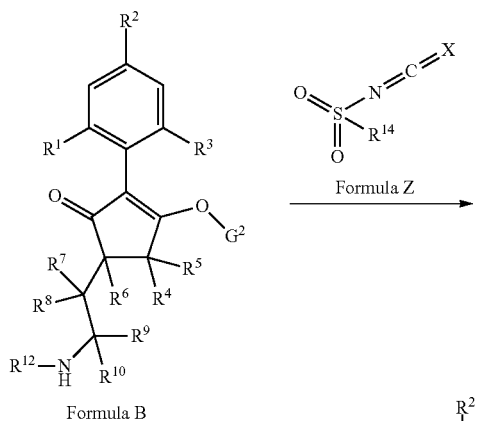

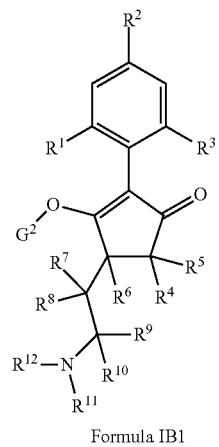

Formula Z

Formula B

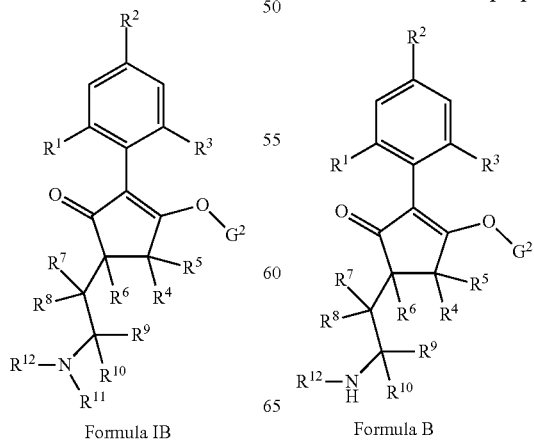

Formula IB1

A compound of Formula IB or IB1 where $R^{11}$=—NC(X)NHS(O)$_2R^{14}$ (which is sometimes also a compound of Formula (I) or (IA) respectively) may be prepared by reaction between a compound of Formula B or B1 and an isocyanate or isothiocyanate compound of Formula Z, wherein X=oxygen or sulfur. The reaction is typically carried out at a suitable temperature, including microwave irradiation, in the presence of a suitable solvent (e.g. an organic and/or non-aqueous solvent) and/or in the presence of a suitable base. Suitable solvents may include acetonitrile, N,N-dimethylformamide or dichloromethane. Suitable bases may include organic non-aqueous bases such as tertiary amines for example N,N-diisopropylethylamine or triethylamine. Compounds of Formula Z are commercially available or can be prepared by known methods.

Formula IB

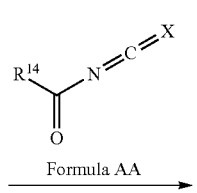

Formula AA

Formula B

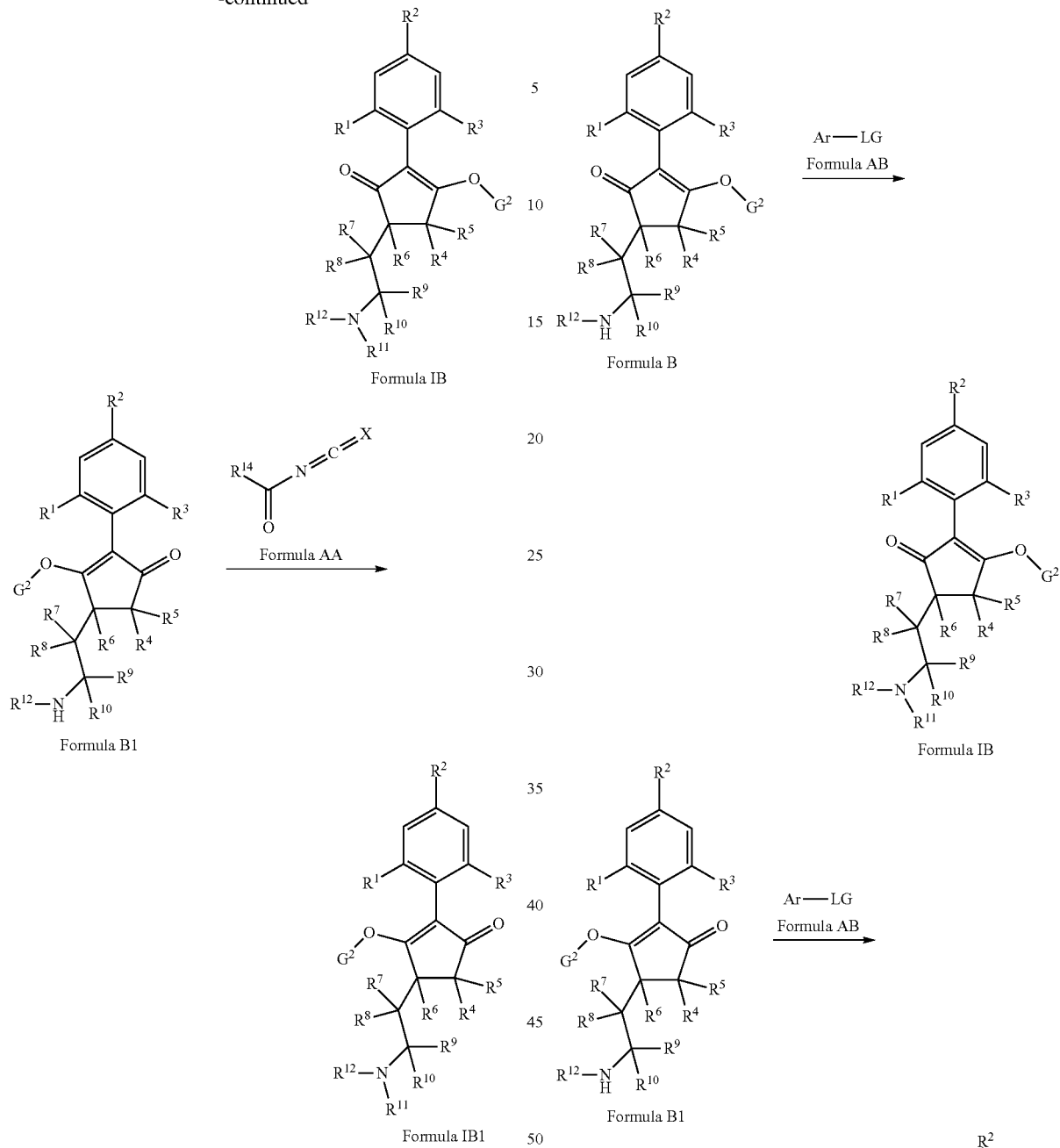

A compound of Formula IB or IB1 where $R^{11}$=—NC(X)NHC(O)$R^{14}$ (which is sometimes also a compound of Formula (I) or (IA) respectively) may be prepared by reaction between a compound of Formula B or B1 and an isocyanate or isothiocyanate compound of Formula AA, wherein X=oxygen or sulfur. The reaction is typically carried out at a suitable temperature, including microwave irradiation, in the presence of a suitable solvent (e.g. an organic and/or non-aqueous solvent) and/or in the presence of a suitable base. Suitable solvents may include acetonitrile, N,N-dimethylformamide or dichloromethane. Suitable bases may include organic non-aqueous bases such as tertiary amines for example N,N-diisopropylethylamine or triethylamine. Compounds of Formula AA are commercially available or can be prepared by known methods.

A compound of Formula IB or IB1 where $R^{11}$ is activated phenyl (e.g. fluorophenyl) or heteroaryl which is sometimes also a compound of Formula (I) or (IA), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$ or H, may be prepared by reaction between a compound of Formula B or B1 and a compound of Formula AB, wherein LG is a suitable leaving group, such as halogen e.g. F, Cl or Br, or such as a sulfonate e.g. methanesulfonate, trifluoromethanesulfonate or paratoluenesulfonate. The reaction is typically carried out at a suitable temperature, including microwave irradiation, in the presence of a suitable solvent (e.g. an organic and/or non-aqueous solvent) and/or in the presence of a suitable base. Suitable solvents may include acetonitrile, N,N-dimethylformamide or dichloromethane. Suitable bases may include organic non-aqueous bases such as tertiary amines for example N,N-diisopropylethylamine or triethylamine, or inorganic bases (with or without the presence of water) such as metal carbonates, or a mixture of both. Compounds of Formula AB are commercially available or can be prepared by known methods.

Herbicidal Compositions

In another aspect, the present invention provides a herbicidal composition, e.g. for use in a method of controlling weeds (preferably monocotyledonous such as grassy monocotyledonous weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

In a further aspect, the present invention provides a herbicidal composition, e.g. for use in a method of controlling weeds (preferably monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one particular embodiment, the herbicidal composition also comprises one or more further herbicides, e.g. as mixture partner(s) for the compound of formula (I), and/or a safener. See the combinations and mixtures section herein for more details of examples of these.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micro-nutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxson, a nondearomatized hydrocarbon solvent with a boiling range between 100 and 320° C. (e.g. known under the tradename Varson, an isoparaffinic solvent with a boiling range between 100 and 320° C. (e.g. known known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate; an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropyleneglycol with a molecular mass of 400-4000, or glycerol;

glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcoholalkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, antifoams, complexing agents, neutralising or pH-modifying substances and/or buffers, corrosion-inhibitors, fragrances, wetting agents, absorption improvers, micronutrients, plasticisers, glidants, lubricants, dispersants, thickeners, antifreezes, microbiocides, compatibility agents and/or solubilisers; and/or also liquid and/or solid fertilisers.

The herbicidal compositions (formulations) may also comprise additional active substances, for example further herbicides, herbicide safeners, plant growth regulators, fungicides or insecticides.

The herbicidal compositions according to the invention can additionally include an additive (commonly referred to as an adjuvant), comprising a mineral oil, an oil of vegetable or animal origin, alkyl (e.g. $C_1$-$C_6$alkyl) esters of such oils or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable anionic, non-ionic, cationic or amphoteric surfactants, e.g. for this purpose, are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic sufactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, heavy aromatic hydrocarbon solvents such as SOLVESSO® or AROMATIC® solvents (Exxon Corporation). The concentration of such solvents can e.g. be from 10 to 80% by weight of the oil additive (oil adjuvant). Such oil additives (oil adjuvants), which may be in admixture with solvents, are described, for example, in U.S. Pat. No. 4,834,908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal compositions of the invention, is an emulsifiable concentrate which consists of:

(i) ethoxylated alcohols, which preferably includes ethoxylated $C_{12}$-$C_{22}$ fatty alcohols (preferably having a degree of ethoxylation of from 5 to 40);

(ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and (iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta.

When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agrochemically acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agrochemically acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl) phosphate, tris-n-octyl phosphate and/or tris-[2-(n-butoxy)ethyl]phosphate, or most preferably is tris-(2-ethylhexyl) phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl (n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agrochemically acceptable substance, which preferably includes a formulation adjuvant and/or from 0 to 30% or from 0 to 25% (in particular from 0.5 to 30% or from 0.5 to 25%) by weight of a surface-active substance. Whereas herbicidal compositions (especially commercial products) will preferably be formulated as concentrates, the end user will normally employ dilute formulations (herbicidal compositions), e.g. formulations (herbicidal compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):
Emulsifiable Concentrates:
active ingredient: 0.3 to 95%, preferably 0.5 to 60% such as 1 to 40%
surface-active agents: 1 to 30%, preferably 3 to 20% such as 5 to 15%
solvents as liquid carrier: 1 to 80%, preferably 1 to 60% such as 1 to 40%
Dusts:
active ingredient: 0.1 to 10%, preferably 0.1 to 5%
solid carriers: 99.9 to 90%, preferably 99.9 to 99%
Suspension Concentrates:
active ingredient: 1 to 75%, preferably 3 to 50% or 10 to 50%
water: 98 to 24%, preferably 95 to 30% or 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Water-dispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
| --- | --- | --- | --- | --- |
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

| F8. Dusts | a) | b) | c) |
| --- | --- | --- | --- |
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | a) | b) | c) | d) |
| --- | --- | --- | --- | --- |
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses-Crops of Useful Plants, Weeds, Application Rates.

In a further aspect, the present invention provides a method of controlling weeds (e.g. monocotyledonous weeds such as grassy monocotyledonous weeds) in crops of useful plants, which comprises applying a compound of the formula (I), or a herbicidal composition comprising such a compound, to the weeds and/or to the plants and/or to the locus thereof.

In a further aspect, the present invention provides a herbicidal composition, in particular for use in a method of controlling weeds (preferably monocotyledonous weeds, more preferably grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one particular embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular, cereals (preferably non-oat cereals, in particular wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is Phaseolus vulgaris, or mung bean which is Vigna radiata), chickpea, blackeye bean (i.e. black-eyed pea, Vigna unguiculata), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry).

Preferably, in all aspects of the invention, the crops of useful plants, e.g. on or in which or at the locus of which the compounds or compositions according to the invention can be used, comprise (e.g. are) cereals (preferably non-oat cereals, more particularly wheat, barley, rye and/or triticale), rice, corn (maize), sugarcane, leguminous crops (preferably soybean, peanut, and/or pulse crops, more preferably soybean), cotton, rape (in particular oilseed rape or canola), sunflower, linseed, sugarbeet, fodder beet, potato, and/or vegetables (preferably dicotyledonous vegetables).

Most preferably, in all aspects of the invention, the crops of useful plants, e.g. on or in which or at the locus of which the compounds or compositions according to the invention can be used, comprise (e.g. are) non-oat cereals, more particularly wheat, barley, rye and/or triticale.

The term "crops" is to be understood as also including crops that have been rendered tolerant to herbicides or classes of herbicides (for example ALS, GS, EPSPS, PPO and/or HPPD inhibitors, and/or 2,4-D or dicamba) as a result of conventional methods of breeding or genetic engineering. An example of a crop that has been rendered tolerant e.g. to imidazolinones (which are ALS inhibitors), such as imazamox, by conventional methods of breeding is Clearfield® summer rape (canola) and/or Clearfield® wheat and/or Clearfield® rice (all from BASF). Examples of crops that have been rendered tolerant to herbicides by genetic engineering methods include e.g. glyphosate- or glufosinate-resistant/tolerant maize or soybean varieties, in particular those commercially available under the trade name RoundupReady® or RoundupReady® 2 (both from Monsanto, both glyphosate-tolerant) or LibertyLink® (from Bayer, glufosinate-tolerant). Glufosinate-tolerant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy monocotyledonous) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass").

In one preferred embodiment of all aspects of the invention, the monocotyledonous weeds, e.g. to be controlled and/or growth-inhibited, are grassy monocotyledonous weeds; in which case they typically comprise (e.g. are) weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*.

In one particular embodiment of all aspects of the invention, the grassy monocotyledonous weeds, e.g. to be controlled and/or growth-inhibited, are "warm-season" grassy weeds; in which case they typically comprise (e.g. are) weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*.

In another particular embodiment of all aspects of the invention, the grassy monocotyledonous weeds, e.g. to be controlled and/or growth-inhibited, are "cool-season" grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (e.g. *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition (2009) or 16th edition (2012), ed. C.D.S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylaminocarbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis,*

*Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca,* and/or *Sorghum halapense*; or can more particularly comprise *Alopecurus myosuroides, Apera spica-venti, Avena fatua, Avena sterilis, Digitaria sanguinalis, Echinochloa colona, Echinochloa crus-galli, Lolium multiflorum, Lolium rigidum, Lolium perenne, Phalaris minor, Phalaris paradoxa, Setaria viridis, Setaria faberi* and/or *Sorghum halapense*.

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.,* 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.,* 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.,* 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium*.

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the free compound, i.e. excluding the weight of any associated salt counterion(s)), in particular from 5 to 500 g/ha, preferably from 10 to 400 g/ha, of the compound of formula (I) (measured as the salt-free compound, i.e. excluding the weight of any associated salt counterion(s)).

In all aspects of the invention, the compound of formula (I) can be applied (typically to the weeds and/or to the crops of useful plants and/or to the locus thereof) pre- and/or post-emergence, but preferably is applied post-emergence.

Combinations and Mixtures

In a further aspect, the present invention provides a herbicidal composition, e.g. for use in a method of controlling weeds (in particular monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt (e.g. agrochemically acceptable metal, sulfonium or ammonium salt) thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of the specific compounds disclosed herein e.g. hereinbelow, present either as a free compound and/or as an agrochemically acceptable salt thereof.

In particular, the following mixtures of the compound of formula (I) with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3, 4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate (see e.g. US2012/0184434A1), compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+pic1oram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-d ichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2, 6-d ioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl [(1RS)-1-(2,4-dichlorophenoxyacetoxy)ethyl]phosphonate, also named lvxiancaolin or luxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition (2009) or 16th edition (2012), ed. C.D.S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuronmethyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl) pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl) pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl) urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2); wherein the mixture partners for the compound of formula (I) may optionally be in the form of an ester (in particular an agrochemically acceptable ester) or a salt (in particular an agrochemically acceptable salt) thereof (e.g. where chemically possible).

The following mixtures with safeners, especially, come into consideration:

compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

The above-mentioned safeners and herbicides are described, for example, in the Pesticide Manual, 14th Edition, British Crop Production Council, 2006; or The Pesticide Manual 15$^{th}$ edition (2009) or 16th edition (2012), ed. C.D.S. Tomlin, British Crop Production Council. R-29148 is described, for example by P.B. Goldsbrough et al., Plant Physiology, (2002), Vol. 130 pp. 1497-1505 and references therein. PPG-1292 is known from WO 2009/211761. N-(2-methoxybenzoyl)-4-[(methylaminocarbonyl)amino]benzenesulfonamide is known from e.g. EP365484.

Even more preferably, the safener comprises (e.g. is) cloquintocet-mexyl, cloquintocet acid or an agrochemically acceptable salt thereof, mefenpyr-diethyl and/or isoxadifen-ethyl; in particular for use on non-oat cereals such as wheat, barley, rye and/or triticale.

Cloquintocet-mexyl is particularly valuable and is the most preferred safener, especially for use on non-oat cereals such as wheat, barley, rye and/or triticale.

In the above-mentioned compositions or mixtures comprising a compound of formula (I) (in particular, one of the specific compounds disclosed herein, present either as a free compound and/or as an agrochemically acceptable salt thereof) with a safener, the weight ratio of the compound of formula (I) to the safener can vary over a large range and is, typically, from 200:1 to 1:200, especially from 50:1 to 1:50, more especially from 20:1 to 1:20, even more especially from 20:1 to 1:10. Preferably, the safener comprises (e.g. is) cloquintocet-mexyl, cloquintocet acid or an agrochemically acceptable salt thereof, mefenpyr-diethyl and/or isoxadifen-ethyl, and the weight ratio of the compound of formula (I) to the safener is from 20:1 to 1:10, more preferably from 15:1 to 1:2 (this can be, for example, for use on non-oat cereals). Typically, these weight ratios are measured as the free compound(s), i.e. excluding the weight of any associated salt counterion(s).

Application rates of herbicide (e.g. compound of formula (I)) and/or safener: The rate of application of safener relative to the compound of formula (I) is largely dependent upon the mode of application. In the case of field and/or soil and/or plant treatment (e.g. in a field or glasshouse): for example from 0.5 to 1000 g of safener per ha, or preferably from 1 to 250 g or from 2 to 200 g of safener per ha, are applied; and/or generally from 1 to 2000 g of compound of formula (I) per ha, or preferably from 5 to 500 g or from 10 to 400 g of compound of formula (I) per ha, are applied. ha=hectare. Typically, these application rates are measured as the free compound, i.e. excluding the weight of any associated salt counterion(s). In field and/or plant treatment, the application of the compound of formula (I) is preferably post-emergence.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. Ha=hectare. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

In one particular embodiment, the herbicidal composition or mixture comprising the compound of formula (I) and one or more further herbicides (e.g. as mentioned hereinabove) can be applied together with one of the safeners mentioned herein, e.g. hereinabove.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Tables A1, A2, A3 or P1 below, are usually drawn as an arbitrary single enol tautomer, but it should be inferred that this description covers both the diketone form and any possible enols which could arise through tautomerism. Where more than one tautomer is observed in proton NMR ($^1$H NMR), the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Abbreviations Used Herein

DCM-dichloromethane
DMF-N,N-dimethylformamide
DMSO-dimethyl sulfoxide
EDTA-ethylenediaminetetraacetic acid
Hunig's base-N,N-diisopropylethylamine
LDA-lithium diisopropylamide
LiHMDS-lithium hexamethyldisilazide, also called lithium 1,1,1,3,3,3-hexamethyldisilazan-2-ide, or lithium bis(trimethylsilyl)amide
PTFE-polytetrafluoroethylene
SPhos (S-Phos)-2-(dicyclohexylphosphino)-2',6'-dimethoxybiphenyl
TFA-trifluoroacetic acid
THF-tetrahydrofuran
RT-room temperature (typically ca. 15-30° C. such as ca. 18-25° C.)
HPLC-high performance (or high pressure) liquid chromatography
MS-mass spectrometry
NMR-nuclear magnetic resonance
within $^1$H NMR spectral data given herein: s=singlet, d=doublet, t=triplet, q=quartet, dd=doublet of doublets, m=multiplet, br.=broad
SFC-supercritical fluid chromatography Intermediate 1

Preparation of 3-methoxy-2-(2,4,6-trimethylphenyl)-cyclopent-2-en-1-one (previously described as Example 1 step 1 on pages 54-55 of WO 2010/000773 A1)

To a suspension of 2-bromo-3-methoxy-cyclopent-2-en-1-one (6.75 g, 35.3 mmol), 2,4,6-trimethylphenyl boronic acid (6.99 g, 42.6 mmol) and freshly ground potassium phosphate (15 g, 70.6 mmol) in degassed toluene (180 ml) under nitrogen are added Pd(OAc)$_2$ (159 mg, 0.71 mmol) and S-Phos (2-(dicyclohexylphosphino)-2',6'-dimethoxybiphenyl) (579 mg, 1.41 mmol), and the reaction heated to 90° C. with stirring under nitrogen for 4 hours. The reaction mixture is partitioned between ethyl acetate (150 ml) and water (150 ml), and the organic layer is removed, silica gel is added to the organic layer, the solvent is evaporated under reduced pressure and the residue is purified by flash chromatography on silica gel to give 3-methoxy-2-(2,4,6-trimethylphenyl)-cyclopent-2-en-1-one (6.2 g).

Intermediate 2

Synthesis of 5-(2-aminoethyl)-3-methoxy-2-(2,4,6-trimethylphenyl)cyclopent-2-en-1-one Step One: Synthesis of 2-nitroethyl trifluoromethanesulfonate To a stirred solution of 2-nitroethanol (4.88 ml, 68 mmol) in dichloromethane (200 ml) at 0° C. was added pyridine (11 ml, 136 mmol) followed by dropwise addition of trifluoromethanesulfonic anhydride. The colour of the reaction transitioned from pale pink through dark red to yellow during the addition of the anhydride. The reaction was allowed to warm to room temperature over three hours and then quenched by cautious addition of H$_2$O (200 ml). The phases were separated and the aqueous phase was extracted with further dichloromethane (2×100 ml). The combined organics were washed with saturated aqueous NH$_4$Cl solution (100 ml) and H$_2$O (100 ml), dried over MgSO$_4$, filtered and evaporated to dryness under reduced pressure to give the desired product (4.2 g, 28%) as a yellow/brown oil with was used in subsequent steps without additional purification. $^1$H NMR (400 MHz, CDCl$_3$) $\delta_H$ 5.00 (t, 2H), 4.75 (t, 2H). $^{19}$F NMR (375 MHz, CDCl$_3$) $\delta_F$ −74.1

Step Two: Synthesis of 3-methoxy-5-(2-nitroethyl)-2-(2,4,6-trimethylphenyl)cyclopent-2-en-1-one To a stirred solution of 3-methoxy-2-(2,4,6-trimethylphenyl)cyclopent-2-en-1-one (2.30 g, 10.0 mmol) (e.g. preparable by the method shown in Intermediate 1 herein, or preparable by method(s) disclosed in WO 2010/069834 A1 and/or WO 2011/073060 A2) in tetrahydrofuran (100 ml) at −78° C. under an atmosphere of N$_2$ was added dropwise lithium diisopropylamide (6.11 ml of a 1.8M solution in tetrahydrofuran/ethylbenzene/heptane, 11.0 mmol). The reaction was stirred at −78° C. for 105 minutes and then a solution of 2-nitroethyl trifluoromethanesulfonate (2.68 g, 12.0 mmol) in tetrahydrofuran (10 ml) was added dropwise. The reaction was stirred at −78° C. for 30 minutes and then allowed to warm to room temperature. The reaction was quenched cautiously with H$_2$O (200 ml) and extracted with EtOAc (3×100 ml). The combined organic extracts were washed with brine (50 ml), dried over MgSO$_4$, filtered and evaporated to dryness under reduced pressure to give a brown oil. The crude product was purified by silica gel chromatography using a 100% hexane to 100% EtOAc gradient to give the desired compound (780 mg, 26%) as a colourless oil.

$^1$H NMR (400 MHz, CDCl$_3$) $\delta$ 6.85 (s, 2H), 4.65 (t, 2H), 3.70 (s, 3H), 3.05 (dd, 1H), 2.75-2.65 (m, 1H) 2.55-2.40 (m, 2H), 2.30 (s, 3H), 2.30 (m, 1H), 2.05 (s, 6H).

Step Three: Synthesis of 5-(2-aminoethyl)-3-methoxy-2-(2,4,6-trimethylphenyl)cyclopent-2-en-1-one To a stirred solution of 3-methoxy-5-(2-nitroethyl)-2-(2,4,6-trimethylphenyl)cyclopent-2-en-1-one (108 mg, 0.356 mmol) in MeOH (10 ml) under an N$_2$ atmosphere was added ammonium formate (67 mg, 1.07 mmol) followed by 10% Pd/C (5 mg, catalytic). The reaction was heated at reflux for 1 hour, allowed to cool to room temperature and then filtered through a pad of celite, washing through with further MeOH (10 ml). The solvent was removed under reduced pressure to give the crude product (64 mg) which was used without further purification.

¹H NMR (400 MHz, CDCl₃) δ6.85 (s, 2H), 3.70 (s, 3H), 2.95 (dd, 1H), 2.90-2.75 (m, 2H), 2.75-2.65 (m, 1H), 2.50 (d, 1H), 2.25 (s, 3H), 2.10-2.05 (m, 1H), 2.05 (2×s, 2×3H), 1.65-1.55 (m, 1H).

Intermediate 2

Alternative synthesis of 5-(2-aminoethyl)-3-methoxy-2-(2,4,6-trimethylphenyl)cyclopent-2-en-1-one Step One: Synthesis of 1-nitroethylene To a flask equipped with distillation apparatus was added nitroethanol (60.0 g, 0.44 mol) and phthalic anhydride (146.38 g, 0.66 mol). The flask was evacuated to 110 mmbar and the receiver flask cooled with dry ice and acetone. The mixture was then heated to 130° C. After 1 hr at 130° C. the temperature was slowly increased to 180° C. over 2 hrs. Once the distillation was complete the heating was removed and the distillate was dissolved in 100 mL of anhydrous tetrahydrofuran, dried over anhydrous CaCl₂ and stored as a solution in tetrahydrofuran (33.34 g, 69%).
¹H NMR (400 MHz, CDCl₃) δ6.85-6.95 (br, 1H), 6.25-6.35 (br, 1H), 5.60-5.70 (br s, 1H).

Step two: Synthesis of 3-methoxy-5-(2-nitroethyl)-2-(2,4,6-trimethylphenyl)cyclopent-2-en-1-one To a solution of 3-methoxy-2-(2,4,6-trimethylphenyl)cyclopent-2-en-1-one (2.50 g, 10.86 mmol) in anhydrous tetrahydrofuran (25 mL) at −78° C. under an argon atmosphere was added dropwise lithium diisopropylamide (1.8M in tetrahydrofuran, 6.03 mL, 10.86 mmol) keeping the temperature below −50° C. Once the addition was complete the mixture was allowed to stir for 30 mins. A solution of the nitroethylene (2.38 mL, 10.86 mmol) in THF was then added dropwise over 1 hr using a dropping funnel. Once the addition was complete the mixture was stirred for 30 mins before being allowed to warm to room temperature. After stirring for 1 hr the reaction was quenched by the addition of water (50 mL) followed by saturated ammonium chloride solution (50 mL). The mixture was then extracted with ethyl acetate (3×20 mL). The combined organic extracts were dried, filtered and evaporated to dryness. The crude product was purified by silica gel chromatography using a hexane/ethyl acetate gradient to give the desired product (2.00 g, 60%) as a colourless oil. ¹H NMR (400 MHz, CDCl₃) δ6.85 (s, 2H), 4.65 (t, 2H), 3.70 (s, 3H), 3.05 (dd, 1H), 2.75-2.65 (m, 1H) 2.55-2.40 (m, 2H), 2.30 (s, 3H), 2.30 (m, 1H), 2.05 (s, 6H).

Step Three: Synthesis of 5-(2-aminoethyl)-3-methoxy-2-(2,4,6-trimethylphenyl)cyclopent-2-en-1-one To a solution of 3-methoxy-5-(2-nitroethyl)-2-(2,4,6-trimethylphenyl)cyclopent-2-en-1-one (2.00 g, 6.59 mmol) in MeOH (40.0 mL) was added ammonium formate (2.08 g, 32.96 mmol) followed by palladium on carbon (10%, 0.50 g). The mixture was then stirred for two hours and then filtered through a pad of celite and the filtrate was evaporated to dryness under reduced pressure. The residue was then dissolved in dichloromethane (20 mL) and washed with saturated sodium bicarbonate solution (2×10 mL). The organic phase was dried over magnesium sulphate, filtered and evaporated to dryness under reduced pressure to give the crude product (0.35 g, 19%) as a brown oil which was used without further purification. ¹H NMR (400 MHz, d4-methanol) 6.86-6.89 (s, 2H), 4.64-4.70 (t, 2H), 3.71-3.73 (s, 3H), 3.00-3.08 (m, 1H), 2.66-2.75 (m, 1H), 2.39-2.52 (m, 2H), 2.24-2.32 (m, 4H), 2.06-2.09 (d, 6H).

Intermediate 3

Preparation of 2-(4-Bromo-2,6-dimethyl-phenyl)-3-methoxy-cyclopent-2-en-1-one

Step 1: Preparation of ([4-bromo-2,6-dimethylphenyl]furan-2-yl)methanol (previously described in Example 1 step 1 on pages 51-52 of WO 2010/089210 A1)

4-Bromo-2,6-dimethyl-1-iodobenzene (5 g, 16 mmol) is dissolved in dry tetrahydrofuran (20 ml) and cooled to −78° C. under an atmosphere of dry nitrogen. Isopropylmagnesium chloride (2M solution in tetrahydrofuran, 10 ml, 20 mmol) is added dropwise with vigorous stirring over 30 minutes. When the addition is complete, the reaction is allowed to warm to room temperature and is stirred for 30 minutes at room temperature. The reaction mixture is cooled to −78° C. and a solution of 2-furaldehyde (2.4 g, 25 mmol) in dry tetrahydrofuran (10 ml) is added dropwise over 30 minutes. Once the addition is complete, the mixture is allowed to warm to room temperature and stirring was continued for 2 h. A solution of saturated aqueous ammonium chloride (30 ml) is added, and the mixture is extracted with dichloromethane (3×25 ml). The organic extracts are combined, washed with brine, dried over anhydrous magnesium sulfate, filtered and the filtrate is evaporated under reduced pressure. The residue is purified by chromatography on silica gel to give ([4-bromo-2,6-dimethylphenyl]furan-2-yl)methanol (3.71 g).

Step 2: Preparation of 5-(4-bromo-2,6-dimethylphenyl)-4-hydroxycyclopent-2-enone (previously described in Example 1 step 2 on page 52 of WO 2010/089210 A1)

Polyphosphoric acid (500 mg) is added to a warm (55° C.) solution of ([4-bromo-2,6-dimethylphenyl]furan-2-yl)methanol (843 mg, 3 mmol) in acetone (8 ml) and water (2 ml) and the mixture is heated at 55° C. for 24 hours. The mixture is cooled to room temperature and the acetone is removed under reduced pressure. The remaining mixture is partitioned between diethyl ether (20 ml) and water (20 ml). The aqueous phase is extracted with ether (2×50 ml), and then the organic phases are combined, washed with saturated aqueous sodium bicarbonate solution (20 ml), and brine (20 ml), dried over anhydrous magnesium sulfate, filtered and the filtrate is evaporated under reduced pressure. The residue is purified by chromatography on silica gel to give 5-(4-bromo-2,6-dimethylphenyl)-4-hydroxycyclopent-2-enone (596 mg).

Step 3: Preparation of 2-(4-bromo-2,6-dimethylphenyl)cyclopent-4-ene-1,3-dione (previously described in Example 1 step 3 on page 52 of WO 2010/089210 A1)

To a solution of 5-(4-bromo-2,6-dimethylphenyl)-4-hydroxycyclopent-2-enone (18.33 g. 65 mmol) in acetone (200 ml) at 0° C. is added, dropwise, a solution of Jones reagent (1.67 M, 39 ml, 65 mmol) and the resulting yellow solution is stirred at 0° C. for 90 minutes. The reaction is quenched by the addition of propan-2-ol (1 ml) and stirred for a further 2 hours. Brine (300 ml) is added and the reaction is extracted with ethyl acetate (3×250 ml). The organic extracts are combined, washed with brine, dried over anhydrous magnesium sulfate, filtered and the filtrate is concentrated under reduced pressure. The residue is purified by chromatography on silica gel to give 2-(4-bromo-2,6-dimethylphenyl)cyclopent-4-ene-1,3-dione (17.2 g).

Step 4: Preparation of 2-(4-Bromo-2,6-dimethyl-phenyl)cyclopentane-1,3-dione

To a solution of 2-(4-bromo-2,6-dimethylphenyl)cyclopent-4-ene-1,3-dione (50 g, 0.18 mol) in acetic acid (2000 ml) at 25-30° C. is added zinc powder (82.3 g, 1.26 mol). The resulting suspension is heated to 90° C. for 2 hours, followed by cooling to room temperature then filtration through a bed of diatomaceous earth. The residue is washed with methanol (100 ml×2) and the solution is concentrated in vacuo. Distilled water is added and the crude product is extracted with ethyl acetate (500 ml×3). Organic fractions are combined then washed with distilled water, brine, then dried over sodium sulfate, filtered and the filtrate is concentrated in vacuo to afford 2-(4-bromo-2,6-dimethylphenyl) cyclopentane-1,3-dione. This material is used directly in the next step without further purification.

Step 5: Preparation of 2-(4-Bromo-2,6-dimethyl-phenyl)-3-methoxy-cyclopent-2-en-1-one To a solution of 2-(4-bromo-2,6-dimethylphenyl)cyclopentane-1,3-dione (40 g, 0.143 mol) in acetone (2000 ml) is added anhydrous potassium carbonate (98.5 g, 0.714 mol) and iodomethane (45 ml, 0.72 mol). The resulting mixture is stirred at 25-30° C. for 16 hours, then volatile solvents are removed in vacuo, and the residue is diluted with distilled water (200 ml) and extracted with ethyl acetate (3×500 ml). Organic fractions are combined, washed with distilled water, brine, then dried over sodium sulphate, filtered and the filtrate concentrated in vacuo. The crude product is purified by silica gel chromatography to afford 2-(4-bromo-2,6-dimethyl-phenyl)-3-methoxy-cyclopent-2-en-1-one.

Example 1

Synthesis of N-[2-[2,4-dioxo-3-(2,4,6-trimethylphenyl)cyclopentyl]ethylcarbamoyl]pyridine-2-carboxamide (Compound A1)

To a solution of the pyridine-2-carboxamide (1.0 mmol, 0.12 g) in tetrahydrofuran (10 mL) was added the oxalyl chloride (1.1 mmol, 0.093 mL, 0.14 g). The mixture was heated in the microwave at 120° C. for 5 min. The 5-(2-aminoethyl)-3-methoxy-2-(2,4,6-trimethylphenyl)cyclopent-2-en-1-one (1.0 mmol, 0.27 g) was then added and the mixture heated for a further 5 min at 120° C., then Hunigs base (0.5 mL) was added. After stirring 1 h, the reaction was reduced in vacuo and purified by silica gel chromatography to afford N-[2-[4-methoxy-2-oxo-3-(2,4,6-trimethylphenyl) cyclopent-3-en-1-yl]ethylcarbamoyl]pyridine-2-carboxamide (0.17 mmol, 0.070 g).

The above material was dissolved in ethanol (2 mL) and 1M hydrochloric acid (2 mL) and the mixture heated to 60° C. for 4 h. The ethanol was removed in vacuo, the pH of the aqueous adjusted to 5 using saturated aqueous NaHCO$_3$ and the aqueous layer was extracted with chloroform. The combined organic layers were dried, filtered and reduced in vacuo to give N-[2-[4-hydroxy-2-oxo-3-(2,4,6-trimethylphenyl)cyclopent-3-en-1-yl]ethylcarbamoyl]pyridine-2-carboxamide (0.046 g, 0.11 mmol). 1H NMR (400 MHz, d4-methanol) 1.68-1.78 (1H, m), 2.03-2.08 (6H, s), 2.13-2.21 (1H, m), 2.22-2.26 (3H, s), 2.44-2.52 (1H, dd), 2.77-2.84 (1H, m), 2.88-2.97 (1H, dd) 3.48-3.54 (1H, dt), 6.83-6.87 (2H, s), 7.59-7.64 (1H, m), 7.97-8.03 (1H, dt), 8.16-8.22 (1H, d), 8.64-8.68 (1H, d).

Example 2

Synthesis of Compound A40

Step One: Synthesis of 2-[2-methoxy-4-oxo-3-(2,4,6-trimethylphenyl)cyclopent-2-en-1-yl]acetonitrile To a solution of 3-methoxy-2-(2,4,6-trimethylphenyl)cyclopent-2-en-1-one (intermediate 1, 43.420 mmol, 10.0 g) in THF (100 mL), under nitrogen at −78° C., LiHMDS (1M in THF, 47.762 mL, 47.762 mmol) was added dropwise. The temperature of the reaction was maintained below −55° C. during the dropwise addition of LiHMDS. After stirring for 15 minutes at −78° C., 2-bromoacetonitrile (52.1 mmol, 6.25 g, 3.63 mL) in THF (20 mL) was added over a period of 15 minutes. Stirring was continued at −78° C. for 40 minutes then the reaction was warmed to room temperature. After quenching the reaction with saturated ammonium chloride the solvent was removed under reduced pressure and the crude material was dissolved in dichloromethane and water. The phases were separated and the aqueous layer was extracted with dichloromethane. The combined organic layers were washed with water and brine then dried over MgSO$_4$ and the solvent was removed under reduced pressure to leave a brown oil. The crude material was purified by silica gel chromoatography (gradient elution: 0-100% ethyl acetate in hexane) to give the desired product (11.136 g, 95%) as a brown oil. $^1$H NMR (400 MHz, CDCl$_3$) δ6.88 (d, 2H), 3.57 (s, 3H), 3.14-3.32 (m, 1H), 2.88 (dd, 1H), 2.75-2.82 (m, 2H), 2.48 (dd, 1H), 2.23-2.34 (m, 3H), 2.14-2.22 (m, 3H), 2.06-2.14 (m, 3H).

Step Two: Synthesis of tert-butyl N-[2-[2-methoxy-4-oxo-3-(2,4,6-trimethylphenyl)cyclopent-2-en-1-yl] ethyl]carbamate To a solution of 2-[2-methoxy-4-oxo-3-(2,4,6-trimethylphenyl)cyclopent-2-en-1-yl]acetonitrile (3.713 mmol, 1.00 g) in methanol (28 mL) under nitrogen was added tert-butoxycarbonyl tert-butyl carbonate (7.43 mmol, 1.62 g) and nickel (II) chloride (0.668 mmol, 0.0867 g). The mixture was cooled to −5° C. in an acetone/dry ice bath before the sodium borohydride (22.28 mmol, 0.8601 g) was added portionwise over 30 minutes. After stirring for 1 hour at −5° C. the reaction was allowed to warm to room temperature then stirred for a further 3.5' hours. N'-(2-aminoethyl)ethane-1,2-diamine (3.713 mmol, 0.3909 g, 0.409 mL) was added and the mixture left to stir at room temperature for 1 hour. After diluting with saturated sodium bicarbonate and ethyl acetate, the phases were separated and the aqueous layer was extracted with ethyl acetate. The combined organic layers were washed with water and brine then dried over MgSO$_4$ and the solvent was removed under reduced pressure to leave a brown oil. The crude material was purified by silica gel chromoatography (gradient elution: 0-75% ethyl acetate in hexane) to give the desired product (1.167 g, 84%) as a colourless oil. $^1$H NMR (400 MHz, CDCl$_3$) δ6.78-6.95 (m, 2H), 4.60 (br. s., 1H), 3.44-3.63 (m, 3H), 3.14-3.36 (m, 2H), 2.86-3.04 (m, 1H), 2.68-2.85 (m, 1H), 2.22-2.37 (m, 4H), 2.01-2.16 (m, 6H), 1.36-1.71 (m, 10H).

Step Three: Synthesis of 2-[2,4-dioxo-3-(2,4,6-trimethylphenyl)cyclopentyl]ethylammonium chloride To a solution of tert-butyl N-[2-[4-methoxy-2-oxo-3-(2,4,6-trimethylphenyl)cyclopent-3-en-1-yl]ethyl]carbamate (2.14 mmol, 0.800 g) in acetone (30 mL) was added Hydrochloric acid (2M, 40 mmol, 20 mL). The mixture was heated to 70° C. for 3 h and then the mixture was concentrated in vacuo to give the desired product as a a white solid. 1H NMR (400 MHz, DMSO-d6) δ1.54-1.78 (m, 1H) 1.80-2.12 (m, 8H) 2.16-2.42 (m, 5H) 2.67 (br. s., 1H) 2.76-3.01 (m, 3H) 6.83 (s, 2H) 7.91 (br. s., 3H)

Step Four: Synthesis of N-[2-[2,4-dioxo-3-(2,4,6-trimethylphenyl)cyclopentyl]ethyl]-5,5-dimethyl-4H-isoxazole-3-carboxamide The 4-(2-aminoethyl)-2-(2,4,6-trimethylphenyl)cyclopentane-1,3-dione hydrochloride (0.541 mmol, 0.160 g) was suspended in dichloromethane (10 mL) then (2,3,4,5,6-pentafluorophenyl) 5,5-dimethyl-4H-isoxazole-3-carboxylate (0.595 mmol, 0.184 g) was added followed by the N,N-diethylethanamine (1.62 mmol, 0.164 g, 0.226 mL). After stirring for 1.5 h, the reaction mixture was acidified with 2M HCl and the organic layer was concentratd in vacuo and the crude product was purified by silica gel chromatography (gradient elution: 0-100% ethyl acetate in hexane) to give the desired product as colourless oil (0.186 g). 1H NMR (400 MHz, CDCl$_3$) δ=7.43-7.29 (m, 1H), 6.82 (s, 2H), 3.63-3.22 (m, 2H), 2.93 (s, 2H), 2.82-2.59 (m, 2H), 2.29-2.11 (m, 4H), 2.10-1.63 (m, 8H), 1.43 (d, 6H)

Example 3

Synthesis of Compound A43

Step One: Synthesis of 2-[4-(4-chloropyrazol-1-yl)-2,6-dimethyl-phenyl]-3-methoxy-cyclopent-2-en-1-one A flask charged with 2-(4-bromo-2,6-dimethyl-phenyl)-3-methoxy-cyclopent-2-en-1-one (2 g, 6.7755 mmol), 4-chloro-1H-pyrazole (1.39 g, 13.551 mmol), potassium carbonate (2.83 g, 20.3265 mmol) and copper (I) Iodide (0.658 g, 3.3878 mmol) was evacuated and purged with nitrogen. Chlorobenzene (10 mL) was added, followed by N,N'-dimethylethylene diamine (0.737 mL, 6.775 mmol), and the reaction was refluxed (131° C.) for 1 hour. The reaction was allowed to cool to ambient temperature, diluted with chloroform (25 mL) and washed with saturated aqueous ammonium chloride (25 mL). The aqueous layer was acidified to pH 5 with 2N HCl and re-extracted with chloroform. The combined organic layers were filtered through a PTFE frit, concentrated in vacuo and diluted with acetone (10 mL). Potassium carbonate (1.89 g, 13.55 mmol) and iodomethane (0.844 mL, 13.55 mmol) were added to the above solution, and the reaction was stirred for 4 hours at ambient temperature. The reaction was diluted with chloroform (25 mL), washed with saturated aqueous ammonium chloride (25 mL) and filtered through a PTFE frit. The filtrate was dry loaded onto silica, purified by silica gel chromatography (gradient elution: 20-100% EtOAc in hexane) to give 2-[4-(4-chloropyrazol-1-yl)-2,6-dimethyl-phenyl]-3-methoxy-cyclopent-2-en-1-one (1.61 g, 5.08 mmol, 75.0% Yield) as a white solid. $^1$H NMR (400 MHz, CDCl$_3$) δ7.87 (s, 1H), 7.61 (s, 1H), 7.34 (s, 2H), 3.78 (s, 3H), 2.93-2.79 (m, 2H), 2.73-2.61 (m, 2H), 2.20 (s, 6H).

Step Two: Synthesis of 2-[3-[4-(4-chloropyrazol-1-yl)-2,6-dimethyl-phenyl]-2-methoxy-4-oxo-cyclopent-2-en-1-yl]acetonitrile An oven-dried 3-neck flask was charged with 2-[4-(4-chloropyrazol-1-yl)-2,6-dimethyl-phenyl]-3-methoxy-cyclopent-2-en-1-one (869 mg, 2.74 mmol), purged with nitrogen, and THF (8.69 mL) was added. The reaction is cooled to −65° C. and LiHMDS (1M in THF, 3.01 mL, 3.01 mmol) was added dropwise over a period of 2 minutes and the reaction was allowed to stir for 20 minutes. A solution of 2-bromoacetonitrile (395 mg, 3.2918 mmol) in THF (1.738 mL) was then added dropwise, and the reaction was allowed to stir for a further 60 minutes, before being allowed to warm to ambient temperature over a period of 40 minutes. The reaction was quenched by the addition of saturated aqueous ammonium chloride solution (25 ml) and the reaction was allowed to stir for a further 10 minutes. The reaction was extracted with EtOAc (2×25 mL). The combined organic layers were filtered through a PTFE frit, dry loaded onto silica and purified by silica gel chromatography (0-100% EtOAc in hexane) to give 2-[3-[4-(4-chloropyrazol-1-yl)-2,6-dimethyl-phenyl]-4-methoxy-2-oxo-cyclopent-3-en-1-yl]acetonitrile (854 mg, 2.40 mmol, 87.5% yield) as a beige solid. $^1$H NMR (400 MHz, CDCl$_3$) δ2.21 (s, 3H), 2.30 (s, 3H), 2.52 (dd, 1H), 2.76-2.95 (m, 3H), 3.28 (dd, 1H), 3.60 (s, 3H), 7.36 (s, 2H), 7.62 (s, 1H), 7.89 (s, 1H).

Step Three: Synthesis of tert-butyl N-[2-[3-[4-(4-chloropyrazol-1-yl)-2,6-dimethyl-phenyl]-2-methoxy-4-oxo-cyclopent-2-en-1-yl]ethyl]carbamate Prepared from 2-[3-[4-(4-chloropyrazol-1-yl)-2,6-dimethyl-phenyl]-2-methoxy-4-oxo-cyclopent-2-en-1-yl]acetonitrile according to substantially the same procedure used to prepare A44 (step 2) to give the desired product (194 mg, 30%) as a pale yellow gum. $^1$H NMR (500 MHz, CDCl$_3$ and a few drops of d4-methanol) δ7.88 (m, 1H), 7.62 (s, 1H), 7.34 (s, 2H), 4.59-4.75 (m, 1H), 3.57 (s, 5H), 3.03-3.19 (m, 1H), 2.65-2.80 (m, 1H), 2.33-2.48 (m, 1H), 2.22 (d, 6H), 1.45 (s, 10H).

Step Four: Synthesis of 2-[3-[4-(4-chloropyrazol-1-yl)-2,6-dimethyl-phenyl]-2,4-dioxo-cyclopentyl]ethylammonium chloride To a solution of tert-butyl N-[2-[3-[4-(4-chloropyrazol-1-yl)-2,6-dimethyl-phenyl]-2-methoxy-4-oxo-cyclopent-2-en-1-yl]ethyl]carbamate (0.100 g, 0.224 mmol) in acetone (2 mL) was added 2M HCl (2 mL). The reaction mixture was heated to 120° C. under microwave irradiation for 20 minutes after which it was diluted with dichloromethane and the phases were separated. The aqueous phase was evaporated to dryness to give the desired product (0.085 g, 99%) as an off white glass. $^1$H NMR (500 MHz, D$_2$O) δ7.89 (s, 1H), 7.58 (s, 1H), 7.09 (m, 2H), 3.11 (m, 2H), 3.00 (m, 1H), 2.88 (m, 1H), 2.50 (m, 1H), 2.11 (m, 1H), 1.99 (s, 6H), 1.86 (m, 1H).

Note: The above-shown HCl salt of the amine (R—NH$_3^+$ Cl$^-$), produced in the above process, can be converted to the corresponding free amine (R—NH$_2$) if desired, e.g. via an ion exchange column.

Step Five: Synthesis of of Compound A43

The 2-[3-[4-(4-chloropyrazol-1-yl)-2,6-dimethyl-phenyl]-2,4-dioxo-cyclopentyl]ethylammonium chloride (0.523 mmol, 0.200 g) was suspended in dichloromethane (10 mL) then the (2,3,4,5,6-pentafluorophenyl) 5,5-dimethyl-4H-isoxazole-3-carboxylate (0.575 mmol, 0.178 g) was added followed by the N,N-diethylethanamine (1.57 mmol, 0.159 g, 0.219 mL). On stirring at room temperature the solid all gradually dissolved. After stirring for 2 hours, the reaction mixture was washed with 2M HCl, the organic layer was concentrated in vacuo and purified by silica gel chromatography (gradient elution: 0-100% ethyl acetate in hexane) to give the desired product as a white foam (0.190 g). 1H NMR (400 MHz, CDCl$_3$) δ=7.83 (s, 1H), 7.57 (s, 1H), 7.46-7.33 (m, 1H), 7.22 (s, 2H), 3.41 (s, 2H), 2.96 (s, 2H), 2.90-2.68 (m, 2H), 2.33-2.20 (m, 1H), 2.16-1.88 (m, 7H), 1.87-1.67 (m, 1H), 1.44 (s, 6H)

Example 4

Synthesis of Compound A36

Step One: Synthesis of 2-[2-methoxy-4-oxo-3-(2,4,6-trimethylphenyl)cyclopent-2-en-1-yl]ethylammonium chloride To a solution of tert-butyl N-[2-[2-methoxy-4-oxo-3-(2,4,6-trimethylphenyl)cyclopent-2-en-1-yl]ethyl]carbamate (15.06 mmol, 5.624 g) in dichloromethane (30 mL) at room temperature was added hydrogen chloride (4M in 1,4-dioxane, 40 mmol, 10 mL). After stirring at room temperature for 4 hours the solvent was removed to leave an off white solid which was carried on directly to the next stage of the synthesis.

Step Two: Synthesis of 4-[2-[[3-chloro-5-(trifluoromethyl)-2-pyridyl]amino]ethyl]-3-methoxy-2-(2,4,6-trimethylphenyl)cyclopent-2-en-1-one 2-[2-methoxy-4-oxo-3-(2,4,6-trimethylphenyl)cyclopent-2-en-1-yl]ethylammonium chloride (0.100 g, 0.323 mmol), 3-chloro-2-fluoro-5-(trifluoromethyl)pyridine (0.323 mmol) and potassium carbonate (0.403 mmol) were suspended in acetonitrile (3 mL) and the reaction mixture was heated at reflux for 5 hours. After cooling the reaction to room temperature, the mixture was diluted with 2M HCl to pH 7 and extracted with EtOAc. The organic phase was dried and concentrated in vacuo and purified by silica gel chromatography (gradient elution: 5% EtOAc in iso-hexane to 100% EtOAc) to give the desired product as a gum (0.056 g, 0.12 mmol). 1H NMR (400 MHz, CDCl$_3$) δ8.29 (d, 1H), 7.66-7.62 (m, 1H), 6.86 (s, 2H), 5.49 (t, 1H), 3.73-3.63 (m, 2H), 3.57-3.45 (m, 3H), 2.99 (dddd, 1H), 2.81 (dd, 1H), 2.39 (dd, 1H), 2.28-2.21 (m, 4H), 2.15-2.08 (m, 6H), 1.84-1.68 (m, 1H)

Step Three: Synthesis of Compound A36

4-[2-[[3-chloro-5-(trifluoromethyl)-2-pyridyl]amino]ethyl]-3-methoxy-2-(2,4,6-trimethylphenyl)cyclopent-2-en-1-one (0.056 g, 0.12 mmol) was dissolved in acetone (5.89 mL/mmol) and hydrochloric acid (2M) (5.89 mL/mmol, 1.5 mmol) was added.

The reaction mixture was heated to 60° C. and allowed to stir for 5.5 hours. The mixture was coiled down, concentrated in vacuo to remove the acetone and the resulting aqueous layer was neutralized to pH 7 by the addition of aqueous potassium hydroxide. The aqueous layer was extracted with EtOAc and the organic layers were dried and concentrated in vacuo to to give the desired product as a white glassy solid (0.0505 g, 0.115 mmol). 1H NMR (400 MHz, d4-methanol) δ8.33-8.23 (m, 1H), 8.20-8.08 (m, 1H), 6.88 (s, 2H), 3.86-3.77 (m, 1H), 3.74-3.67 (m, 1H), 3.02 (dd, 1H), 2.90-2.79 (m, 1H), 2.56-2.43 (m, 1H), 2.26 (s, 3H), 2.15 (qd, 1H), 2.09-2.03 (m, 6H), 2.00-1.89 (m, 1H)

Example 5

Synthesis of Compound A9

Step One: Syntheis of phenyl N-[2-[2-methoxy-4-oxo-3-(2,4,6-trimethylphenyl)cyclopent-2-en-1-yl]ethyl]carbamate 2-[2-methoxy-4-oxo-3-(2,4,6-trimethylphenyl)cyclopent-2-en-1-yl]ethylammonium chloride (2.724 mmoll) was taken up into dichloromethane (15 mL). Pyridine (3.541 mmol) was added followed by addition of phenyl chloroformate (3.269 mmol). The reaction mixture was stirred for 2 hours then a further 0.5 eq of phenyl chloroformate was added. After stirring for 1 hour, a further 1 eq of pyridine was added and stirring continued for 1 hour. The reaction mixture was left to stand over night. The reaction mixture was diluted with DCM and then quenched with water. The reaction mixture was extracted with DCM and the organic layers were dried with MgSO$_4$, concentrated in vacuo and purified by silica gel chromatography (gradient elution: 5% EtOAc in iso-hexane to 100% EtOAc) to give the desire product as a yellow gum (0.485 g, 1.23 mmol). 1H NMR (400 MHz, CDCl$_3$) δ7.40-7.32 (m, 2H), 7.24-7.17 (m, 1H), 7.13 (d, 2H), 6.86 (s, 2H), 5.14 (br. s., 1H), 3.58-3.50 (m, 3H), 3.42 (q, 2H), 2.99 (br. s., 1H), 2.81 (dd, 1H), 2.32 (dd, 1H), 2.28-2.22 (m, 3H), 2.23-2.16 (m, 3H), 2.11 (s, 6H), 1.80-1.68 (m, 1H)

Step Two: Synthesis of 1-[2-[2-methoxy-4-oxo-3-(2,4,6-trimethylphenyl)cyclopent-2-en-1-yl]ethyl]-3-phenyl-urea Phenyl N-[2-[2-methoxy-4-oxo-3-(2,4,6-trimethylphenyl)cyclopent-2-en-1-yl]ethyl]carbamate (0.4025 mmol) was taken up into acetonitrile (2 mL) and placed in a microwave vial. N,N-diethylethanamine (0.4025 mmol) was added followed by aniline (0.8050 mmol). The reaction mixture was heated at 86° C. for 90 min. The reaction mixture was diluted with EtOAc and washed with 2M HCl. The aqueous layer was extracted with EtOAc, the organic layers were concentrated invacuo and purified by silica gel chromatography (gradient elution: 5% EtOAc in iso-hexane to 100% EtOAc) to give the desired product (0.0677 g, 0.172 mmol). 1H NMR (400 MHz, CDCl$_3$) δ7.31-7.21 (m, 4H), 7.09-7.00 (m, 1H), 6.91 (s, 1H), 6.85 (s, 2H), 5.25 (t, 1H), 3.52-3.46 (m, 2H), 3.36-3.25 (m, 1H), 2.95-2.86 (m, 1H), 2.77 (dd, 1H), 2.30 (dd, 1H), 2.25 (s, 2H), 2.18-2.11 (m, 1H), 2.08 (d, 4H), 1.54 (tdd, 1H)

Step Three: Synthesis of 1-[2-[2,4-dioxo-3-(2,4,6-trimethylphenyl)cyclopentyl]ethyl]-3-phenyl-urea 1-[2-[2-methoxy-4-oxo-3-(2,4,6-trimethylphenyl)cyclopent-2-en-1-yl]ethyl]-3-phenyl-urea (0.086 g, 0.22 mmol) was dissolved in acetone (5.89 mL/mmol) and hydrochloric acid (2M, 5.89 mL/mmol, 2.6 mmol) was added. The reaction mixture was heated to 60° C. for 8 hours. The reaction mixture was allowed to cool over the weekend during which time a pale solid crashed out of solution. This solid was collected by filtration and washed with water, dried to give the desired product as a white powder (0.0544 g, 0.144 mmol). 1H NMR (400 MHz, $d_4$-methanol) δ=7.38-7.31 (m, 2H), 7.27-7.18 (m, 2H), 7.00-6.92 (m, 1H), 6.86 (s, 2H), 3.42-3.33 (m, 2H), 2.95-2.75 (m, 2H), 2.48-2.41 (m, 1H), 2.25 (s, 3H), 2.12-2.06 (m, 1H), 2.05 (s, 6H), 1.66 (qd, 1H)

Example 6

Synthesis of Compound A73

To a solution of 5-(2-aminoethyl)-3-methoxy-2-(2,4,6-trimethylphenyl)cyclopent-2-en-1-one (0.100 g, 0.366 mmol, 100 mg) in dichloromethane (1 mL) was added Hunig's base (0.402 mmol, 69 µL, 52 mg) followed by 4-fluorobenzenesulfonyl chloride (0.366 mmol). The mixture was stirred for 4 h and a further 1 eq of 4-fluorobenzenesulfonyl chloride was added then the mixture was stirred for a further 4 h. The reaction was worked up by dilution with DCM and washing with 2M HCl. The combined organic layer was dried of $MgSO_4$, filtered and concentrated in vacuo. The resulting residue was purified by preparative HPLC to give the desired sulfonamide, which was dissolved in ethanol (2 mL) and aqueous hydrochloric acid (2M, 2 mL). The reaction mixture was heated to 60° C. for 4 h, cooled to room temperature and then concentrated in vacuo to give the desired product (29.4 mg). 1H NMR (400 MHz, d4-methanol) 8.05 (d, 2H), 7.89 (d, 2H), 6.84 (br. s., 2H), 3.04 (t, 2H), 2.88-2.66 (m, 2H), 2.30 (dd, 1H), 2.23 (s, 3H), 2.07-1.90 (m, 7H), 1.58 (qd, 1H)

Example 7

Preparation of 1-[2-[2,4-dioxo-3-(2,4,6-trimethylphenyl)cyclopentyl]ethyl]-3-[4-(trifluoromethyl)-2-pyridyl]urea (Compound A2)

Step 1: Preparation of phenyl N-[4-(trifluoromethyl)-2-pyridyl]carbamate

To a solution of 4-(trifluoromethyl)pyridin-2-amine (10 g) in dichloromethane (100 mL) was added pyridine (6.49 mL). The solution was cooled with an ice water bath and phenyl chloroformate (9.286 mL) was added drop-wise, taking care to keep the internal reaction temperature below 5° C. Further dichloromethane (20 mL) was added to improve stirring. The reaction mixture was allowed to warm to room temperature and then stirred for 40 minutes. The reaction mixture was partitioned between water and dichloromethane (100 mL), and then extracted with further dichloromethane (100 mL). The organic layers were dried over anhydrous sodium sulfate and concentrated to give phenyl N-[4-(trifluoromethyl)-2-pyridyl]carbamate (18.92 g). $^1$H NMR (400 MHz, $CDCl_3$) δ9.33 (br s, 1H), 8.55 (d, 1H), 8.37 (s, 1H), 7.45 (m, 2H), 7.22-7.33 (m, 4H)

Step 2: Preparation of 1-[2-[4-methoxy-2-oxo-3-(2,4,6-trimethylphenyl)cyclopent-3-en-1-yl]ethyl]-3-[4-(trifluoromethyl)-2-pyridyl]urea To a suspension of 5-(2-aminoethyl)-3-methoxy-2-(2,4,6-trimethylphenyl)cyclopent-2-en-1-one hydrochloride (0.100 g) and phenyl N-[4-(trifluoromethyl)-2-pyridyl]carbamate (Intermediate 2, 0.100 g) in dichloromethane (2.5 mL) was added diisopropylethylamine (0.09 mL). The mixture was stirred for 4 hours and then partitioned with 2M hydrochloric acid. The aqueous phase was extracted with further dichloromethane (×2). The combined organics were dried with magnesium sulfate, concentrated and purified by chromatography on silica to give 1-[2-]4-methoxy-2-oxo-3-(2,4,6-trimethylphenyl)cyclopent-3-en-1-yl]ethyl]-3-[4-(trifluoromethyl)-2-pyridyl]urea as a white solid (0.066 g). $^1$H NMR (400 MHz, $CDCl_3$) δ9.28 (brs, 1H) 8.94 (s, 1H) 8.35 (d, 1H) 7.04-7.10 (m, 1H) 6.86 (s, 1H) 3.48-3.59 (m, 5H) 2.95-3.06 (m, 1H) 2.82 (dd, 1H) 2.36-2.43 (m, 1H) 2.25-2.32 (m, 4H) 2.11 (d, 6H) 1.67-1.81 (m, 1H)

Step 3: Preparation of 1-[2-[2,4-dioxo-3-(2,4,6-trimethylphenyl)cyclopentyl]ethyl]-3-[4-(trifluoromethyl)-2-pyridyl]urea A solution of 1-[2-[4-methoxy-2-oxo-3-(2,4,6-trimethylphenyl)cyclopent-3-en-1-yl]ethyl]-3-[4-(trifluoromethyl)-2-pyridyl]urea (0.052 g) in acetone (0.66 mL) and 2M hydrochloric acid (0.66 mL) was heated to 60° C. for 4 hours. Upon cooling the mixture was concentrated to remove the acetone and the aqueous residue was extracted with ethyl acetate. The solid was suspended in the organic phase so the biphasic solution was filtered and a white solid collected. The organic phase was dried over anhydrous magnesium sulfate and concentrated to give a second white solid. Both solids collected were the desired compound and so were combined and triturated with ether to give 1-[2-[2,4-dioxo-3-(2,4,6-trimethylphenyl)cyclopentyl]ethyl]-3-[4-(trifluoromethyl)-2-pyridyl]urea as a white solid.

$^1$H NMR (400 MHz, $CD_3OD$) δ8.36-8.47 (m, 1H), 7.60 (s, 1H), 7.42 (d, 1H), 6.88 (s, 2H), 3.47-3.56 (m, 2H), 2.97 (dd, 1H), 2.77-2.89 (m, 1H), 2.50 (dd, 1H), 2.27 (s, 3H), 2.17 (d, 1H), 2.00-2.10 (m, 6H), 1.69-1.82 (m, 1H)

Example 8

Preparation of 1-[2-[2,4-dioxo-3-(2,4,6-trimethylphenyl)cyclopentyl]ethyl]-3-phenyl-thiourea (Compound A90)

Step 1: Preparation of 1-[2-[4-methoxy-2-oxo-3-(2,4,6-trimethylphenyl)cyclopent-3-en-1-yl]ethyl]-3-phenyl-thiourea To a solution of 5-(2-aminoethyl)-3-methoxy-2-(2,4,6-trimethylphenyl)cyclopent-2-en-1-one (Intermediate 2, 0.100 g) in chloroform (1 mL) was added the phenyl isothiocyanate (0.049 g) and the mixture stirred for 4 hours. The reaction was partitioned between DCM and 2M hydrochloric acid. The organic layer was dried over anhydrous sodium sulfate and concentrated to give crude 1-[2-[4-methoxy-2-oxo-3-(2,4,6-trimethylphenyl)cyclopent-3-en-1-yl]ethyl]-3-phenyl-thiourea.

Step 2: Preparation of 1-[2-[2,4-dioxo-3-(2,4,6-trimethylphenyl)cyclopentyl]ethyl]-3-phenyl-thiourea The crude 1-[2-[4-methoxy-2-oxo-3-(2,4,6-trimethylphenyl)cyclopent-3-en-1-yl]ethyl]-3-phenyl-thiourea from Step 1 was dissolved in ethanol (2 mL) and 1M hydrochloric acid (2 mL) and the mixture heated to 60° C. for 4 hours. The reaction mixture was concentrated and purified by chromatography on silica to give 1-[2-[2,4-dioxo-3-(2,4,6-trimethylphenyl)cyclopentyl]ethyl]-3-phenyl-thiourea (0.055 g).

$^1$H NMR (400 MHz, CD$_3$OD) δ7.29-7.42 (m, 3H) 7.14-7.23 (m, 2H) 6.86 (s, 2H) 3.66-3.80 (m, 2H) 2.88-2.99 (m, 1H) 2.70-2.82 (m, 1H) 2.56 (d, 1H) 2.24 (s, 3H) 1.99-2.20 (m, 7H) 1.68-1.81 (m, 1H)

Example 9

Preparation of 4-[2-[(5-bromopyrimidin-2-yl)amino]ethyl]-2-(2,4,6-trimethylphenyl)cyclopentane-1,3-dione (Compound A126)

Step 1: Preparation of 4-[2-[(5-bromopyrimidin-2-yl)amino]ethyl]-2-(2,4,6-trimethylphenyl)cyclopentane-1,3-dione A flask was charged with 4-(2-aminoethyl)-2-(2,4,6-trimethylphenyl)cyclopentane-1,3-dione hydrochloride (0.250 g, 0.845 mmol) was dissolved in 1,4-dioxane (3 mL) and N,N-diethylethanamine (0.930 mmol) was added. After stirring for 2 mins, cesium carbonate (2.54 mmol), 5-bromo-2-iodo-pyrimidine (0.845 mmol), (5-diphenylphosphanyl-9,9-dimethyl-xanthen-4-yl)-diphenyl-phosphane (0.127 mmol) and tris(dibenzylideneacetone)dipalladium(0) (0.0423 mmol) were added. The reaction mixture was heated at 90° C. for 3.5 hours then cooled to room temperature. The soluction was diluted with 2M HCl and extracted twice with EtOAc. The organic layers were dried (MgSO$_4$) and concentrated in vacuo to leave an orange oil which was purified by flash column chromatography using a gradient elution from DCM to 10% MeOH in DCM to furnish 4-[2-[(5-bromopyrimidin-2-yl)amino]ethyl]-2-(2,4,6-trimethylphenyl)cyclopentane-1,3-dione (0.074 g, 0.18 mmol, 21% yield).

1H NMR (400 MHz, CD$_3$OD) 8.30 (s, 2H), 6.92-6.74 (m, 2H), 3.56-3.43 (m, 2H), 2.95-2.85 (m, 1H), 2.79 (br. s., 1H), 2.46 (dd, 17.7 Hz, 1H), 2.24 (s, 3H), 2.22-2.10 (m, 1H), 2.04 (d, 6H), 1.76-1.63 (m, 1H)

Example 10

Preparation of 1-[2-[2,4-dioxo-3-(2,4,6-trimethylphenyl)cyclopentyl]ethyl]-1-methyl-3-(2-pyridyl)urea (Compound A101)

Step 1: Preparation of tert-butyl N-[2-[4-methoxy-2-oxo-3-(2,4,6-trimethylphenyl)cyclopent-3-en-1-yl]ethyl]-N-methyl-carbamate tert-Butyl N-[2-[4-methoxy-2-oxo-3-(2,4,6-trimethylphenyl)cyclopent-3-en-1-yl]ethyl]carbamate (0.20600 g, 0.5515 mmol) was dissolved in DMF (8 mL) and iodomethane (0.8273 mmol) and sodium hydride (60% dispersion in mineral oil, 0.8273 mmol) were added. The reaction mixture was stirred at room temperature for 3 hour, then quenched by the addition of saturated sodium bicarbonate solution. The mixture was extracted twice with diethyl-ether and the combined organic layers were washed with water, dried (MgSO$_4$) and concentrated in vacuo to leave a yellow oil. The resulting residue was purified by flash column chromatography using a gradient elution from 5% EtOAc in i-hexane to 100% EtOAc to furnish tert-butyl N-[2-[4-methoxy-2-oxo-3-(2,4,6-trimethylphenyl)cyclopent-3-en-1-yl]ethyl]-N-methyl-carbamate (0.177 g, 0.457 mmol, 83% yield).

1H NMR (400 MHz, CDCl$_3$) 6.91-6.78 (m, 2H), 3.53 (s, 3H), 3.46-3.21 (m, 2H), 2.88 (s, 4H), 2.80-2.68 (m, 1H), 2.31 (s, 1H), 2.30-2.24 (m, 3H), 2.24-2.13 (m, 1H), 2.13-2.07 (m, 6H), 1.55 (s, 1H), 1.47 (s, 9H)

Step 2: Preparation of 1-[2-[4-methoxy-2-oxo-3-(2,4,6-trimethylphenyl)cyclopent-3-en-1-yl]ethyl]-1-methyl-3-(2-pyridy)urea tert-Butyl N-[2-[4-methoxy-2-oxo-3-(2,4,6-trimethylphenyl)cyclopent-3-en-1-yl]ethyl]-N-methyl-carbamate (0.102 g, 0.263 mmol) was stirred for 2 hours at room temperature in hydrogen chloride (4M in 1,4 Dioxane, 2 mL, 8 mmol). The reaction mixture was concentrated in vacuo to leave a yellow gum which was taken up in dichloromethane (2 mL) and phenyl N-(2-pyridyl)carbamate (0.316 mmol) was added followed by N,N-diethylethanamine (0.526 mmol). After stirring at room temperature for 1.5 hours, the reaction mixture was heated at reflux for 2.5 hours. The reaction mixture was cooled to room temperature, diluted with 2M HCl and extracted twice with DCM. The organic layers were dried (MgSO$_4$) and concentrated in vacuo to leave an orange gum which was purified by flash column chromatography using a gradient elution from 5% EtOAc in i-hexane to 100% EtOAc to furnish 1-[2-[4-methoxy-2-oxo-3-(2,4,6-trimethylphenyl)cyclopent-3-en-1-yl]ethyl]-1-methyl-3-(2-pyridy)urea (0.0906 g, 0.222 mmol, 84% yield).

1H NMR (400 MHz, CDCl$_3$) 8.19 (d, 1H), 8.06 (d, 1H), 7.68-7.55 (m, 1H), 7.24 (br. s., 1H), 6.99-6.91 (m, 1H), 6.86 (s, 2H), 3.61-3.43 (m, 5H), 3.12-3.03 (m, 3H), 2.94 (br. s., 1H), 2.87-2.76 (m, 1H), 2.33 (dd, 1H), 2.27-2.20 (m, 4H), 2.10 (s, 6H), 1.78-1.64 (m, 1H)

Step 3: Preparation of 1-[2-[2,4-dioxo-3-(2,4,6-trimethylphenyl)cyclopentyl]ethyl]-1-methyl-3-(2-pyridy)urea 1-[2-[4-Methoxy-2-oxo-3-(2,4,6-trimethylphenyl)cyclopent-3-en-1-yl]ethyl]-1-methyl-3-(2-pyridy)urea (0.090 g, 0.22 mmol) was dissolved in acetone (5.89 mL/mmol) and hydrochloric acid (2M solution, 5.89 mL/mmol, 2.6 mmol) was added. The reaction mixture was heated to 60° C. for 4 hours. The reaction mixture was concentrated in vacuo to furnish 1-[2-[2,4-dioxo-3-(2,4,6-trimethylphenyl)cyclopentyl]ethyl]-1-methyl-3-(2-pyridy)urea (0.0860 g, 0.219 mmol, 99% yield).

1H NMR (400 MHz, CDCl$_3$) 8.26 (d, 2H), 7.57 (d, 1H), 7.41 (t, 1H), 6.89 (s, 2H), 3.22-2.98 (m, 5H), 2.83 (d, 1H), 2.48 (d, 1H), 2.32-2.23 (m, 4H), 2.13 (d, 8H),

Example 11

1-[2-[2,4-dioxo-3-(2,4,6-trimethylphenyl)cyclopentyl]ethyl]-3-methyl-urea (Compound A94)

Step 1: Preparation of (2,3,4,5,6-pentafluorophenyl) phenyl carbonate 2,3,4,5,6-Pentafluorophenol (3.000 g, 16.30 mmol) was dissolved in dichloromethane (10 mL) and pyridine (21.19 mmol) was added followed by drop-wise addition of phenyl carbonochloridate (19.56 mmol) in dichloromethane (10 mL) over 10 mins. The reaction mixture was stirred for 2 hours, then diluted with DCM (20 mL) and quenched with water. The organic layer was dried (MgSO$_4$) and concentrated in vacuo to give (2,3,4,5,6-pentafluorophenyl) phenyl carbonate (4.878 g, 16.04 mmol, 98% yield) as a solid, 1H NMR (400 MHz, CDCl$_3$) 7.48-7.39 (m, 2H), 7.35-7.26 (m, 3H)

Step 2: Preparation of phenyl N-2-[2-methoxy-4-oxo-3-(2,4,6-trimethylphenyl)cyclopent-2-en-1-yl] ethyl]carbamate 5-(2-Aminoethyl)-3-methoxy-2-(2,4,6-trimethylphenyl)cyclopent-2-en-1-one hydrochloride (4.6 mmol, 4.6 mmol) was dissolved in dichloromethane (50 mL) and N,N-diethylethanamine (9.2 mmol) was added. (2,3,4,5,6-Pentafluorophenyl) phenyl carbonate (4.6 mmol) was added and the reaction mixture was stirred at room temperature for 1.5 hours. The reaction mixture was diluted with 2M HCl and extracted twice with DCM. The organic layers were dried (MgSO$_4$) and concentrated in vacuo to leave an orange gum which was purified by flash column chromatography using a gradient elution from 5% EtOAc in i-hexane to 100% EtOAc to give phenyl N-2-[2-methoxy-4-oxo-3-(2,4,6-trimethylphenyl)cyclopent-2-en-1-yl]ethyl]carbamate (1.883 g, 4.785 mmol, 100% yield).

1H NMR (400 MHz, CDCl$_3$) 7.41-7.34 (m, 2H), 7.24-7.18 (m, 1H), 7.13 (d, 2H), 6.86 (s, 2H), 5.18-5.00 (m, 1H), 3.54 (s, 3H), 3.47-3.34 (m, 2H), 2.99 (br. s., 1H), 2.81 (dd, 1H), 2.32 (dd, 1H), 2.26 (s, 3H), 2.24-2.15 (m, 1H), 2.11 (s, 6H), 1.79-1.66 (m, 1H)

Step 3: Preparation of 1-[2-[2-methoxy-4-oxo-3-(2,4,6-trimethylphenyl)cyclopent-2-en-1-yl]ethyl]-3-methyl-urea Phenyl N-[2-[2-methoxy-4-oxo-3-(2,4,6-trimethylphenyl)cyclopent-2-en-1-yl]ethyl]carbamate (0.209 g, 0.531 mmol) was dissolved in acetonitrile (3 mL). N,N-Diethylethanamine (1.17 mmol) was added followed by methanamine hydrochloride (0.637 mmol). The reaction mixture was heated in the microwave at 120° C. for 45 mins. The reaction mixture was diluted with water and the pH was adjusted to ~7 using 2M HCl. the reaction mixture was extracted twice with EtOAc. The combined organic layers were dried (MgSO$_4$) and concentrated in vacuo to leave a yellow gum which was purified by flash column chromatography using a gradient elution from DCM to 10% MeOH in DCM to furnish 1-[2-[2-methoxy-4-oxo-3-(2,4,6-trimethylphenyl)cyclopent-2-en-1-yl]ethyl]-3-methyl-urea (0.105 g, 0.318 mmol, 60% yield).

1H NMR (400 MHz, CDCl$_3$) 6.86 (s, 2H), 4.43 (t, 1H), 4.28 (d, 1H), 3.55-3.47 (m, 3H), 3.36-3.25 (m, 2H), 3.00-2.86 (m, 1H), 2.83-2.74 (m, 4H), 2.30 (dd, 1H), 2.26 (s, 3H), 2.18-2.11 (m, 1H), 2.10-2.05 (m, 6H), 1.65-1.59 (m, 1H).

Step 4: Preparation of 1-[2-[2,4-dioxo-3-(2,4,6-trimethylphenyl)cyclopentyl]ethyl]-3-methyl-urea 1-[2-[2-methoxy-4-oxo-3-(2,4,6-trimethylphenyl)cyclopent-2-en-1-yl]ethyl]-3-methyl-urea (0.055 g, 0.17 mmol) was dissolved in acetone (10 mL/mmol) and hydrochloric acid (2 M solutionm, 10 mL/mmol, 3.3 mmol) was added. The reaction mixture was heated at 60° C. for 13 hours, then a further potrion of hydrochloric acid (2 M solutionm 10 mL/mmol, 3.3 mmol) was added and lelft to stir for 2 hours. The reaction mixture was concentrated in vacuo to furnish 1-[2-[2,4-dioxo-3-(2,4,6-trimethylphenyl)cyclopentyl]ethyl]-.3-methyl-urea (0.0514 g, 0.162 mmol, 98 yield) as a yellow glassy solid.

1H NMR (400 MHz, CD$_3$OD) 6.88 (s, 2H), 3.51-3.33 (m, 2H), 2.98 (dd, 1H), 2.84-2.75 (m, 4H), 2.49-2.39 (m, 1H), 2.27-2.22 (m, 3H), 2.10-1.98 (m, 7H), 1.80-1.70 (m, 1H)

Example 12

Preparation of N-[2-[3-(2,4-dimethyl-6-vinyl-phenyl)-2,4-dioxo-cyclopentyl]ethyl]-5,5-dimethyl-4H-isoxazole-3-carboxamide (Compound A122)

Step 1: Preparation of 2-(2-bromo-4,6-dimethyl-phenyl)-3-methoxy-cyclopent-2-en-1-one 2-(2-Bromo-4,6-dimethyl-phenyl)cyclopentane-1,3-dione (2.500 g, 8.892 mmol) and potassium carbonate sesquihydrate (13.34 mmol) were suspended in acetone (55 mL). Iodomethane (44.46 mmol) was added and the reaction mixture was stirred at room temperature overnight. The reaction mixture was poured into 2M HCl and extracted with EtOAc. The organic layers were dried (MgSO$_4$) and concentrated in vacuo to leave a dark orange oil to give 2-(2-bromo-4,6-dimethyl-phenyl)-3-methoxy-cyclopent-2-en-1-one (2.498 g, 8.463 mmol, 95 yield) which was used in the next step without further purification. 1H NMR (400 MHz, CDCl$_3$) 7.27 (br. s., 1H), 7.02-6.92 (m, 1H), 3.79 (s, 3H), 2.86-2.74 (m, 2H), 2.71-2.60 (m, 2H), 2.30-2.23 (m, 3H), 2.19-2.11 (m, 3H)

Step 2: Preparation of 2-(2-bromo-4,6-dimethyl-phenyl)-3-methoxy-cyclopent-2-en-1-one 2-(2-Bromo-4,6-dimethyl-phenyl)-3-methoxy-cyclopent-2-en-1-one (2.498 g, 8.462 mmol) was dissolved in tetrahydrofuran (30 mL/g) and cooled to −70° C. Lithium bis(trimethylsilyl)amide (1M in THF, 9.308 mmol) was added dropwise and the reaction was allowed to stir for 1 hour. 2-Bromoacetonitrile (9.477 mmol) was then added and after 30 mins, the reaction mixture was allowed to warm to 0° C. and stirred for a further 1 hr. The reaction mixture was quenched with 0.5 M NH$_4$Cl and the reaction mixture was extracted with ethyl acetate. The organic layer was combined, washed with brine, dried (MgSO4) and concentrated. This resulting residue was purified by flash column chromatography using a gradient elution from 5% EtOAc in i-hexane to 100% EtOAc to furnish 2-[3-(2-bromo-4,6-dimethyl-phenyl)-2-methoxy-4-oxo-cyclopent-2-en-1-yl] acetonitrile (0.350 g, 1.05 mmol, 12% yield) and 2-[3-(2-bromo-4,6-dimethyl-phenyl)-4-methoxy-2-oxo-cyclopent-3-en-1-yl]acetonitrile (0.404 g, 1.21 mmol, 14% yield).

2-[3-(2-bromo-4,6-dimethyl-phenyl)-2-methoxy-4-oxo-cyclopent-2-en-1-yl]acetonitrile: 1H NMR (400 MHz, CDCl$_3$) 7.29-7.26 (m, 1H), 7.04-6.94 (m, 1H), 3.69-3.61 (m, 3H), 3.24 (ddt, 1H), 2.96-2.82 (m, 2H), 2.71-2.59 (m, 1H), 2.50 (dd, 1H), 2.31-2.27 (m, 3H), 2.17 (s, 3H)

2-[3-(2-bromo-4,6-dimethyl-phenyl)-4-methoxy-2-oxo-cyclopent-3-en-1-yl]acetonitrile: 1H NMR (400 MHz, CDCl$_3$) 7.32-7.26 (m, 1H), 7.06-6.87 (m, 1H), 3.75-3.60 (m, 4H), 3.38-3.13 (m, 1H), 2.96-2.74 (m, 2H), 2.57-2.41 (m, 1H), 2.35-2.24 (m, 6H)

Step 3: Preparation of N-[2-3-(2-bromo-4,6-dimethyl-phenyl)-2-methoxy-4-oxo-cyclopent-2-en-1-yl] ethyl]-5,5-dimethyl-4H-isoxazole-3-carboxamide A glass pressure vessel was charged with raney nickel 2400 (0.200 g, 2.28 mmol) which was subsequently washed with distilled water (3×5 mL), and the excess water decanted off, leaving the nickel damp. 2-[3-(2-Bromo-4,6-dimethyl-phenyl)-2-methoxy-4-oxo-cyclopent-2-en-1-yl]acetonitrile (0.250 g, 0.748 mmol), (2,3,4,5,6-pentafluorophenyl) 5,5-dimethyl-4H-isoxazole-3-carboxylate (1.05 mmol), and 1,2-dimethoxyethane (20 mL/g) were added to the vessel. The vessel was sealed, purged with nitrogen followed by hydrogen, and stirred at room temperature under 3.5 Bar of hydrogen pressure for 3 hours. The reaction mixture was filtered through celite, washed with methanol, and the combined organic layers were concentrated. The resulting residue was purified by flash column chromatography using a gradient elution from 10% EtOAc in i-hexane to 100% EtOAc to furnish
N-[2-[3-(2-bromo-4,6-dimethyl-phenyl)-2-methoxy-4-oxo-cyclopent-2-en-1-yl]ethyl]-5,5-dimethyl-4H-isoxazole-3-carboxamide (D, 0.070 g, 0.15 mmol, 20% yield).

H NMR (400 MHz, CDCl$_3$) 7.27-7.16 (m, 1H), 7.02-6.91 (m, 1H), 6.77 (br. s., 1H), 3.65-3.57 (m, 3H), 3.55-3.45 (m, 2H), 3.03-2.97 (m, 2H), 2.97-2.88 (m, 1H), 2.83-2.72 (m, 1H), 2.39-2.30 (m, 1H), 2.28 (s, 3H), 2.19-2.13 (m, 4H), 1.88-1.73 (m, 1H), 1.48-1.37 (m, 6H).

Step 4: Preparation of N-[2-[3-(2,4-dimethyl-6-vinyl-phenyl)-2-methoxy-4-oxo-cyclopent-2-en-1-yl]ethyl]-5,5-dimethyl-4H-isoxazole-3-carboxamide N-[2-[3-(2-bromo-4,6-dimethyl-phenyl)-2-methoxy-4-oxo-cyclopent-2-en-1-yl]ethyl]-5,5-dimethyl-4H-isoxazole-3-carboxamide (0.070 g, 0.15 mmol) and tetrakis(triphenyl-phosphine)palladium(0) (0.015 mmol) was dissolved in toluene (14.7 mL/mmol, 21 mmol) and tributyl(vinyl)stannane (0.18 mmol) was added. The reaction mixture was heated to reflux for 2 hr. The mixture was cooled to room temperature diluted with EtOAc, filtered and concentrated. The resulting residue was purified by flash column chromatography using a gradient elution from 0 to 5% MeOH in DCM to furnish N-[2-[3-(2,4-dimethyl-6-vinyl-phenyl)-2-methoxy-4-oxo-cyclopent-2-en-1-yl]ethyl]-5,5-dimethyl-4H-isoxazole-3-carboxamide (0.053 g, 0.13 mmol, 85% yield).

1H NMR (400 MHz, CDCl$_3$) 7.24-7.19 (m, 1H), 6.96 (s, 1H), 6.77 (br. s., 1H), 6.54 (dd, 1H), 5.63 (ddd, 1H), 5.24-5.14 (m, 1H), 3.56-3.42 (m, 5H), 3.00 (d, 2H), 3.00-2.93 (m, 1H), 2.81 (ddd, 1H), 2.34-2.29 (m, 4H), 2.16 (dd, 1H), 2.12-2.06 (m, 3H), 1.78-1.63 (m, 1H), 1.48-1.41 (m, 6H)

Step 5: Preparation of N-[2-[3-(2,4-dimethyl-6-vinyl-phenyl)-2,4-dioxo-cyclopentyl]ethyl]-5,5-dimethyl-4H-isoxazole-3-carboxamide N-[2-[3-(2,4-Dimethyl-6-vinyl-phenyl)-2-methoxy-4-oxo-cyclopent-2-en-1-yl]ethyl]-5,5-dimethyl-4H-isoxazole-3-carboxamide (0.053 g, 0.13 mmol) was suspended in acetone (5.89 mL/mmol) and hydrochloric acid (2M solution, 5.89 mL/mmol, 1.5 mmol) was added.

The reaction mixture was heated at 60° C. for 4 hours, then cooled to room temperature. The mixture was concentrated in vacuo to give N-[2-[3-(2,4-dimethyl-6-vinyl-phenyl)-2,4-dioxo-cyclopentyl]ethyl]-5,5-dimethyl-4H-isoxazole-3-carboxamide (0.025 g, 0.063 mmol, 49% yield) as a yellow foam.

1HNMR (400 MHz, CD3OD) 7.26 (d, 1H), 7.02-6.92 (m, 1H), 6.59-6.42 (m, 1H), 5.60 (ddd, 1H), 5.15-5.04 (m, 1H), 3.50-3.37 (m, 2H), 3.01-2.97 (m, 2H), 2.95-2.71 (m, 2H), 2.47 (d, 1H), 2.33-2.26 (m, 3H), 2.21-2.08 (m, 1H), 2.05 (d, 3H), 1.72-1.60 (m, 1H), 1.46-1.39 (m, 6H)

Example 13

Preparation of N-[2-[3-(2-ethynyl-4,6-dimethyl-phenyl)-2,4-dioxo-cyclopentyl]ethyl]-5,5-dimethyl-4H-isoxazole-3-carboxamide (A123)

Step 1: Preparation of N-[2-[3-[2,4-dimethyl-6-(2-trimethylsilylethynyl)phenyl]-2-methoxy-4-oxo-cyclopent-2-en-1-yl]ethyl]-5,5-dimethyl-4H-isoxazole-3-carboxamide N-[2-[3-(2-Bromo-4,6-dimethyl-phenyl)-2-methoxy-4-oxo-cyclopent-2-en-1-yl]ethyl]-5,5-dimethyl-4H-isoxazole-3-carboxamide (0.080 g, 0.17 mmol), trimethyl(2-tributyl-stannylethynyl)silane (0.21 mmol) and tetrakis(triphenylphosphine)palladium(0) (0.017 mmol) was suspended in toluene (2 mL, 18.7 mmol). The mixture was heated under reflux for 3 h. A further portion of trimethyl (2-tributylstannylethynyl)silane (0.21 mmol) and tetrakis (triphenylphosphine)palladium(0) (0.017 mmol) were added and the reaction mixture was heated for a further 2 hours. The reaction mixture was cooled to room temperature diluted with EtOAc and filtered through MgSO4. The filtrate was concentrated in vacuo and the resulting residue was purified by flash column chromatography using a gradient elution from DCM to 5% MeOH in DCM to furnish N-[2-[3-[2,4-dimethyl-6-(2-trimethylsilylethynyl)phenyl]-2-methoxy-4-oxo-cyclopent-2-en-1-yl]ethyl]-5,5-dimethyl-4H-isoxazole-3-carboxamide (0.059 g, 0.12 mmol, 71% yield).

1H NMR (400 MHz, CDCl3) 7.21-7.13 (m, 1H), 7.02-6.95 (m, 1H), 6.77 (d, 1H), 3.62 (d, 3H), 3.56-3.43 (m, 2H), 3.00 (d, 2H), 2.97-2.85 (m, 1H), 2.82-2.68 (m, 1H), 2.34-2.29 (m, 1H), 2.29-2.23 (m, 3H), 2.17-2.11 (m, 3H), 1.83-1.62 (m, 1H), 1.49-1.41 (m, 6H), 1.41-1.28 (m, 1H), 0.21-0.16 (m, 9H)

Step 2: Preparation of N-[2-[3-(2-ethynyl-4,6-dimethyl-phenyl)-2,4-dioxo-cyclopentyl]ethyl]-5,5-dimethyl-4H-isoxazole-3-carboxamide N-[2-[3-[2,4-Dimethyl-6-(2-trimethylsilylethynyl)phenyl]-2-methoxy-4-oxo-cyclopent-2-en-1-yl]ethyl]-5,5-dimethyl-4H-isoxazole-3-carboxamide (0.059 g, 0.12 mmol) was suspended in acetone (5.89 mL/mmol) and hydrochloric acid (2M solution, 5.89 mL/mmol, 1.4 mmol) was added. The reaction mixture was heated at 60° C. for 5 hour 30 min then cooled to room temperature. More acetone (5.89 mL/mmol) and hydrochloric acid (2M solution, 5.89 mL/mmol, 1.4 mmol) were added to the reaction mixture which was heated for a further 5 hours. The reaction mixture was concentrated to remove the acetone and the residue was extracted twice with EtOAc. The organic layers were dried (MgSO$_4$) and concentrated in vacuo and the resulting residue was purified by flash column chromatography using a gradient elution from DCM to 10% MeOH in DCM to furnish N-[2-[3-(2-ethynyl-4,6-dimethyl-phenyl)-2,4-dioxo-cyclopentyl]ethyl]-5,5-dimethyl-4H-isoxazole-3-carboxamide (0.013 g, 0.033 mmol, 27% yield).

1H NMR (400 MHz, CD$_3$OD) 7.38 (s, 1H), 7.25 (s, 1H), 3.57-3.38 (m, 2H), 3.04-2.94 (m, 2H), 2.97-2.82 (m, 1H), 2.79-2.66 (m, 1H), 2.47 (s, 1H), 2.43 (br. s., 1H), 2.38 (s, 3H), 2.15 (s, 3H), 2.14-2.05 (m, 1H), 1.81-1.60 (m, 1H), 1.42 (d, 6H)

Example 14

Chiral HPLC or SFC Separation of Enantiomers

In one optional embodiment of the invention, any specific compound of the invention is separated into the two corresponding enantiomerically pure (or subtantially enantiomerically pure) compounds using a chiral HPLC or SFC column. In one optional example, the chiral HPLC uses the following method and the following conditions.

Chiral HPLC column: a (s,s) WhelkO1—5 micron—21 mm×250 mm HPLC column, manufactured by Regis Technologies, Inc. In this column, the chiral stationary phase is (S,S) 1-(3-5-dinitrobenzamido)-1,2,3,4-tetrahydrophenanthrene.

The solvent system to be used as an eluent for the column varies depending on the racemic compound to be separated into enantiomers, but one example of a solvent system is: a 30:70 (by volume) mixture of Solvent A and Solvent B, in which:

Solvent A is isohexane containing 0.1% v/v of trifluoroacetic acid (TFA), and Solvent B is ethanol.

Other conditions (these are sample conditions only and may vary widely):

Flow rate through column: about 21 ml/minute. Run time: about 20 minutes.

Loading (compound loaded onto column): about 50 mg/ml of compound in ethanol.

Volume of sample (compound) injected per run=about 1800 microliters.

Number of injections of compound=about 5.

Abbreviation:

HPLC=high performance (or high pressure) liquid chromatography.

SFC=Supercritical fluid chromatography

General Note on Chiral HPLC or SFC Separation of Enantiomers:

In one optional embodiment, the above procedure using chiral HPLC is used to separate the enantiomers of other compounds of formula (I) of the present the invention. Alternative chiral columns which might be useful to achieve this are as follows:

(s,s) WhelkO1—5 micron—21 mm×250 mm HPLC column, manufactured by Regis Technologies, Inc [in this column, the chiral stationary phase is (S,S) 1-(3-5-dinitrobenzamido)-1,2,3,4-tetrahydrophenanthrene];

Kromasil® AmyCoat™ [whose chiral stationary phase is tris-(3,5-dimethylphenyl)carbamoyl amylose];

Kromasil® CelluCoat™ [whose chiral stationary phase is tris-(3,5-dimethylphenyl)carbamoyl cellulose];

Chiralpak® IA [whose chiral stationary phase is a (3,5-dimethylphenyl)carbamate derivative of amylose];

Chiralpak® IB [whose chiral stationary phase is tris-(3, 5-dimethylphenyl)carbamate derivative of cellulose];

Chiralpak® IC [whose chiral stationary phase is cellulose tris(3,5-dichlorophenyl) carbamate];

Lux® Amylose-2 [whose chiral stationary phase is amylose tris(5-chloro-2-methylphenylcarbamate)]; or Lux® Cellulose-2 [whose chiral stationary phase is Cellulose tris(3-chloro-4-methylphenylcarbamate)].

Lux® Cellulose-4 [whose chiral stationary phase is Cellulose tris(4-chloro-3-methylphenylcarbamate)]

Chiral HPLC Separation of Enantiomers of Compound A122 to Compounds A122a and A122b.

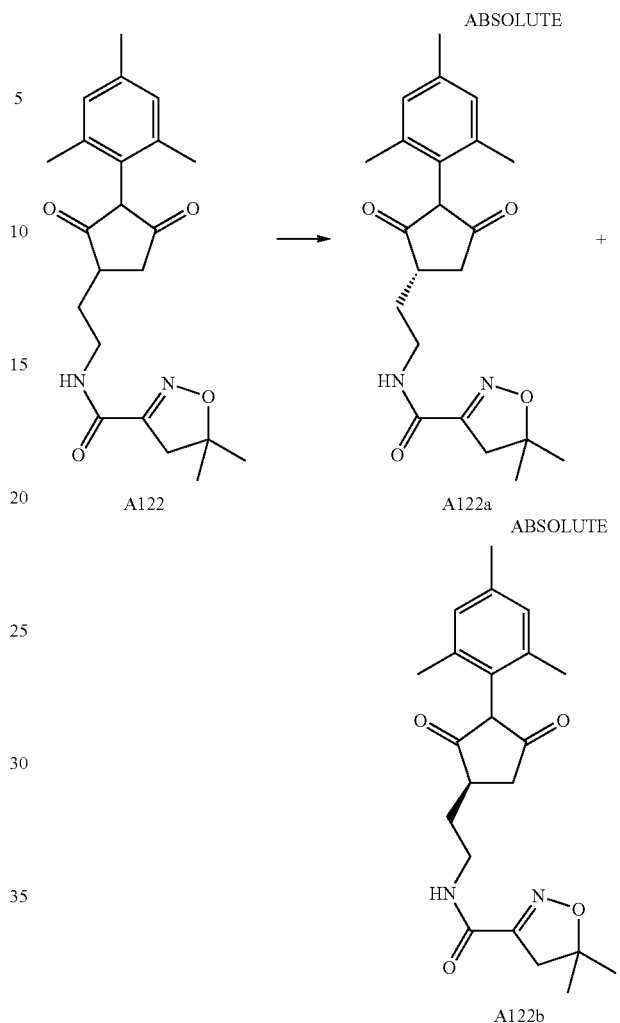

Compound A122 (racemic), was separated into the enantiomers A122a and A122b using a chiral SFC column, by the following method and under the following conditions.

The chiral SFC column used was Lux C4 (21.2 mm×250 mm, 5 um).

The solvent system used as an eluent for the column was a 40:60 (by volume) mixture of methanol and supercritical carbon dioxide with 0.1% TEA.

Other conditions were as follows:

Flow rate through column: 50 ml/minute.

Volume of sample (compound) injected per run=0.2 mL (10 mg)

Length of run=8 minutes

Detection wavelength=230 nm

Chiral SFC on a total of 2.59 g of compound A122 under the above conditions gave 1.08 g of compound A122a (99.3% enantiomeric excess (e.e.), retention time 5.67 minutes under the above conditions) and 1.01 g of compound A122b (99% enantiomeric excess (e.e.), retention time 6.39 minutes under the above conditions).

Abbreviation: SFC=Supercritical fluid chromatography

Additional compounds in Table T1 below illustrate the present invention, and are particular embodiments of the compounds of formula (I) according to the present invention. For the most part, these compounds can generally be prepared by methods similar to those shown in the Examples and/or in the process section hereinabove using appropriate starting materials.

TABLE T1

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A1 | 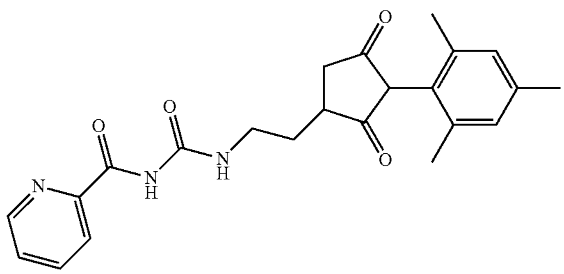 [SMILES: Cc1cc(C)c(C2C(=O)CC(CCNC(=O)NC(=O)c3ccccn3)C2=O)c(C)c1] | 1H NMR (400 MHz, d4-methanol) 1.68-1.78 (1H, m), 2.03-2.08 (6H, s), 2.13-2.21 (1H, m), 2.22-2.26 (3H, s), 2.44-2.52 (1H, dd), 2.77-2.84 (1H, m), 2.88-2.97 (1H, dd), 3.48-3.54 (2H, dt), 6.83-6.87 (2H, s), 7.59-7.64 (1H, m), 7.97-8.03 (1H, dt), 8.16-8.22 (1H, d), 8.64-8.68 (1H, d) |
| A2 | 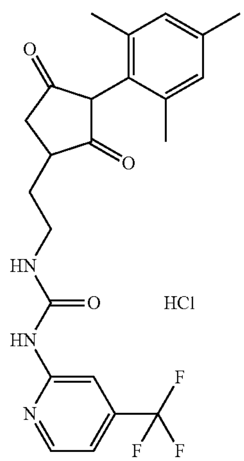 [SMILES: Cc1cc(C)c(C2C(=O)CC(CCNC(=O)Nc3cc(C(F)(F)F)ccn3)C2=O)c(C)c1 ; Cl] | 1HNMR(400 MHz, d4-methanol) 8.47-8.36 (m, 1H), 7.60 (s, 1H), 7.42 (d, 1H), 6.88 (s, 2H), 3.56-3.47 (m, 2H), 2.97 (dd, 1H), 2.89-2.77 (m, 1H), 2.50 (dd, 1H), 2.27 (s, 3H), 2.17 (d, 1H), 2.10-2.00 (m, 6H), 1.82-1.69 (m, 1H) |
| A3 | 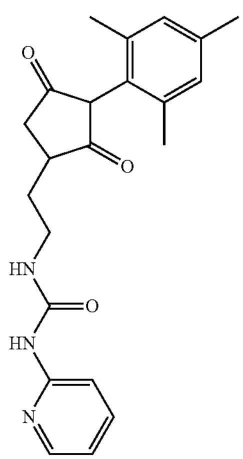 | 1HNMR(400 MHz, d4-methanol) 8.36-8.19 (m, 2H), 7.45-7.32 (m, 2H), 6.91-6.83 (m, 2H), 3.54-3.41 (m, 2H), 2.99 (dd, 1H), 2.88-2.77 (m, 1H), 2.51 (dd, 1H), 2.30-2.24 (m, 3H), 2.21-2.10 (m, 1H), 2.09-2.02 (m, 6H), 1.78-1.67 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A4 | 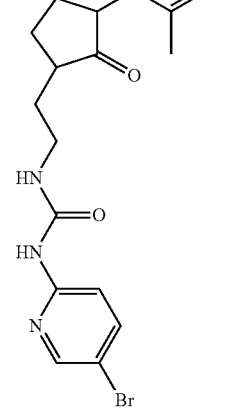 HCl | 1HNMR(400 MHz, d4-methanol) 8.38 (d, 1H), 8.31 (dd, 1H), 7.26 (d, 1H), 6.89 (s, 2H), 3.51-3.44 (m, 2H), 3.02-2.95 (m, 1H), 2.82 (td, 1H), 2.49 (dd, 1H), 2.27-2.22 (m, 3H), 2.17-2.11 (m, 1H), 2.06 (d, 6H), 1.81-1.67 (m, 1H) |
| A5 | 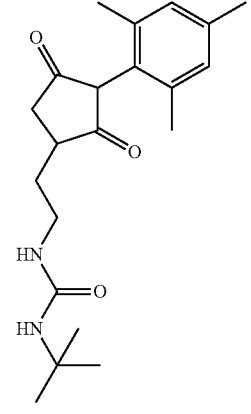 | 1HNMR(400 MHz, d4-methanol) 6.86 (s, 2H), 3.28-3.06 (m, 2H), 2.88 (dd, 1H), 2.75 (br.s., 1H), 2.40 (d, 1H), 2.25 (s, 3H), 2.07-2.01 (m, 6H), 2.01-1.91 (m, 1H), 1.64-1.53 (m, 1H), 1.30 (s, 9H) |
| A6 | 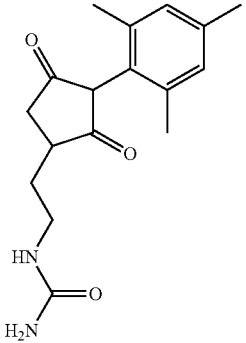 [SMILES: Cc1cc(C)c(C2C(=O)CC(CCNC(N)=O)C2=O)c(C)c1] | 1HNMR(400 MHz, d4-methanol) 6.87-6.81 (m, 2H), 3.28-3.20 (m, 2H), 2.93-2.84 (m, 1H), 2.46-2.37 (m, 1H), 2.25 (s, 3H), 2.04 (d, 6H), 2.02-1.96 (m, 1H), 1.66-1.55 (m, 1H), 0.21-0.20 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A7 | 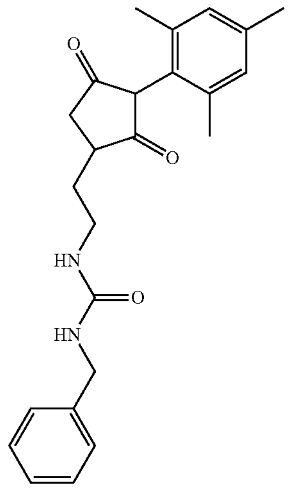 [SMILES: Cc1cc(C)c(C2C(=O)CC(CCNC(=O)NCc3ccccc3)C2=O)c(C)c1] | 1HNMR(400 MHz, d4-methanol) 7.34-7.26 (m, 4H), 7.26-7.18 (m, 1H), 6.87 (s, 2H), 4.33 (s, 2H), 3.40-3.31 (m, 2H), 2.89 (dd, 1H), 2.80-2.69 (m, 1H), 2.42 (dd, 1H), 2.25 (s, 3H), 2.04 (d, 6H), 2.04-1.95 (m, 1H), 1.69-1.55 (m, 1H) |
| A8 | 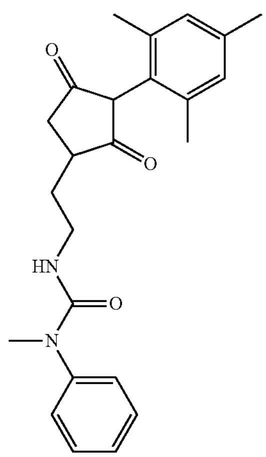 | 1HNMR(400 MHz, d4-methanol) 7.46-7.40 (m, 2H), 7.35-7.26 (m, 3H), 6.86 (s, 2H), 3.28-3.21 (m, 5H), 2.88 (dd, 1H), 2.76-2.66 (m, 1H), 2.42 (d, 1H), 2.25 (s, 3H), 2.03 (d, 6H), 2.01-1.91 (m, 1H), 1.64-1.50 (m, 1H) |
| A9 | 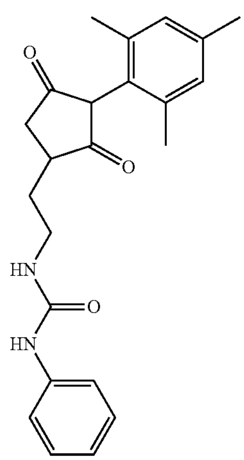 [SMILES: Cc1cc(C)c(C2C(=O)CC(CCNC(=O)Nc3ccccc3)C2=O)c(C)c1] | 1HNMR(400 MHz, d4-methanol) 7.38-7.31 (m, 2H), 7.27-7.18 (m, 2H), 7.00-6.92 (m, 1H), 6.86 (s, 2H), 3.42-3.33 (m, 2H), 2.95-2.75 (m, 2H), 2.48-2.41 (m, 1H), 2.25 (s, 3H), 2.12-2.06 (m, 1H), 2.05 (s, 6H), 1.66 (qd, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A10 | 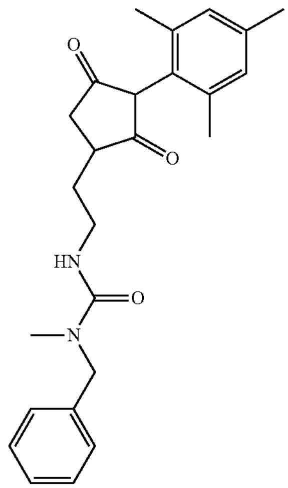 | 1HNMR(400 MHz, d4-methanol) 7.36-7.28 (m, 2H), 7.29-7.20 (m, 3H), 6.90-6.80 (m, 2H), 4.58-4.48 (m, 2H), 3.48-3.32 (m, 2H), 2.94 (dd, 1H), 2.87 (s, 3H), 2.82-2.71 (m, 1H), 2.48-2.40 (m, 1H), 2.25 (s, 3H), 2.08-1.98 (m, 7H), 1.77-1.61 (m, 1H) |
| A11 | 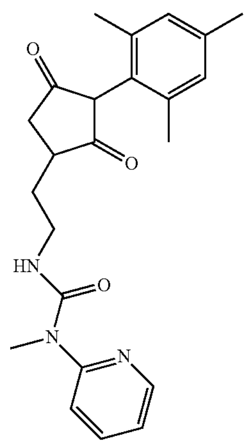 | 1HNMR(400 MHz, d4-methanol) 8.47-8.32 (m, 2H), 7.74-7.64 (m, 1H), 7.55-7.42 (m, 1H), 6.88-6.79 (m, 2H), 3.55-3.45 (m, 2H), 3.34-3.28 (m, 3H), 3.04-2.94 (m, 1H), 2.88-2.80 (m, 1H), 2.54-2.46 (m, 1H), 2.25-2.22 (m, 3H), 2.22-2.15 (m, 1H), 2.10-2.00 (m, 6H), 1.80-1.69 (m, 1H) |
| A12 | 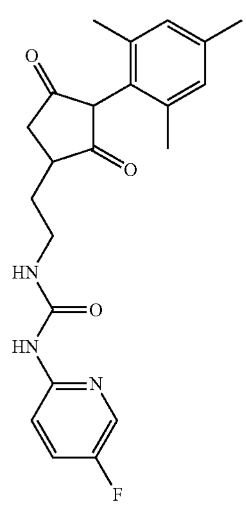 [SMILES: Cc1cc(C)c(C2C(=O)CC(CCNC(=O)Nc3ccc(F)cn3)C2=O)c(C)c1] | 1HNMR(400 MHz, d4-methanol,) 8.31-8.21 (m, 2H), 7.42 (dd, 1H), 6.90-6.78 (m, 2H), 3.46 (t, 2H), 3.04-2.91 (m, 1H), 2.85-2.77 (m, 1H), 2.54-2.42 (m, 1H), 2.24 (s, 3H), 2.21-2.09 (m, 1H), 2.07-2.01 (m, 6H), 1.78-1.67 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A13 | 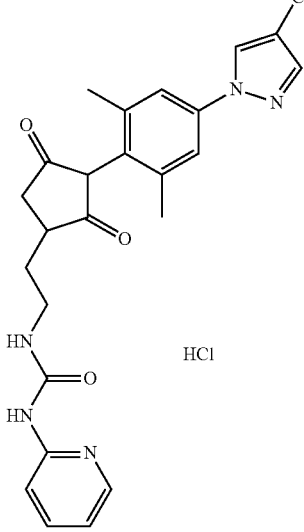 | 1HNMR(400 MHz, d4-methanol) 8.34 (s, 1H), 8.31-8.20 (m, 2H), 7.67 (s, 1H), 7.44 (s, 2H), 7.42-7.33 (m, 2H), 3.50 (t, 2H), 3.04 (dd, 1H), 2.87 (br.s., 1H), 2.55 (d, 1H), 2.18 (s, 7H), 1.80-1.64 (m, 1H) |
| A14 | 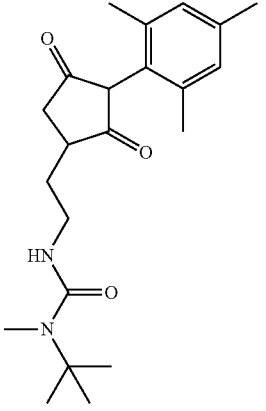 | 1HNMR(400 MHz, CDCl3) 6.90-6.79 (m, 2H), 3.86-3.70 (m, 1H), 3.54-3.43 (m, 1H), 3.15-3.04 (m, 1H), 2.91-2.83 (m, 2H), 2.83-2.79 (m, 3H), 2.26-2.20 (m, 3H), 2.13-2.01 (m, 6H), 1.97-1.84 (m, 1H), 1.77-1.62 (m, 1H), 1.41-1.35 (m, 9H) |
| A15 | 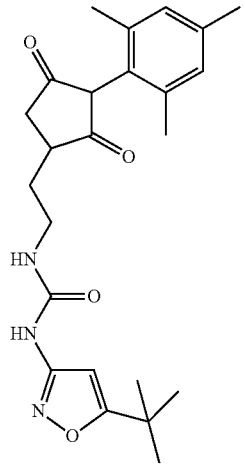 [SMILES: Cc1cc(C)c(C2C(=O)CC(CCNC(=O)Nc3cc(C(C)(C)C)on3)C2=O)c(C)c1] | 1HNMR(400 MHz, d4-methanol) 6.92-6.82 (m, 2H), 6.20 (s, 1H), 3.45-3.33 (m, 2H), 2.92 (dd, 1H), 2.83-2.73 (m, 1H), 2.46 (dd, 1H), 2.28-2.21 (m, 3H), 2.17-2.07 (m, 1H), 2.07-1.97 (m, 6H), 1.73-1.59 (m, 1H), 1.35-1.30 (m, 9H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A16 | 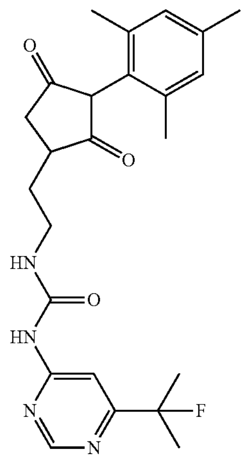 [SMILES: Cc1cc(C)c(C2C(=O)CC(CCNC(=O)Nc3cc(C(C)(C)F)ncn3)C2=O)c(C)c1] | 1HNMR(400 MHz, d4-methanol) 8.89 (s, 1H), 7.93 (s, 1H), 6.92-6.79 (m, 2H), 3.52-3.41 (m, 2H), 2.94 (dd, 1H), 2.87-2.73 (m, 1H), 2.48 (dd, 1H), 2.28-2.21 (m, 3H), 2.19-2.06 (m, 1H), 2.05 (d, 6H), 1.82-1.77 (m, 3H), 1.76-1.72 (m, 4H) |
| A17 | 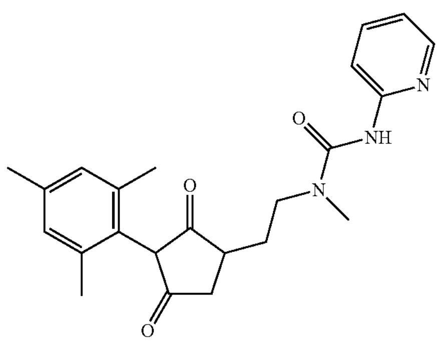 [SMILES: Cc1cc(C)c(C2C(=O)CC(CCN(C)C(=O)Nc3ccccn3)C2=O)c(C)c1] | 1HNMR(400 MHz, CDCl3) 8.26 (d, 2H), 7.57 (d, 1H), 7.41 (t, 1H), 6.89 (s, 2H), 3.22-2.98 (m, 5H), 2.83 (d, 1H), 2.48 (d, 1H), 2.32-2.23 (m, 4H), 2.13 (d, 8H), |
| A18 | 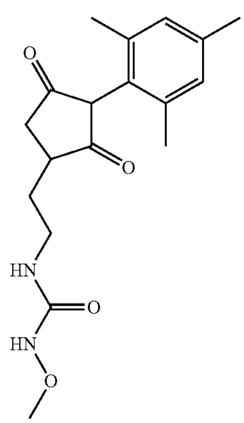 [SMILES: CONC(=O)NCCC1CC(=O)C(c2c(C)cc(C)cc2C)C1=O] | 1HNMR(400 MHz, d4-methanol,) 6.89-6.81 (m, 2H), 3.36 (t, 2H), 3.30 (s, 3H), 2.91 (dd, 1H), 2.76 (d, 1H), 2.48-2.38 (m, 1H), 2.25 (s, 3H), 2.09 (d, 1H), 2.04 (s, 6H), 1.70-1.59 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A19 | 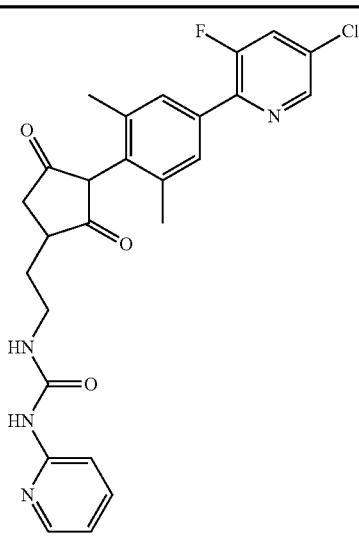 | 1HNMR(400 MHz, d4-methanol) 8.50 (d, 1H), 8.33-8.22 (m, 2H), 7.91-7.81 (m, 1H), 7.61 (s, 2H), 7.40 (t, 1H), 7.31 (d, 1H), 3.51-3.45 (m, 3H), 3.02 (dd, 1H), 2.85 (br.s., 1H), 2.59-2.44 (m, 1H), 2.19 (d, 6H), 1.77 (br.s., 1H) |
| A20 | 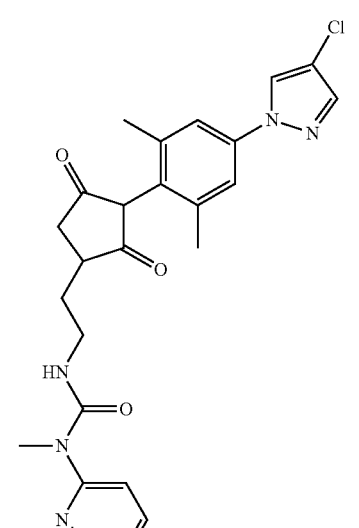 | 1HNMR(400 MHz, CDCl3) 11.00 (br.s., 1H), 8.31 (dd, 1H), 7.87-7.85 (m, 1H), 7.84-7.76 (m, 1H), 7.64-7.57 (m, 1H), 7.38-7.31 (m, 2H), 7.10-7.01 (m, 2H), 4.04-3.84 (m, 1H), 3.48-3.41 (m, 3H), 3.40-3.26 (m, 1H), 3.03 (d, 1H), 2.94-2.84 (m, 1H), 2.24 (d, 6H), 2.20-2.07 (m, 2H), 1.89-1.73 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A21 | 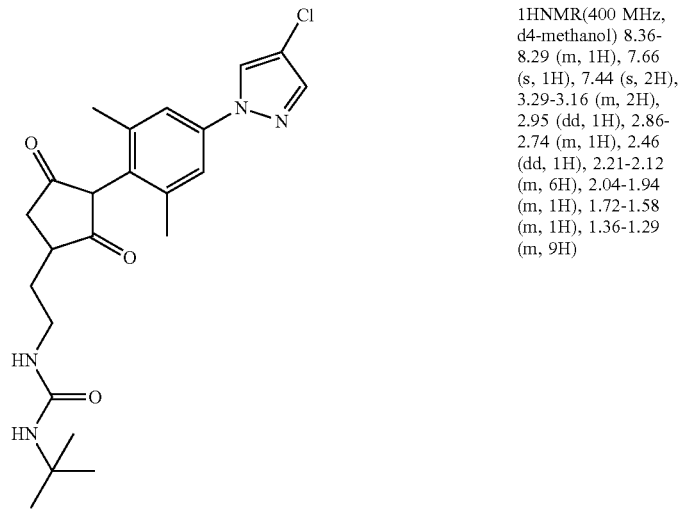 | 1HNMR(400 MHz, d4-methanol) 8.36-8.29 (m, 1H), 7.66 (s, 1H), 7.44 (s, 2H), 3.29-3.16 (m, 2H), 2.95 (dd, 1H), 2.86-2.74 (m, 1H), 2.46 (dd, 1H), 2.21-2.12 (m, 6H), 2.04-1.94 (m, 1H), 1.72-1.58 (m, 1H), 1.36-1.29 (m, 9H) |
| A22 | 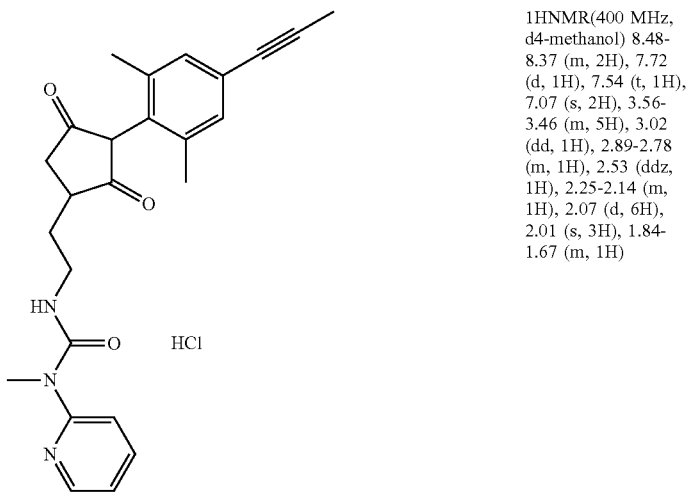 | 1HNMR(400 MHz, d4-methanol) 8.48-8.37 (m, 2H), 7.72 (d, 1H), 7.54 (t, 1H), 7.07 (s, 2H), 3.56-3.46 (m, 5H), 3.02 (dd, 1H), 2.89-2.78 (m, 1H), 2.53 (ddz, 1H), 2.25-2.14 (m, 1H), 2.07 (d, 6H), 2.01 (s, 3H), 1.84-1.67 (m, 1H) |
| A23 | 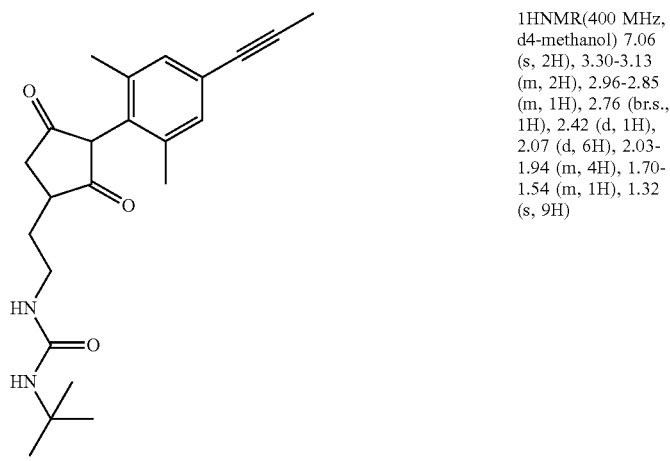 | 1HNMR(400 MHz, d4-methanol) 7.06 (s, 2H), 3.30-3.13 (m, 2H), 2.96-2.85 (m, 1H), 2.76 (br.s., 1H), 2.42 (d, 1H), 2.07 (d, 6H), 2.03-1.94 (m, 4H), 1.70-1.54 (m, 1H), 1.32 (s, 9H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A24 | 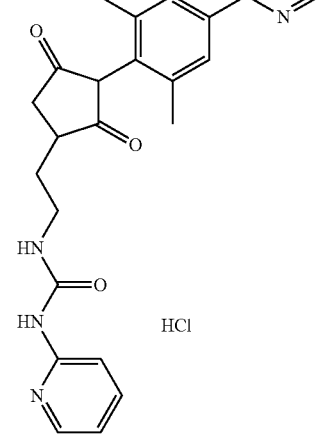 | 1HNMR(400 MHz, d4-methanol) 8.65 (dd, 1H), 8.53-8.42 (m, 1H), 8.25-8.12 (m, 2H), 7.99 (ddd, 1H), 7.46 (s, 2H), 7.34-7.22 (m, 2H), 3.39 (t, 2H), 3.03-2.91 (m, 1H), 2.82-2.73 (m, 1H), 2.48 (dd1H), 2.15 (d, 6H), 2.12-2.02 (m, 1H), 1.69-1.59 (m, 1H) |
| A25 | 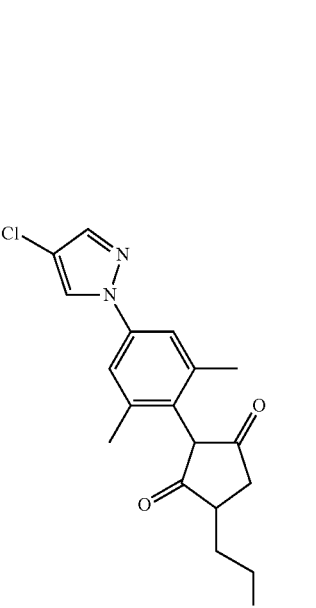 | 1HNMR(400 MHz, d4-methanol) 8.35 (s, 1H), 7.68 (s, 1H), 7.48-7.39 (m, 2H), 3.43-3.36 (m, 2H), 2.97 (dd, 1H), 2.80 (br.s., 1H), 2.50 (dd, 1H), 2.22-2.17 (m, 6H), 2.10 (dd, 1H), 1.73-1.63 (m, 1H), 1.28-1.25 (m, 9H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A26 | 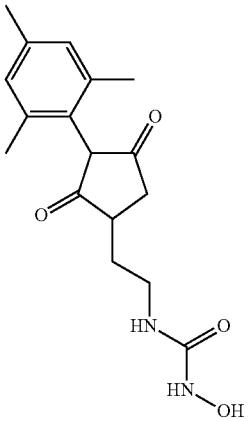 [SMILES: Cc1cc(C)c(C2C(=O)CC(CCNC(=O)NO)C2=O)c(C)c1] | 1HNMR(400 MHz, d4-methanol) 6.88 (s, 2H), 3.39 (t, 2H), 2.93 (dd, 1H), 2.84-2.74 (m, 1H), 2.46 (dd, 1H), 2.27 (s, 3H), 2.15-2.08 (m, 1H), 2.06 (s, 6H), 1.66 (tdd, 1H) |
| A27 | 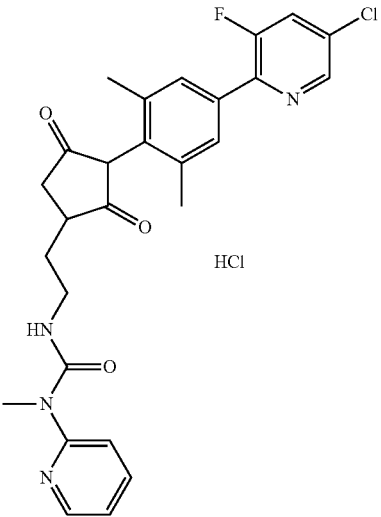 [SMILES: Cc1cc(-c2ncc(Cl)cc2F)cc(C)c1C1C(=O)CC(CCNC(=O)N(C)c2ccccn2)C1=O ; Cl] | 1HNMR(400 MHz, d4-methanol) 8.71 (d, 1H), 8.51-8.38 (m, 2H), 8.25 (dd, 1H), 7.74 (d, 1H), 7.59 (s, 2H), 7.55-7.49 (m, 1H), 3.59-3.49 (m, 5H), 3.15-3.02 (m, 1H), 2.95-2.86 (m, 1H), 2.60 (dd, 1H), 2.32-2.17 (m, 7H), 1.85-1.72 (m, 1H) |
| A28 | 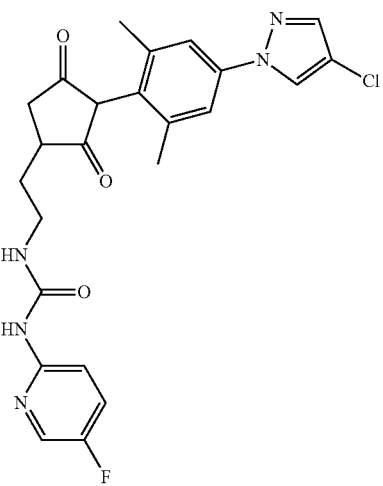 [SMILES: Cc1cc(-n2cc(Cl)cn2)cc(C)c1C1C(=O)CC(CCNC(=O)Nc2ccc(F)cn2)C1=O] | 1HNMR(400 MHz, d4-methanol) 8.35 (s, 1H), 8.32-8.29 (m, 1H), 8.28-8.24 (m, 1H), 7.68 (s, 1H), 7.47 (s, 2H), 7.42 (dd, 1H), 3.50 (t, 2H), 3.03 (dd, 1H), 2.91-2.82 (m, 1H), 2.54 (dd, 1H), 2.36-2.21 (m, 1H), 2.22-2.13 (m, 6H), 1.82-1.70 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A29 | 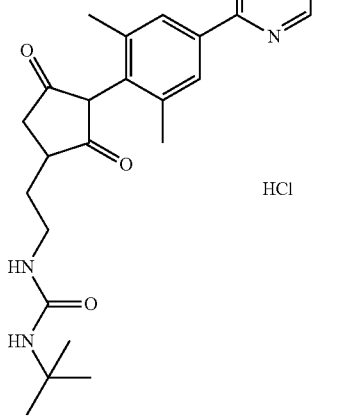 | 1HNMR(400 MHz, d4-methanol) 8.52-8.40 (m, 1H), 7.81 (dd, 1H), 7.58 (s, 2H), 3.31-3.15 (m, 2H), 2.86 (dd, 1H), 2.78-2.68 (m, 1H), 2.39 (dd, 1H), 2.25-2.14 (m, 6H), 2.06-1.97 (m, 1H), 1.60 (qd, 1H), 1.36-1.26 (m, 9H) |
| A30 | 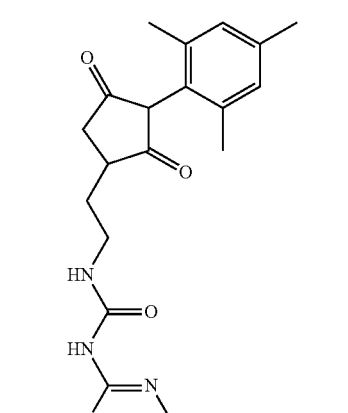 | 1HNMR(400 MHz, d4-methanol) 8.61-8.47 (m, 2H), 7.00 (t, 1H), 6.86-6.71 (m, 2H), 3.55-3.44 (m, 2H), 2.83-2.74 (m, 1H), 2.71-2.60 (m, 1H), 2.34 (dd, 1H), 2.22 (s, 3H), 2.21-2.13 (m, 1H), 2.09-2.04 (m, 6H), 1.70 (tdd, 1H) |
| A31 | 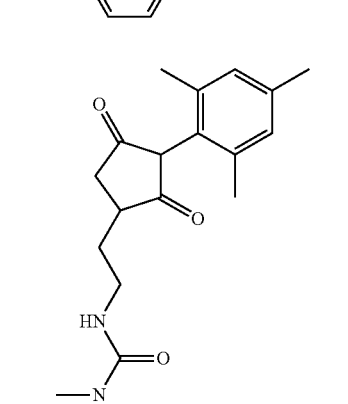 | 1HNMR(400 MHz, d4-methanol) 6.93-6.81 (m, 2H), 3.57-3.47 (m, 1H), 3.41-3.33 (m, 1H), 3.05 (dd, 1H), 3.01-2.97 (m, 6H), 2.95-2.84 (m, 1H), 2.48 (dd, 1H), 2.26 (s, 3H), 2.07-2.01 (m, 6H), 1.99-1.79 (m, 2H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A32 | 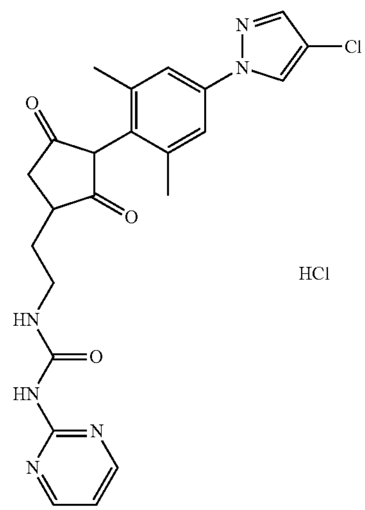 [SMILES: Cc1cc(-n2cc(Cl)cn2)cc(C)c1C1C(=O)CC(CCNC(=O)Nc2ncccn2)C1=O ; Cl] | 1HNMR(400 MHz, d4-methanol) 8.61-8.54 (m, 2H), 8.36-8.28 (m, 1H), 7.65 (s, 1H), 7.49-7.36 (m, 2H), 7.10-6.99 (m, 1H), 3.60-3.47 (m, 2H), 3.04-2.93 (m, 1H), 2.91-2.81 (m, 1H), 2.53 (dd, 1H), 2.21-2.11 (m, 7H), 1.78 (tdd, 1H) |
| A33 | 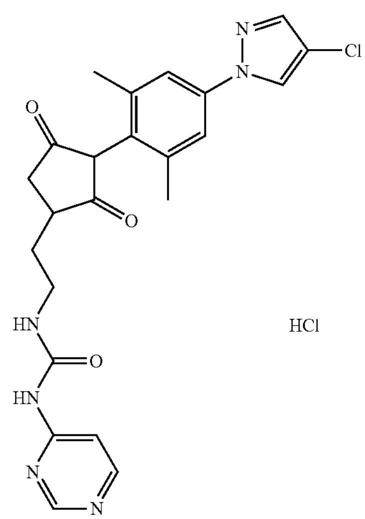 [SMILES: Cc1cc(-n2cc(Cl)cn2)cc(C)c1C1C(=O)CC(CCNC(=O)Nc2ccncn2)C1=O ; Cl] | 1HNMR(400 MHz, d4-methanol) 9.09-8.93 (m, 1H), 8.66-8.54 (m, 1H), 8.36-8.29 (m, 1H), 8.31-8.04 (m, 1H), 7.70-7.58 (m, 1H), 7.46-7.32 (m, 2H), 3.48 (t, 2H), 3.07-2.97 (m, 1H), 2.89-2.80 (m, 1H), 2.61-2.46 (m, 1H), 2.22-2.12 (m, 7H), 1.74 (tdd, 1H) |
| A34 | 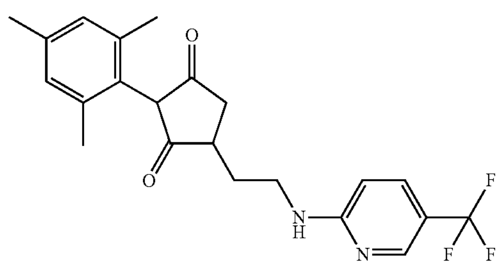 [SMILES: Cc1cc(C)c(C2C(=O)CC(CCNc3ccc(C(F)(F)F)cn3)C2=O)c(C)c1] | 1HNMR(400 MHz, d4-methanol) 8.21 (s, 1H), 7.62-7.53 (m, 1H), 6.90-6.81 (m, 2H), 6.60 (d, 1H), 3.63-3.45 (m, 2H), 2.96-2.80 (m, 2H), 2.48-2.39 (m, 1H), 2.24 (s, 3H), 2.20-2.09 (m, 1H), 2.05 (s, 6H), 1.84-1.68 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A35 | 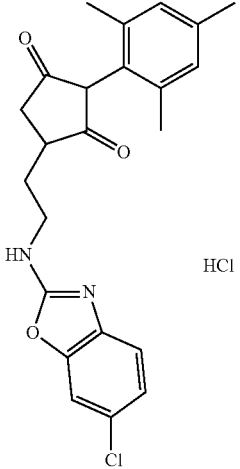 [SMILES: Cc1cc(C)c(C2C(=O)CC(CCNc3nc4ccc(Cl)cc4o3)C2=O)c(C)c1 ; Cl] | 1HNMR(400 MHz, d4-methanol) 7.71 (s, 1H), 7.48-7.38 (m, 2H), 6.87 (s, 2H), 3.86-3.68 (m, 2H), 3.02 (dd, 1H), 2.95-2.84 (m, 1H), 2.58-2.47 (m, 1H), 2.30-2.26 (m, 1H), 2.26-2.20 (m, 3H), 2.06 (d, 6H), 1.98-1.88 (m, 1H) |
| A36 | 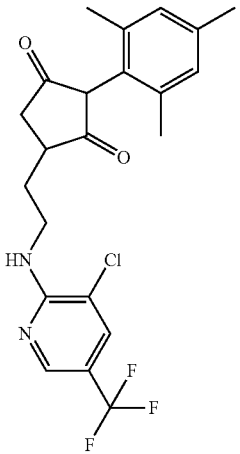 [SMILES: Cc1cc(C)c(C2C(=O)CC(CCNc3ncc(C(F)(F)F)cc3Cl)C2=O)c(C)c1] | 1HNMR(400 MHz, d4-methanol) 8.33-8.23 (m, 1H), 8.20-8.08 (m, 1H), 6.88 (s, 2H), 3.86-3.77 (m, 1H), 3.74-3.67 (m, 1H), 3.02 (dd, 1H), 2.90-2.79 (m, 1H), 2.56-2.43 (m, 1H), 2.26 (s, 3H), 2.15 (qd, 1H), 2.09-2.03 (m, 6H), 2.00-1.89 (m, 1H) |
| A37 | 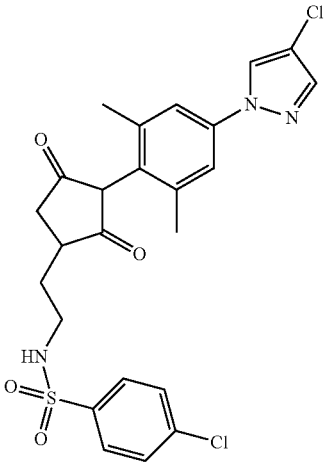 [SMILES: Cc1cc(-n2cc(Cl)cn2)cc(C)c1C1C(=O)CC(CCNS(=O)(=O)c2ccc(Cl)cc2)C1=O] | 1HNMR(400 MHz, dMSO-d6) 7.62 (s, 1H), 7.08 (d, 2H), 6.91 (s, 1H), 6.84 (d, 2H), 6.68 (s, 2H), 2.25 (t, 2H), 2.11 (dd, 1H), 2.01 (br.s., 1H), 1.60 (d, 1H), 1.42-1.32 (m, 6H), 1.24 (s, 1H), 0.83 (d, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A38 | 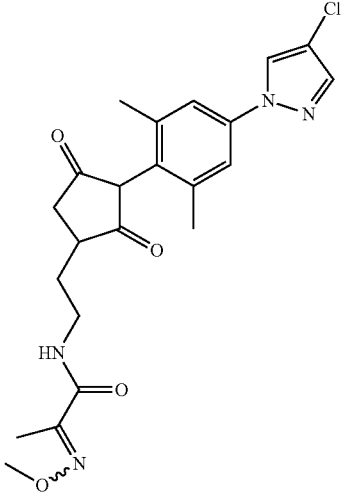 [SMILES: CON=C(C)C(=O)NCCC1CC(=O)C(c2c(C)cc(-n3cc(Cl)cn3)cc2C)C1=O] | 1HNMR(400 MHz, CDCl3) 7.82 (s, 1H), 7.55 (s, 1H), 7.19 (s, 3H), 3.96 (s, 3H), 3.69-3.44 (m, 1H), 3.42-3.22 (m, 1H), 2.95-2.64 (m, 2H), 2.33-2.16 (m, 1H), 2.16-1.87 (m, 10H), 1.87-1.62 (m, 1H) |
| A39 | 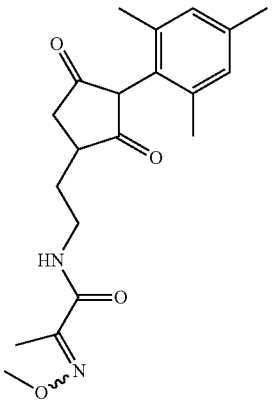 | 1HNMR(400 MHz, CDCl3) 7.31-7.13 (m, 1H), 6.82 (s, 2H), 3.96 (s, 3H), 3.63-3.42 (m, 1H), 3.40-3.19 (m, 1H), 2.73 (d, 2H), 2.26-1.84 (m, 14H), 1.82-1.67 (m, 1H) |
| A40 | 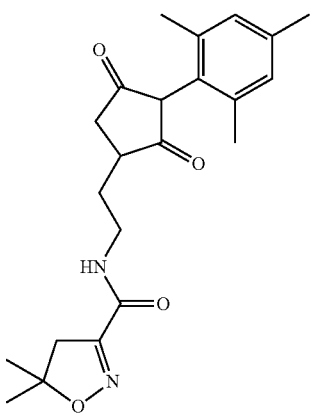 | 1HNMR(400 MHz, CDCl3) 7.43-7.29 (m, 1H), 6.82 (s, 2H), 3.63-3.22 (m, 2H), 2.93 (s, 2H), 2.82-2.59 (m, 2H), 2.29-2.11 (m, 4H), 2.10-1.63 (m, 8H), 1.43 (d, 6H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A41 | 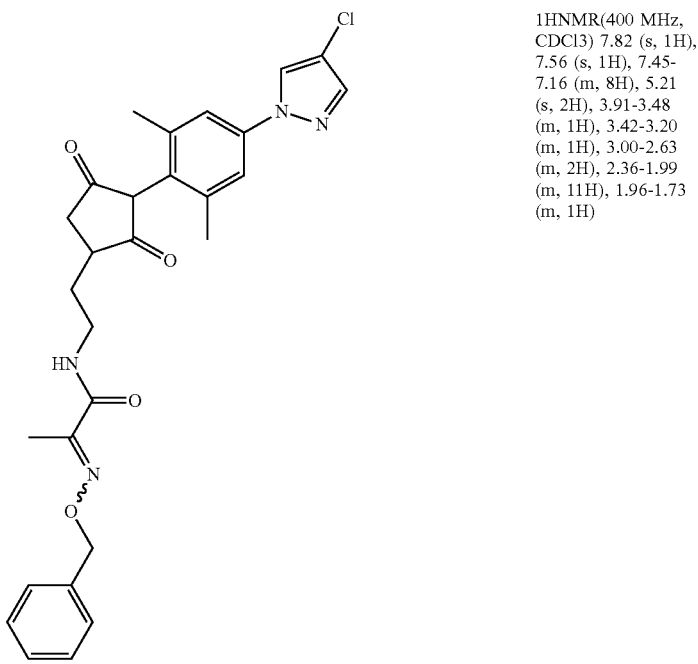 | 1HNMR(400 MHz, CDCl3) 7.82 (s, 1H), 7.56 (s, 1H), 7.45-7.16 (m, 8H), 5.21 (s, 2H), 3.91-3.48 (m, 1H), 3.42-3.20 (m, 1H), 3.00-2.63 (m, 2H), 2.36-1.99 (m, 11H), 1.96-1.73 (m, 1H) |
| A42 | 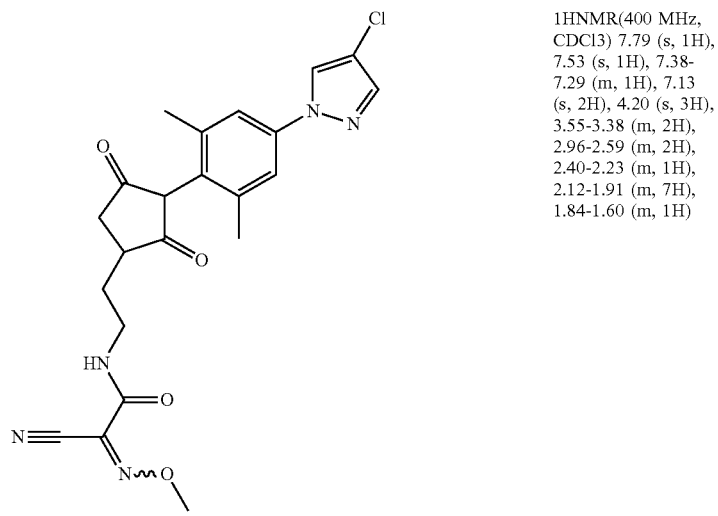 | 1HNMR(400 MHz, CDCl3) 7.79 (s, 1H), 7.53 (s, 1H), 7.38-7.29 (m, 1H), 7.13 (s, 2H), 4.20 (s, 3H), 3.55-3.38 (m, 2H), 2.96-2.59 (m, 2H), 2.40-2.23 (m, 1H), 2.12-1.91 (m, 7H), 1.84-1.60 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A43 | 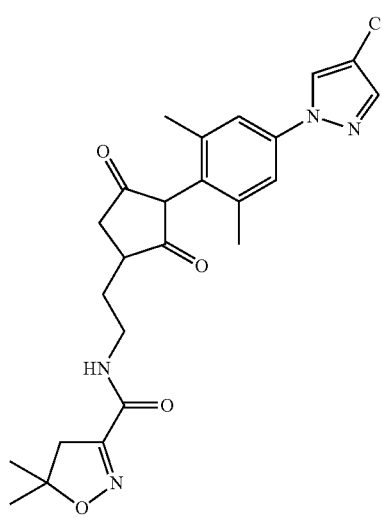 | 1HNMR(400 MHz, CDCl3) 7.83 (s, 1H), 7.57 (s, 1H), 7.46-7.33 (m, 1H), 7.22 (s, 2H), 3.41 (s, 2H), 2.96 (s, 2H), 2.90-2.68 (m, 2H), 2.33-2.20 (m, 1H), 2.16-1.88 (m, 7H), 1.87-1.67 (m, 1H), 1.44 (s, 6H) |
| A44 | 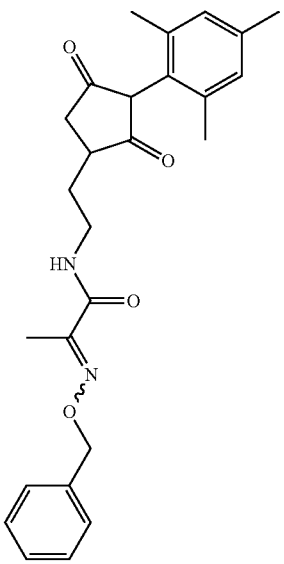 [SMILES: CC(=NOCc1ccccc1)C(=O)NCCC1CC(=O)C(c2c(C)cc(C)cc2C)C1=O] | 1HNMR(400 MHz, CDCl3) 7.45-7.09 (m, 6H), 6.82 (s, 2H), 5.19 (s, 2H), 3.67-3.40 (m, 1H), 3.39-3.20 (m, 1H), 2.86-2.55 (m, 2H), 2.24-1.97 (m, 13H), 1.95-1.65 (m, 2H) |
| A45 | 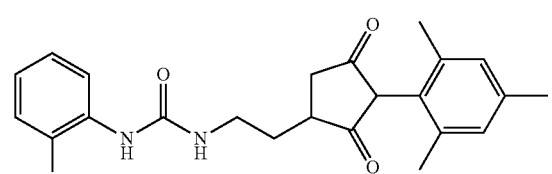 | 1H NMR (400 MHz, d4-methanol) 8.04-7.93 (m, 1H), 7.18-7.06 (m, 2H), 7.06-6.95 (m, 1H), 6.89 (s, 2H), 3.46-3.36 (m, 2H), 2.95 (dd, 1H), 2.82 (br. s., 1H), 2.55-2.42 (m, 1H), 2.34-2.21 (m, 3H), 2.19-2.02 (m, 7H), 1.77-1.60 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A46 | 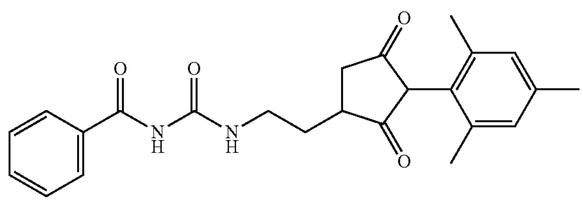 | 1H NMR (400 MHz, d4-methanol) 7.95-7.84 (m, 2H), 7.64-7.54 (m, 1H), 7.54-7.45 (m, 2H), 6.86 (s, 2H), 3.55-3.45 (m, 2H), 2.93 (dd, 1H), 2.87-2.77 (m, 1H), 2.48 (dd, 1H), 2.24 (s, 3H), 2.22-2.11 (m, 1H), 2.10-1.99 (m, 6H), 1.72 (tdd, 1H) |
| A47 | 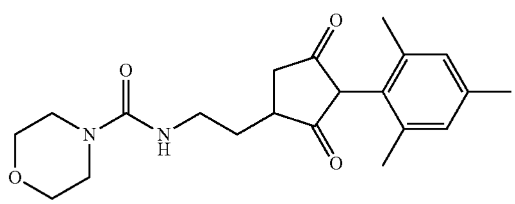 [SMILES: Cc1cc(C)c(C2C(=O)CC(CCNC(=O)N3CCOCC3)C2=O)c(C)c1] | 1H NMR (400 MHz, d4-methanol) 6.89 (s, 2H), 3.72-3.61 (m, 4H), 3.45-3.26 (m, 6H), 2.94 (dd, 1H), 2.83-2.73 (m, 1H), 2.45 (dd, 1H), 2.28 (s, 3H), 2.15-1.99 (m, 7H), 1.75-1.58 (m, 1H) |
| A48 | 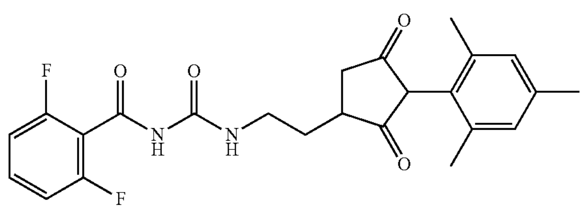 [SMILES: Cc1cc(C)c(C2C(=O)CC(CCNC(=O)NC(=O)c3c(F)cccc3F)C2=O)c(C)c1] | 1H NMR (400 MHz, d4-methanol) 7.53 (tt, 1H), 7.14-7.02 (m, 2H), 6.87 (s, 2H), 3.56-3.41 (m, 2H), 2.93 (dd, 1H), 2.85-2.74 (m, 1H), 2.54-2.40 (m, 1H), 2.29-2.22 (m, 3H), 2.22-2.10 (m, 1H), 2.08-2.03 (m, 6H), 1.80-1.64 (m, 1H) |
| A49 | 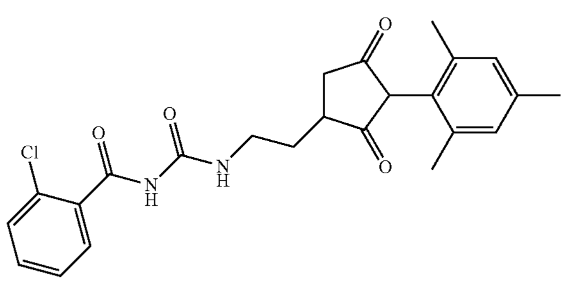 [SMILES: Cc1cc(C)c(C2C(=O)CC(CCNC(=O)NC(=O)c3ccccc3Cl)C2=O)c(C)c1] | 1H NMR (400 MHz, d4-methanol) 7.51-7.30 (m, 4H), 6.83 (s, 2H), 3.50-3.38 (m, 2H), 2.94-2.83 (m, 1H), 2.77 (dd, 1H), 2.50-2.36 (m, 1H), 2.26-2.18 (m, 3H), 2.18-2.07 (m, 1H), 2.05-1.97 (m, 6H), 1.68 (tdd, 1H) |
| A50 | 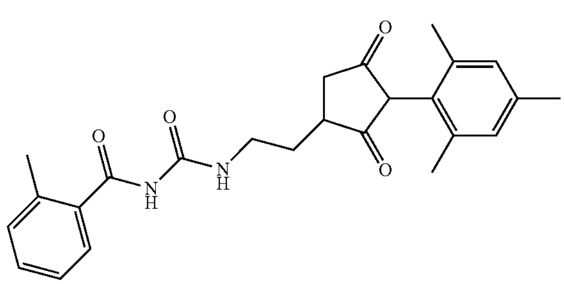 [SMILES: Cc1cc(C)c(C2C(=O)CC(CCNC(=O)NC(=O)c3ccccc3C)C2=O)c(C)c1] | 1H NMR (400 MHz, d4-methanol) 7.44-7.29 (m, 2H), 7.27-7.16 (m, 2H), 6.83 (s, 2H), 3.47-3.39 (m, 2H), 2.93-2.82 (m, 1H), 2.80-2.70 (m, 1H), 2.47-2.34 (m, 4H), 2.21 (s, 3H), 2.18-2.07 (m, 1H), 2.05-1.96 (m, 6H), 1.74-1.59 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A51 | 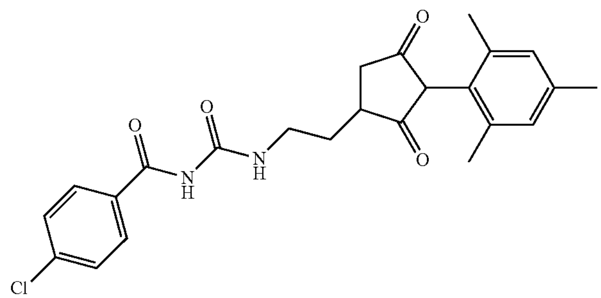 [SMILES: Cc1cc(C)c(C2C(=O)CC(CCNC(=O)NC(=O)c3ccc(Cl)cc3)C2=O)c(C)c1] | 1H NMR (400 MHz, d4-methanol) 7.97-7.83 (m, 2H), 7.59-7.48 (m, 2H), 6.89 (s, 2H), 3.53 (t, 1H), 2.96 (dd, 1H), 2.89-2.74 (m, 1H), 2.56-2.44 (m, 1H), 2.32-2.13 (m, 5H), 2.12-1.97 (m, 6H), 1.75 (tdd, 1H) |
| A52 | 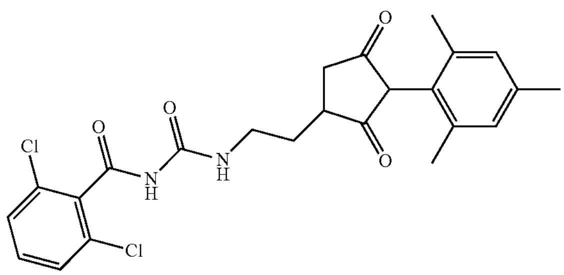 [SMILES: Cc1cc(C)c(C2C(=O)CC(CCNC(=O)NC(=O)c3c(Cl)cccc3Cl)C2=O)c(C)c1] | 1H NMR (400 MHz, d4-methanol) 7.45-7.28 (m, 3H), 6.83 (s, 2H), 3.50-3.36 (m, 2H), 2.88 (dd, 1H), 2.75 (br. s., 1H), 2.44 (d, 1H), 2.25-2.08 (m, 4H), 2.06-1.93 (m, 6H), 1.75-1.61 (m, 1H) |
| A53 | 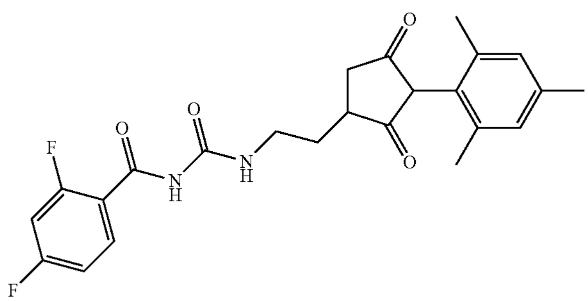 [SMILES: Cc1cc(C)c(C2C(=O)CC(CCNC(=O)NC(=O)c3ccc(F)cc3F)C2=O)c(C)c1] | 1H NMR (400 MHz, d4-methanol) 7.90-7.69 (m, 1H), 7.20-7.04 (m, 2H), 6.89 (s, 2H), 3.57-3.42 (m, 2H), 2.96 (dd, 1H), 2.88-2.76 (m, 1H), 2.51 (dd, 1H), 2.34-2.14 (m, 4H), 2.13-2.01 (m, 6H), 1.75 (tdd, 1H) |
| A54 | 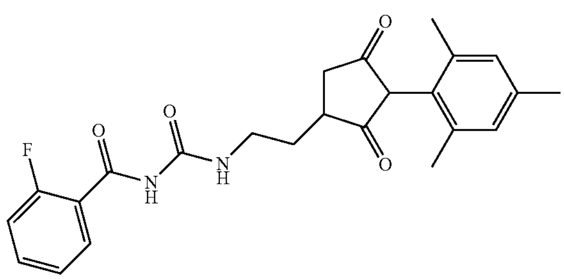 | 1H NMR (400 MHz, d4-methanol) 7.71 (dt, 1H), 7.58-7.48 (m, 1H), 7.30-7.12 (m, 2H), 6.82 (s, 2H), 3.50-3.39 (m, 2H), 2.88 (dd, 1H), 2.80-2.69 (m, 1H), 2.43 (dd, 1H), 2.20 (s, 3H), 2.18-2.05 (m, 1H), 2.05-1.96 (m, 6H), 1.67 (tdd, 1H) |
| A55 | 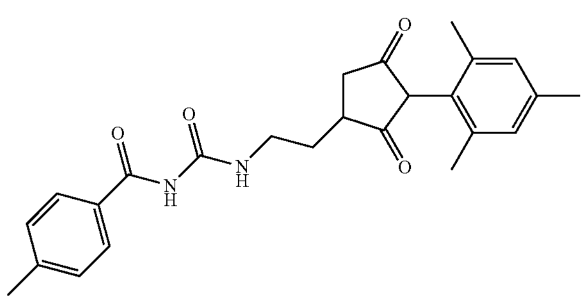 | 1H NMR (400 MHz, d4-methanol) 7.88-7.76 (m, 2H), 7.40-7.26 (m, 2H), 6.89 (s, 2H), 3.58-3.47 (m, 2H), 2.96 (dd, 1H), 2.89-2.78 (m, 1H), 2.57-2.46 (m, 1H), 2.44 (s, 3H), 2.27 (s, 3H), 2.24-2.13 (m, 1H), 2.11-2.02 (m, 6H), 1.75 (tdd, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A56 | 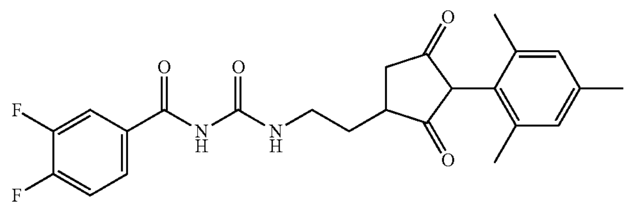 [SMILES: Cc1cc(C)c(C2C(=O)CC(CCNC(=O)NC(=O)c3ccc(F)c(F)c3)C2=O)c(C)c1] | 1H NMR (400 MHz, d4-methanol) 7.97-7.72 (m, 2H), 7.50-7.38 (m, 1H), 6.89 (s, 2H), 3.53 (t, 2H), 2.96 (dd, 1H), 2.88-2.78 (m, 1H), 2.51 (dd, 1H), 2.33-2.14 (m, 4H), 2.08 (s, 6H), 1.75 (tdd, 1H) |
| A57 | 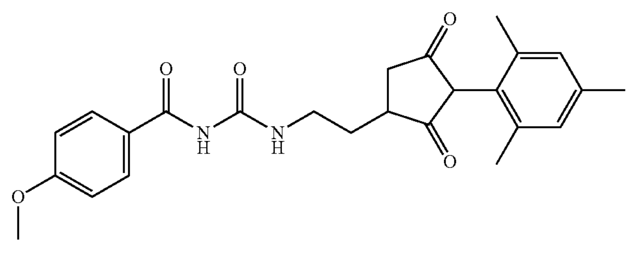 [SMILES: COc1ccc(C(=O)NC(=O)NCCC2CC(=O)C(c3c(C)cc(C)cc3C)C2=O)cc1] | 1H NMR (400 MHz, d4-methanol) 7.97-7.87 (m, 2H), 7.08-6.99 (m, 2H), 6.89 (s, 2H), 3.91-3.86 (m, 3H), 3.57-3.48 (m, 2H), 2.96 (dd, 1H), 2.89-2.78 (m, 1H), 2.51 (dd, 1H), 2.27 (s, 3H), 2.24-2.13 (m, 1H), 2.11-2.03 (m, 6H), 1.75 (tdd, 1H) |
| A58 | 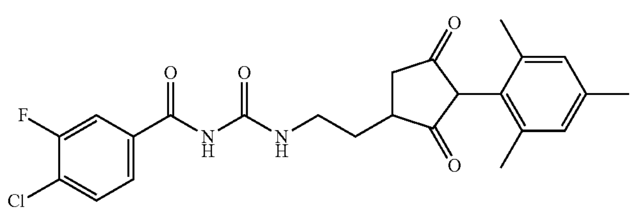 [SMILES: Cc1cc(C)c(C2C(=O)CC(CCNC(=O)NC(=O)c3ccc(Cl)c(F)c3)C2=O)c(C)c1] | 1H NMR (400 MHz, d4-methanol) 8.15-8.03 (m, 1H), 7.89-7.77 (m, 1H), 7.71-7.65 (m, 1H), 6.88 (s, 2H), 3.53 (t, 2H), 3.01-2.90 (m, 1H), 2.89-2.77 (m, 1H), 2.56-2.43 (m, 1H), 2.31-2.15 (m, 4H), 2.11-1.98 (m, 6H), 1.75 (tdd, 1H) |
| A59 | 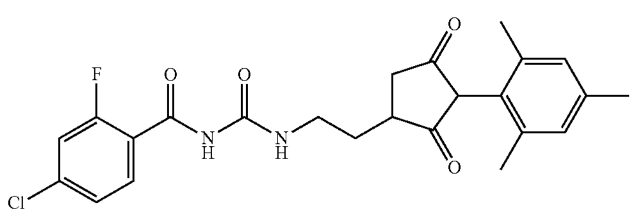 [SMILES: Cc1cc(C)c(C2C(=O)CC(CCNC(=O)NC(=O)c3ccc(Cl)cc3F)C2=O)c(C)c1] | 1H NMR (400 MHz, d4-methanol) 7.69 (t, 1H), 7.37-7.25 (m, 1H), 6.82 (s, 2H), 6.87 (br. s., 1H), 3.49-3.39 (m, 2H), 2.88 (dd, 1H), 2.80-2.70 (m, 1H), 2.43 (dd, 1H), 2.24-2.07 (m, 4H), 2.06-1.95 (m, 6H), 1.67 (tdd, 1H) |
| A60 | 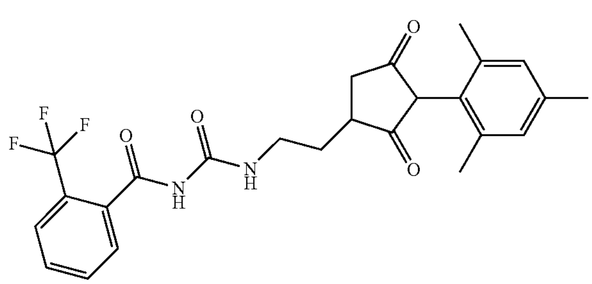 [SMILES: Cc1cc(C)c(C2C(=O)CC(CCNC(=O)NC(=O)c3ccccc3C(F)(F)F)C2=O)c(C)c1] | 1H NMR (400 MHz, d4-methanol) 7.78-7.71 (m, 1H), 7.70-7.58 (m, 2H), 7.55 (d, 1H), 6.83 (s, 2H), 3.49-3.39 (m, 2H), 2.88 (dd, 1H), 2.80-2.70 (m, 1H), 2.43 (dd, 1H), 2.21 (s, 3H), 2.18-2.08 (m, 1H), 2.03 (s, 6H), 1.67 (tdd, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A61 | 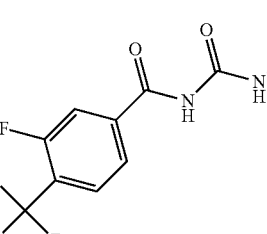 | 1H NMR (400 MHz, d4-methanol) 7.89-7.71 (m, 3H), 6.81 (s, 2H), 3.51-3.39 (m, 2H), 2.89 (dd, 1H), 2.82-2.71 (m, 1H), 2.50-2.35 (m, 1H), 2.24-2.06 (m, 4H), 2.04-1.95 (m, 6H), 1.68 (tdd, 1H) |
| A62 | 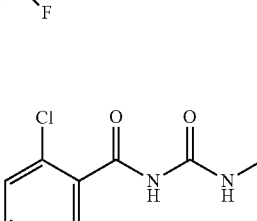 | 1H NMR (400 MHz, d4-methanol) 7.82 (d, 1H), 7.77-7.69 (m, 1H), 7.68-7.60 (m, 1H), 6.87-6.78 (m, 2H), 3.49-3.39 (m, 2H), 2.88 (dd, 1H), 2.82-2.70 (m, 1H), 2.43 (dd, 1H), 2.24-2.06 (m, 4H), 2.02 (s, 6H), 1.75-1.60 (m, 1H) |
| A63 | 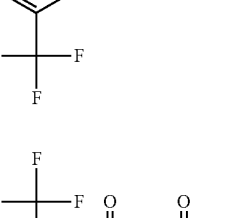 | 1H NMR (400 MHz, d4-methanol) 7.79 (dd, 1H), 7.41-7.33 (m, 2H), 6.83 (s, 2H), 3.48-3.38 (m, 2H), 2.88 (dd, 1H), 2.79-2.72 (m, 1H), 2.43 (dd, 1H), 2.21 (s, 3H), 2.18-2.07 (m, 1H), 2.02 (s, 6H), 1.67 (td, 1H) |
| A64 | 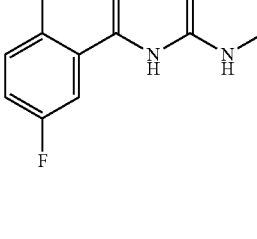 | 1H NMR (400 MHz, d4-methanol) 7.28 (d, 2H), 6.90 (s, 2H), 3.58-3.48 (m, 2H), 3.02-2.88 (m, 1H), 2.87-2.76 (m, 1H), 2.51 (dd, 1H), 2.33-2.24 (m, 3H), 2.22-2.12 (m, 1H), 2.08 (s, 6H), 1.82-1.66 (m, 1H) |
| A65 | 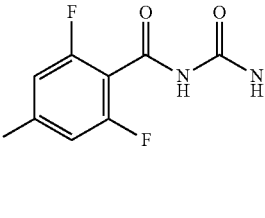 | 1H NMR (400 MHz, d4-methanol) 7.64 (d, 1H), 7.44 (d, 1H), 6.82 (s, 2H), 3.47-3.38 (m, 2H), 2.95-2.81 (m, 1H), 2.80-2.70 (m, 1H), 2.42 (dd, 1H), 2.21 (s, 3H), 2.17-2.06 (m, 1H), 2.05-1.95 (m, 6H), 1.67 (tdd, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A66 | 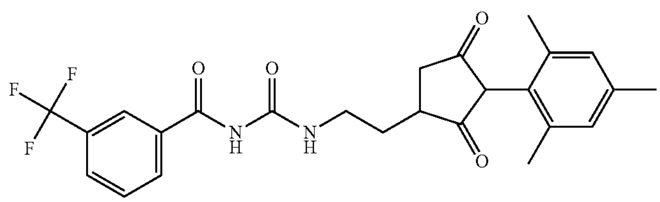 [SMILES: Cc1cc(C)c(C2C(=O)CC(CCNC(=O)NC(=O)c3cccc(C(F)(F)F)c3)C2=O)c(C)c1] | 1H NMR (400 MHz, d4-methanol) 8.19 (s, 1H), 8.12 (d, 1H), 7.86 (d, 1H), 7.66 (t, 1H), 6.81 (s, 2H), 3.52-3.42 (m, 2H), 2.89 (dd, 1H), 2.83-2.71 (m, 1H), 2.44 (dd, 1H), 2.20 (s, 4H), 2.00 (s, 6H), 1.69 (tdd, 1H) |
| A67 | 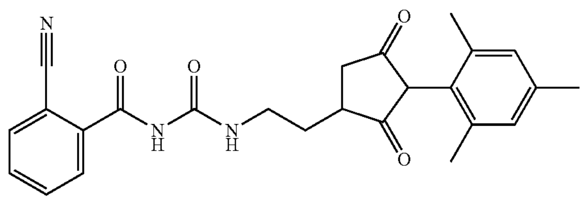 [SMILES: Cc1cc(C)c(C2C(=O)CC(CCNC(=O)NC(=O)c3ccccc3C#N)C2=O)c(C)c1] | 1H NMR (400 MHz, d4-methanol) 7.84 (dd, 1H), 7.80-7.74 (m, 1H), 7.70-7.64 (m, 1H), 6.89 (s, 2H), 3.53 (t, 2H), 2.96 (dd, 1H), 2.89-2.77 (m, 1H), 2.51 (dd, 1H), 2.28 (s, 3H), 2.25-2.13 (m, 1H), 2.08 (s, 6H), 1.75 (tdd, 1H) |
| A68 | 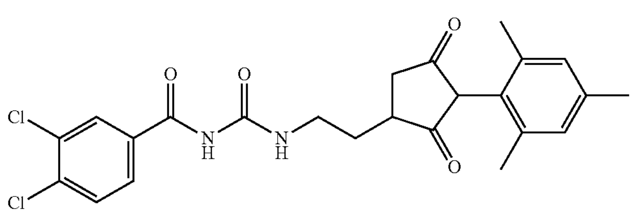 | 1H NMR (400 MHz, d4-methanol) 7.61 (dd, 1H), 7.54 (dd, 1H), 7.41 (dt, 1H), 6.83 (s, 2H), 3.47-3.39 (m, 2H), 2.94-2.82 (m, 1H), 2.80-2.69 (m, 1H), 2.47-2.36 (m, 1H), 2.21 (s, 3H), 2.18-2.07 (m, 1H), 2.02 (s, 6H), 1.67 (tdd, 1H) |
| A69 | 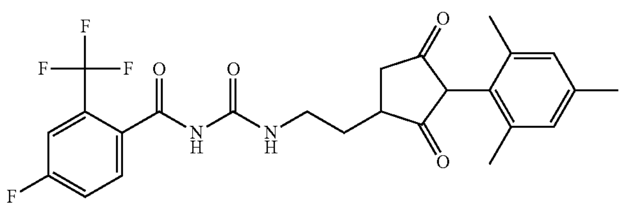 [SMILES: Cc1cc(C)c(C2C(=O)CC(CCNC(=O)NC(=O)c3ccc(F)cc3C(F)(F)F)C2=O)c(C)c1] | 1H NMR (400 MHz, d4-methanol) 7.97-7.85 (m, 1H), 7.71-7.60 (m, 2H), 6.90 (s, 2H), 3.59-3.49 (m, 2H), 3.03-2.90 (m, 1H), 2.85 (d, 1H), 2.56-2.45 (m, 1H), 2.31-2.14 (m, 4H), 2.12-2.03 (m, 6H), 1.76 (tdd, 1H) |
| A70 | 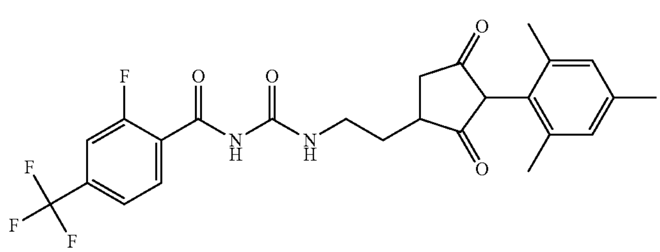 [SMILES: Cc1cc(C)c(C2C(=O)CC(CCNC(=O)NC(=O)c3ccc(C(F)(F)F)cc3F)C2=O)c(C)c1] | 1H NMR (400 MHz, d4-methanol) 8.10-7.98 (m, 2H), 7.43 (d, 2H), 6.89 (s, 2H), 3.58-3.49 (m, 2H), 2.96 (dd, 1H), 2.89-2.78 (m, 1H), 2.51 (dd, 1H), 2.31-2.13 (m, 4H), 2.11-2.01 (m, 6H), 1.75 (tdd, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A71 | 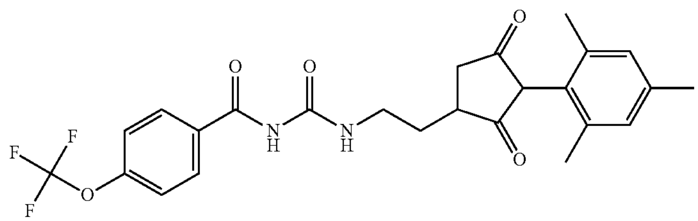 [SMILES: Cc1cc(C)c(C2C(=O)CC(CCNC(=O)NC(=O)c3ccc(OC(F)(F)F)cc3)C2=O)c(C)c1] | 1H NMR (400 MHz, d4-methanol) 8.13-8.02 (m, 2H), 7.83 (d, 2H), 6.88 (s, 2H), 3.54 (t,, 2H), 2.96 (dd, 1H), 2.88-2.78 (m, 1H), 2.51 (dd, 1H), 2.32-2.15 (m, 4H), 2.12-1.99 (m, 6H), 1.76 (tdd, 1H) |
| A72 | 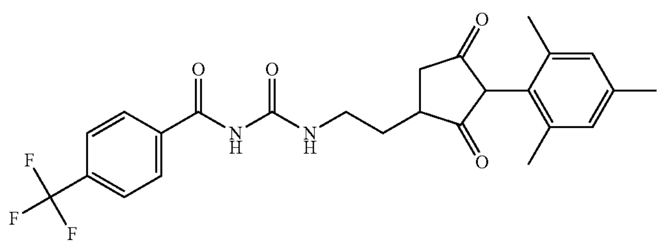 [SMILES: Cc1cc(C)c(C2C(=O)CC(CCNC(=O)NC(=O)c3ccc(C(F)(F)F)cc3)C2=O)c(C)c1] | 1H NMR (400 MHz, d4-methanol) 7.99-7.87 (m, 2H), 7.34 (t, 2H), 6.92-6.83 (m, 2H), 3.09-2.99 (m, 2H), 2.93-2.83 (m, 1H), 2.84-2.67 (m, 1H), 2.60 (dd, 0.3H), 2.43-2.32 (m, 0.7H), 2.27 (s, 3H), 2.10-1.96 (m, 7H), 1.69-1.52 (m, 1H) |
| A73 | 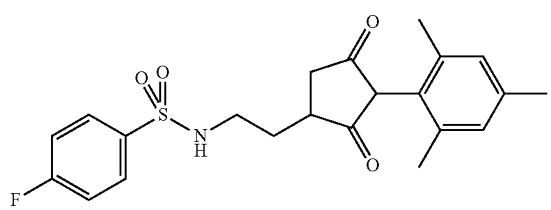 [SMILES: Cc1cc(C)c(C2C(=O)CC(CCNS(=O)(=O)c3ccc(F)cc3)C2=O)c(C)c1] | 1H NMR (400 MHz, d4-methanol) 8.05 (d, 2H), 7.89 (d, 2H), 6.84 (br. s., 2H), 3.04 (t, 2H), 2.88-2.66 (m, 2H), 2.30 (dd, 1H), 2.23 (s, 3H), 2.07-1.90 (m, 7H), 1.58 (qd, 1H) |
| A74 | 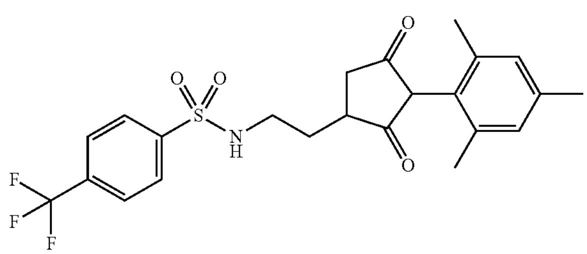 [SMILES: Cc1cc(C)c(C2C(=O)CC(CCNS(=O)(=O)c3ccc(C(F)(F)F)cc3)C2=O)c(C)c1] | 1H NMR (400 MHz, d4-methanol) 7.98 (dd, 1H), 7.83 (ddd, 1H), 7.46 (t, 1H), 6.84 (s, 2H), 3.02 (t, 2H), 2.88-2.67 (m, 2H), 2.31 (dd, 1H), 2.23 (s, 3H), 2.08-1.94 (m, 7H), 1.57 (tdd, 1H) |
| A75 | 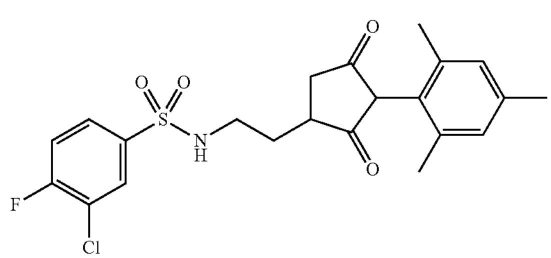 [SMILES: Cc1cc(C)c(C2C(=O)CC(CCNS(=O)(=O)c3ccc(F)c(Cl)c3)C2=O)c(C)c1] | 1H NMR (400 MHz, d4-methanol) 7.92-7.82 (m, 1H), 7.71-7.61 (m, 1H), 7.40-7.27 (m, 2H), 6.84 (br. s., 2H), 3.14-3.03 (m, 2H), 2.89-2.69 (m, 2H), 2.37-2.26 (m, 1H), 2.23 (s, 3H), 2.06-1.93 (m, 7H), 1.65-1.49 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A76 | 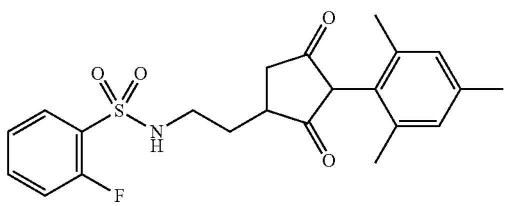 [SMILES: Cc1cc(C)c(C2C(=O)CC(CCNS(=O)(=O)c3ccccc3F)C2=O)c(C)c1] | 1H NMR (400 MHz, d4-methanol) 6.94-6.85 (m, 2H), 3.30-3.22 (m, 2H), 3.01-2.92 (m, 1H), 2.91-2.82 (m, 1H), 2.45 (dd, 1H), 2.31-2.25 (m, 3H), 2.21-2.10 (m, 1H), 2.09-2.04 (m, 6H), 1.74-1.57 (m, 1H), 1.37 (d, 6H), 1.20 (t, 1H) |
| A77 | 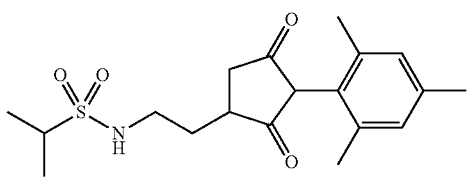 [SMILES: Cc1cc(C)c(C2C(=O)CC(CCNS(=O)(=O)C(C)C)C2=O)c(C)c1] | 1H NMR (400 MHz, d4-methanol) 8.03-7.94 (m, 1H), 7.80-7.70 (m, 2H), 6.88-6.80 (m, 2H), 3.07-2.97 (m, 2H), 2.91-2.64 (m, 2H), 2.58 (dd, 0.4H), 2.35 (dd, 0.6H), 2.23 (d, 3H), 2.07-1.93 (m, 7H), 1.65-1.49 (m, 1H) |
| A78 | 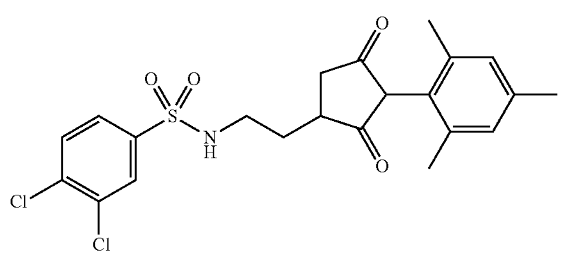 [SMILES: Cc1cc(C)c(C2C(=O)CC(CCNS(=O)(=O)c3ccc(Cl)c(Cl)c3)C2=O)c(C)c1] | 1H NMR (400 MHz, d4-methanol) 7.87-7.75 (m, 2H), 7.14-7.06 (m, 2H), 6.92-6.82 (m, 2H), 3.90 (s, 3H), 3.04-2.96 (m, 2H), 2.91-2.74 (m, 2H), 2.35 (dd, 1H), 2.27 (s, 3H), 2.09-1.96 (m, 7H), 1.65-1.51 (m, 1H) |
| A79 | 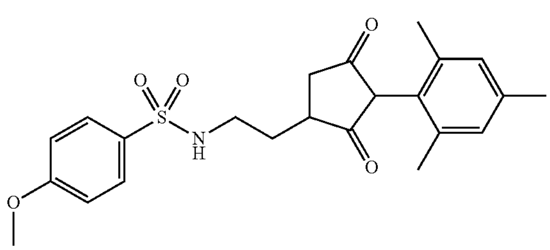 [SMILES: COc1ccc(S(=O)(=O)NCCC2CC(=O)C(c3c(C)cc(C)cc3C)C2=O)cc1] | 1H NMR (400 MHz, d4-methanol) 8.12-8.02 (m, 1H), 7.64-7.56 (m, 2H), 7.53-7.44 (m, 1H), 6.85 (br. s., 2H), 3.09-3.01 (m, 2H), 2.86-2.70 (m, 2H), 2.33-2.25 (m, 1H), 2.24 (s, 3H), 2.08-1.92 (m, 7H), 1.55 (dd, 1H) |
| A80 | 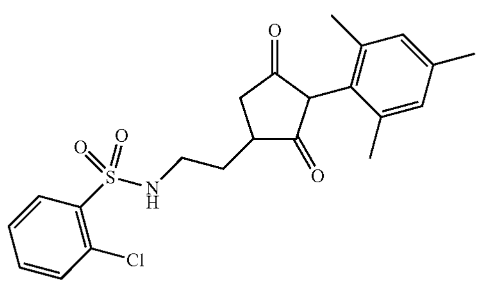 [SMILES: Cc1cc(C)c(C2C(=O)CC(CCNS(=O)(=O)c3ccccc3Cl)C2=O)c(C)c1] | 1H NMR (400 MHz, d4-methanol) 7.89-7.78 (m, 2H), 7.63-7.53 (m, 2H), 6.90-6.79 (m, 2H), 3.01 (t, 2H), 2.90-2.79 (m, 1H), 2.79-2.69 (m, 1H), 2.33 (dd, 1H), 2.24 (s, 3H), 2.06-1.93 (m, 7H), 1.57 (tdd, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A81 | 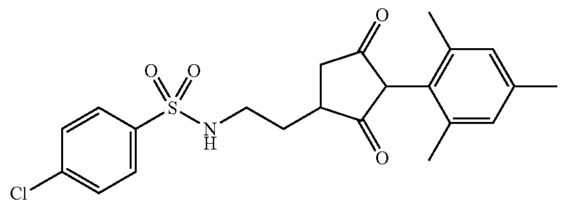 [SMILES: Cc1cc(C)c(C2C(=O)CC(CCNS(=O)(=O)c3ccc(Cl)cc3)C2=O)c(C)c1] | 1H NMR (400 MHz, d4-methanol) 7.81-7.73 (m, 1H), 7.63-7.56 (m, 1H), 7.18-7.11 (m, 1H), 6.85 (s, 2H), 3.12-3.02 (m, 2H), 2.90-2.72 (m, 2H), 2.40-2.30 (m, 1H), 2.24 (s, 3H), 2.11-1.96 (m, 7H), 1.60 (tdd, 1H) |
| A82 | 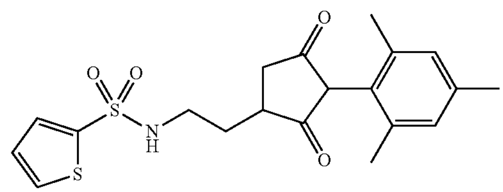 [SMILES: Cc1cc(C)c(C2C(=O)CC(CCNS(=O)(=O)c3cccs3)C2=O)c(C)c1] | 1H NMR (400 MHz, d4-methanol) 6.93-6.86 (m, 2H), 3.28-3.20 (m, 2H), 3.09 (q, 2H), 3.00-2.91 (m, 1H), 2.91-2.83 (m, 1H), 2.46 (dd, 1H), 2.28 (s, 3H), 2.22-2.11 (m, 1H), 2.10-2.04 (m, 6H), 1.74-1.59 (m, 1H), 1.35 (t, 3H) |
| A83 | 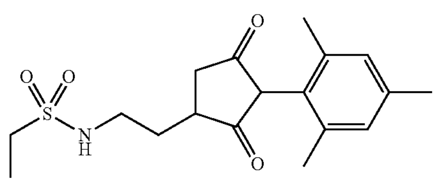 [SMILES: CCS(=O)(=O)NCCC1CC(=O)C(c2c(C)cc(C)cc2C)C1=O] | 1H NMR (400 MHz, d4-methanol) 8.04-7.95 (m, 1H), 7.65 (d, 1H), 7.47 (dd, 1H), 6.84-6.75 (m, 2H), 3.08-2.98 (m, 2H), 2.85-2.58 (m, 2H), 2.49 (dd, 0.2H), 2.28 (dd, 0.8H), 2.19 (s, 3H), 2.04-1.88 (m, 7H), 1.60-1.44 (m, 1H) |
| A84 | 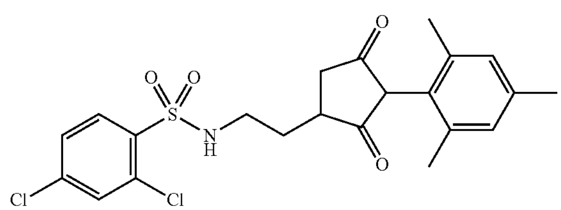 [SMILES: Cc1cc(C)c(C2C(=O)CC(CCNS(=O)(=O)c3ccc(Cl)cc3Cl)C2=O)c(C)c1] | 1H NMR (400 MHz, d4-methanol) 8.00-7.92 (m, 2H), 7.48 (d, 2H), 6.89-6.79 (m, 2H), 3.07-2.99 (m, 2H), 2.89-2.65 (m, 2H), 2.57 (dd, 0.4H), 2.34 (dd, 0.6H), 2.24 (s, 3H), 2.07-1.93 (m, 7H), 1.66-1.50 (m, 1H) |
| A85 | 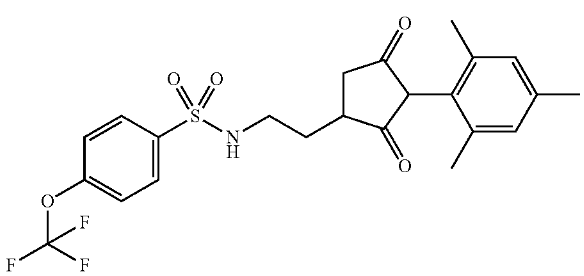 [SMILES: Cc1cc(C)c(C2C(=O)CC(CCNS(=O)(=O)c3ccc(OC(F)(F)F)cc3)C2=O)c(C)c1] | 1H NMR (400 MHz, d4-methanol) 8.21-8.13 (m, 1H), 7.94 (s, 1H), 7.80 (d, 2H), 6.85 (s, 2H), 3.12 (t, 2H), 2.90-2.80 (m, 1H), 2.80-2.71 (m, 1H), 2.34 (dd, 1H), 2.24 (s, 3H), 2.11-2.00 (m, 4H), 1.97 (s, 3H), 1.59 (tdd, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A86 | 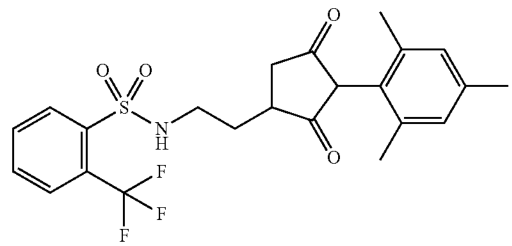 [SMILES: Cc1cc(C)c(C2C(=O)CC(CCNS(=O)(=O)c3ccccc3C(F)(F)F)C2=O)c(C)c1] | 1H NMR (400 MHz, d4-methanol) 7.95 (dd, 1H), 7.57-7.48 (m, 1H), 7.44-7.34 (m, 2H), 6.93-6.82 (m, 2H), 3.10-3.00 (m, 2H), 2.88-2.72 (m, 2H), 2.71-2.63 (m, 3H), 2.59-2.47 (m, 0.3H), 2.32 (dd, 0.7H), 2.27 (s, 3H), 2.10-1.95 (m, 7H), 1.64-1.49 (m, 1H) |
| A87 | 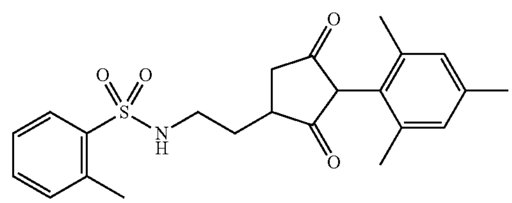 [SMILES: Cc1cc(C)c(C2C(=O)CC(CCNS(=O)(=O)c3ccccc3C)C2=O)c(C)c1] | 1H NMR (400 MHz, d4-methanol) 7.51-7.30 (m, 4H), 6.83 (s, 2H), 3.50-3.38 (m, 2H), 2.94-2.83 (m, 1H), 2.77 (dd, 1H), 2.50-2.36 (m, 1H), 2.26-2.18 (m, 3H), 2.18-2.07 (m, 1H), 2.05-1.97 (m, 6H), 1.68 (tdd, 1H) |
| A88 | 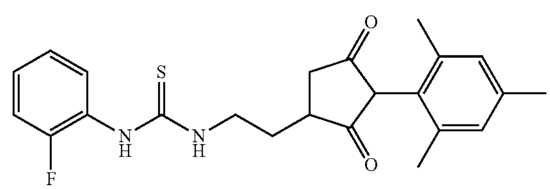 [SMILES: Cc1cc(C)c(C2C(=O)CC(CCNC(=S)Nc3ccccc3F)C2=O)c(C)c1] | 1H NMR (400 MHz, CD3OD) δ 7.50-7.71 (m, 4H) 6.85 (s, 2H) 3.65-3.79 (m, 2H) 2.88-2.99 (m, 1H) 2.71-2.83 (m, 1H) 2.56 (d, 1H) 2.24 (s, 3H) 1.98-2.20 (m, 8H) 1.68-1.81 (m, 1H) |
| A89 | 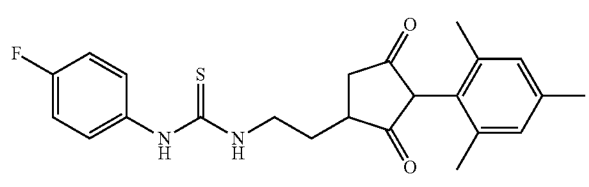 [SMILES: Cc1cc(C)c(C2C(=O)CC(CCNC(=S)Nc3ccc(F)cc3)C2=O)c(C)c1] | 1H NMR (400 MHz, CD3OD) δ 7.26-7.43 (m, 2H) 7.03-7.14 (m, 2H) 6.86 (s, 2H) 3.66-3.78 (m, 2H) 2.94 (dd, 1H) 2.76 (d, 1H) 2.55 (dd, 1H) 2.24 (s, 3H) 1.98-2.17 (m, 8H) 1.68-1.81 (m, 1H) |
| A90 | 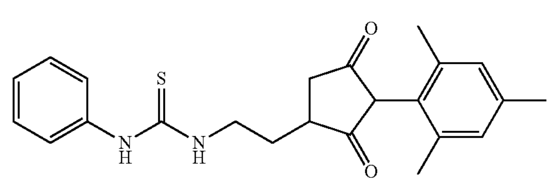 [SMILES: Cc1cc(C)c(C2C(=O)CC(CCNC(=S)Nc3ccccc3)C2=O)c(C)c1] | 1H NMR (400 MHz, CD3OD) δ 7.29-7.42 (m, 3H) 7.14-7.23 (m, 2H) 6.86 (s, 2H) 3.66-3.80 (m, 2H) 2.88-2.99 (m, 1H) 2.70-2.82 (m, 1H) 2.56 (d, 1H) 2.24 (s, 3H) 1.99-2.20 (m, 7H) 1.68-1.81 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A91 | 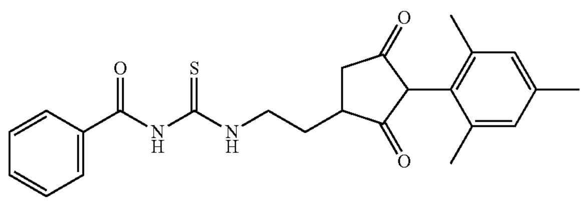 [SMILES: Cc1cc(C)c(C2C(=O)CC(CCNC(=S)NC(=O)c3ccccc3)C2=O)c(C)c1] | 1H NMR (400 MHz, CD3OD) δ 7.87-7.94 (m, 2H) 7.58-7.67 (m, 1H) 7.47-7.55 (m, 2H) 6.86 (s, 2H) 3.81-3.96 (m, 2H) 2.95 (dd, 1H) 2.83 (brs, 1H) 2.57 (dd, 1H) 2.20-2.32 (m, 4H) 1.99-2.08 (m, 7H) 1.81-1.94 (m, 1H) |
| A92 | 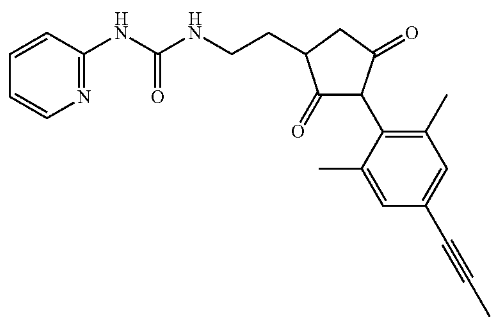 [SMILES: CC#Cc1cc(C)c(C2C(=O)CC(CCNC(=O)Nc3ccccn3)C2=O)c(C)c1] | 1HNMR (400 MHz, CD3OD) 8.30-8.19 (m, 2H), 7.39 (t, 1H), 7.33-7.25 (m, 1H), 7.10-7.01 (m, 2H), 3.36 (dd, 1H), 2.98 (dd, 1H), 2.81 (br.s., 1H), 2.55-2.42 (m, 1H), 2.15-2.08 (m, 2H), 2.08-2.03 (m, 6H), 2.00 (s, 3H), 1.73 (br.s., 1H) |
| A93 | HCl | 1HNMR (400 MHz, CD3OD) 8.32-8.22 (m, 2H), 7.46-7.26 (m, 1H), 6.92-6.81 (m, 2H), 3.49 (t, 2H), 2.99 (dd, 1H), 2.88-2.79 (m, 1H), 2.51 (dd, 1H), 2.29-2.23 (m, 3H), 2.22-2.11 (m, 1H), 2.08-2.03 (m, 6H), 1.79-1.70 (m, 1H) |
| A94 | 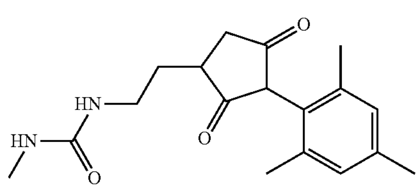 | 1HNMR (400 MHz, CD3OD) 6.88 (s, 2H), 3.51-3.33 (m, 2H), 2.98 (dd, 1H), 2.84-2.75 (m, 4H), 2.49-2.39 (m, 1H), 2.27-2.22 (m, 3H), 2.10-1.98 (m, 7H), 1.80-1.70 (m, 1H) |
| A95 | 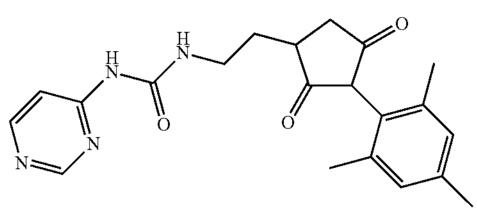 [SMILES: Cc1cc(C)c(C2C(=O)CC(CCNC(=O)Nc3ccncn3)C2=O)c(C)c1] | 1HNMR (400 MHz, CD3OD) 9.07-8.94 (m, 1H), 8.64-8.54 (m, 1H), 8.35-8.02 (m, 1H), 6.91-6.82 (m, 2H), 3.51-3.40 (m, 2H), 3.01-2.90 (m, 1H), 2.81 (dddd, 1H), 2.55-2.43 (m, 1H), 2.29-2.22 (m, 3H), 2.21-2.08 (m, 1H), 2.07-1.98 (m, 6H), 1.72 (tdd, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A96 | 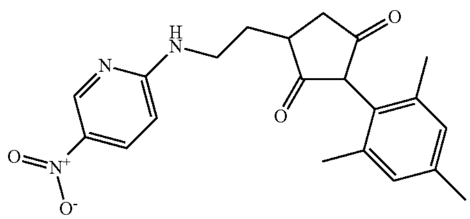 [SMILES: Cc1cc(C)c(C2C(=O)CC(CCNc3ccc([N+](=O)[O-])cn3)C2=O)c(C)c1] | 1H NMR (400 MHz, CD3OD) δ = 8.91 (d, 1H), 8.21 (d, 1H), 6.92-6.81 (m, 2H), 6.68 (d, 1H), 3.64 (d, 2H), 2.95 (dd, 1H), 2.84 (br. s., 1H), 2.56-2.39 (m, 1H), 2.30-2.22 (m, 3H), 2.22-2.10 (m, 1H), 2.09- 2.00 (m, 6H), 1.89-1.67 (m, 1H) |
| A97 | 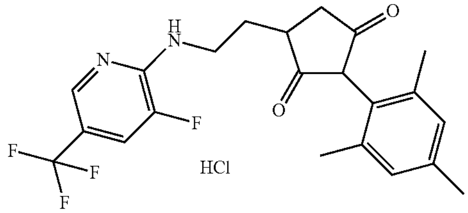 [SMILES: Cc1cc(C)c(C2C(=O)CC(CCNc3ncc(C(F)(F)F)cc3F)C2=O)c(C)c1 ; Cl] | 1HNMR (400 MHz, CD3OD) 8.16 (s, 1H), 7.99 (d, 1H), 6.88 (s, 2H), 3.82 (td, 1H), 3.69 (td, 1H), 3.03 (dd, 1H), 2.92-2.81 (m, 1H), 2.50 (dd, 1H), 2.26 (s, 3H), 2.20-2.12 (m, 1H), 2.10-2.01 (m, 6H), 2.01-1.89 (m, 1H) |
| A98 | 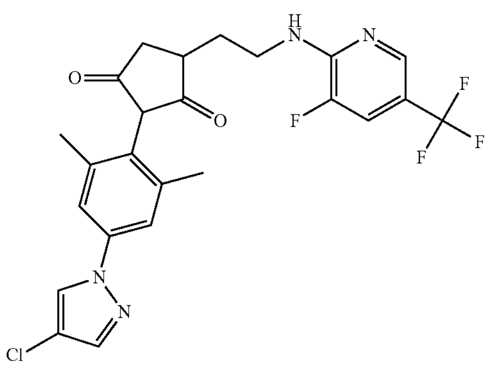 [SMILES: Cc1cc(-n2cc(Cl)cn2)cc(C)c1C1C(=O)CC(CCNc2ncc(C(F)(F)F)cc2F)C1=O] | 1HNMR (400 MHz, CD3OD) 8.34 (s, 1H), 8.17 (s, 1H), 8.06 (dd, 1H), 7.67 (s, 1H), 7.50-7.41 (m, 2H), 3.85 (td, 1H), 3.72 (td, 1H), 3.14-3.04 (m, 1H), 2.98-2.86 (m, 1H), 2.56 (dd, 1H), 2.24-2.15 (m, 7H), 2.07-1.94 (m, 1H) |
| A99 | 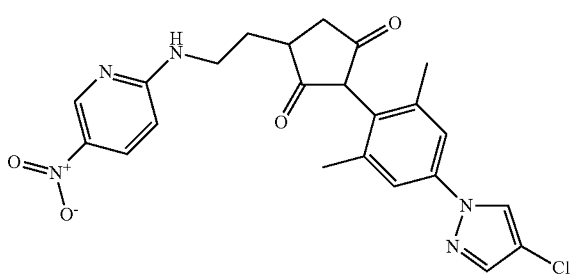 [SMILES: Cc1cc(-n2cc(Cl)cn2)cc(C)c1C1C(=O)CC(CCNc2ccc([N+](=O)[O-])cn2)C1=O] | 1HNMR (400 MHz, CD3OD) 9.11 (d, 1H), 8.31 (s, 1H), 8.22 (dd, 1H), 7.66-7.59 (m, 1H), 7.45-7.32 (m, 2H), 6.60-6.49 (m, 1H), 4.37-4.17 (m, 2H), 2.99-2.85 (m, 1H), 2.81-2.71 (m, 1H), 2.51 (dd, 1H), 2.37-2.27 (m, 1H), 2.20-2.13 (m, 6H), 1.98-1.87 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A100 | 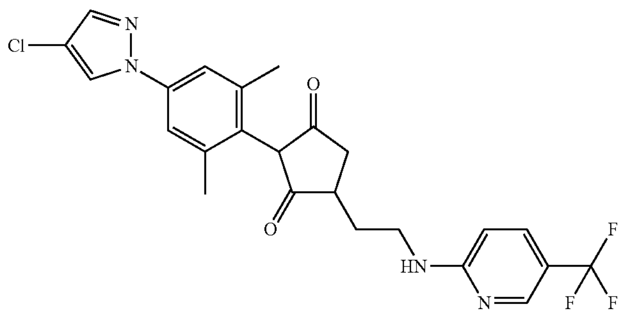 [SMILES: Cc1cc(-n2cc(Cl)cn2)cc(C)c1C1C(=O)CC(CCNc2ccc(C(F)(F)F)cn2)C1=O] | 1HNMR (400 MHz, CD3OD14ax426h1) 8.32 (s, 1H), 8.27-8.13 (m, 1H), 7.72-7.65 (m, 1H), 7.60 (dd, 1H), 7.45-7.37 (m, 2H), 6.69-6.48 (m, 1H), 3.71-3.44 (m, 2H), 3.03-2.84 (m, 2H), 2.49 (dd, 1H), 2.21-2.08 (m, 7H), 1.88-1.71 (m, 1H) |
| A101 | 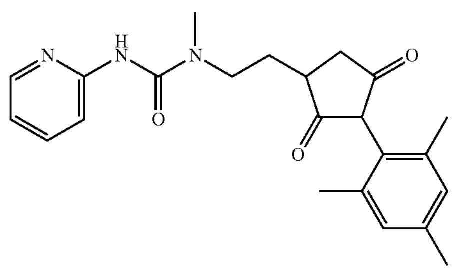 [SMILES: Cc1cc(C)c(C2C(=O)CC(CCN(C)C(=O)Nc3ccccn3)C2=O)c(C)c1] | 1HNMR (400 MHz, CDCl3) 8.26 (d, 2H), 7.57 (d, 1H), 7.41 (t, 1H), 6.89 (s, 2H), 3.22-2.98 (m, 5H), 2.83 (d, 1H), 2.48 (d, 1H), 2.32-2.23 (m, 4H), 2.13 (d, 8H), |
| A102 | 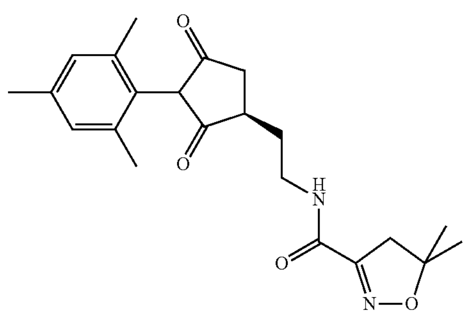 | 1H NMR (400 MHz, Methanol) δ = 6.95-6.77 (m, 2H), 3.55-3.37 (m, 2H), 2.98 (s, 2H), 2.95-2.85 (m, 1H), 2.84- 2.67 (m, 1H), 2.55-2.38 (m, 1H), 2.25 (s, 3H), 2.20-2.08 (m, 1H), 2.04 (d, J = 2.2 Hz, 6H), 1.77-1.57 (m, 1H), 1.41 (s, 6H) |
| A103 | 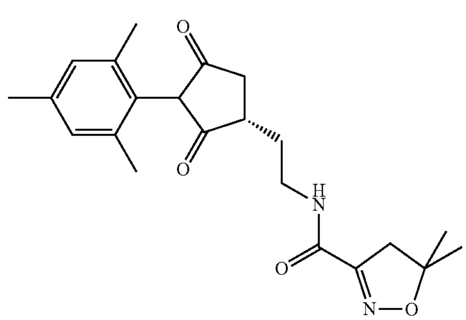 | 1H NMR (400 MHz, Methanol) δ = 6.95-6.77 (m, 2H), 3.55-3.37 (m, 2H), 2.98 (s, 2H), 2.95-2.85 (m, 1H), 2.84- 2.67 (m, 1H), 2.55-2.38 (m, 1H), 2.25 (s, 3H), 2.20-2.08 (m, 1H), 2.04 (d, J = 2.2 Hz, 6H), 1.77-1.57 (m, 1H), 1.41 (s, 6H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A104 | 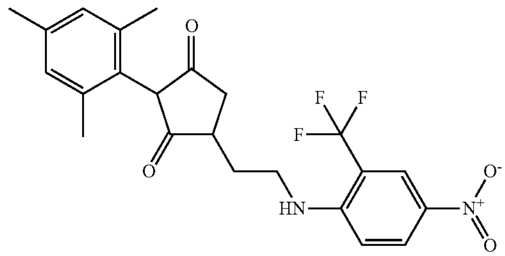 [SMILES: Cc1cc(C)c(C2C(=O)CC(CCNc3ccc([N+](=O)[O-])cc3C(F)(F)F)C2=O)c(C)c1] | 1H NMR (400 MHz, CD3OD) δ = 8.33 (d, J = 2.6 Hz, 1H), 8.28 (dd, J = 2.7, 9.3 Hz, 1H), 7.00 (d, J = 9.4 Hz, 1H), 6.87 (s, 2H), 3.66-3.48 (m, 2H), 2.94 (dd, J = 7.0, 17.9 Hz, 1H), 2.82 (br. s., 1H), 2.45 (dd, J = 2.3, 17.9 Hz, 1H), 2.29-2.22 (m, 3H), 2.22-2.14 (m, 1H), 2.06-2.00 (m, 6H), 1.88-1.75 (m, 1H) |
| A105 | 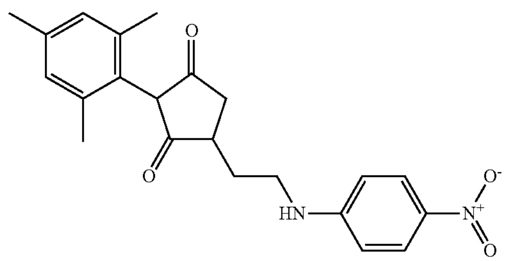 [SMILES: Cc1cc(C)c(C2C(=O)CC(CCNc3ccc([N+](=O)[O-])cc3)C2=O)c(C)c1] | 1HNMR (400 MHz, CD3OD) 8.07-7.99 (m, 2H), 6.87 (s, 2H), 6.69-6.60 (m, 2H), 3.42-3.35 (m, 2H), 2.95-2.81 (m, 2H), 2.46 (dd, 1H), 2.25 (s, 3H), 2.24-2.16 (m, 1H), 2.05 (s, 6H), 1.84-1.73 (m, 1H) |
| A106 | 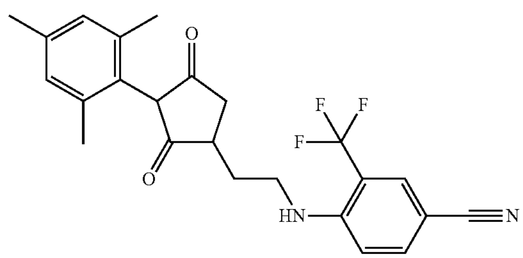 [SMILES: Cc1cc(C)c(C2C(=O)CC(CCNc3ccc(C#N)cc3C(F)(F)F)C2=O)c(C)c1] | 1HNMR (400 MHz, CD3OD) 7.75 (d, 1H), 7.71-7.60 (m, 1H), 6.98 (d, 1H), 6.87 (s, 2H), 3.56-3.40 (m, 2H), 2.93 (dd, 1H), 2.85-2.75 (m, 1H), 2.44 (dd, 1H), 2.25 (s, 3H), 2.20-2.10 (m, 1H), 2.05 (d, 6H), 1.87-1.71 (m, 1H) |
| A107 | 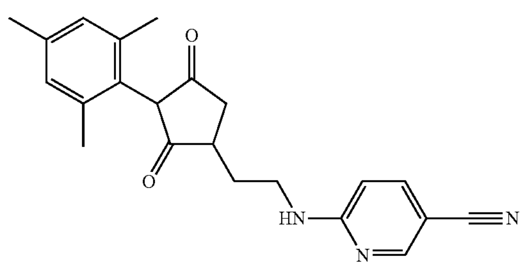 [SMILES: Cc1cc(C)c(C2C(=O)CC(CCNc3ccc(C#N)cn3)C2=O)c(C)c1] | 1HNMR (400 MHz, CD3OD) 8.31 (d, 1H), 7.58 (dd, 1H), 6.86 (s, 2H), 6.55 (d, 1H), 3.62-3.47 (m, 2H), 2.95-2.76 (m, 2H), 2.46 (d, 1H), 2.25 (s, 3H), 2.21-2.12 (m, 1H), 2.06-2.03 (m, 6H), 1.80-1.64 (m, 1H) |
| A108 | 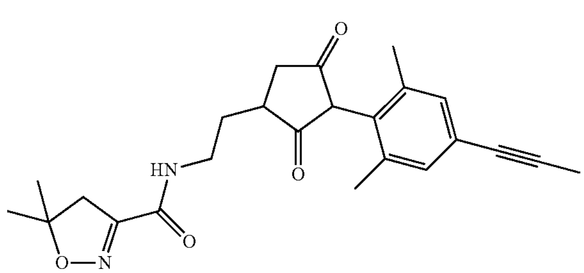 [SMILES: CC#Cc1cc(C)c(C2C(=O)CC(CCNC(=O)C3=NOC(C)(C)C3)C2=O)c(C)c1] | 1HNMR (400 MHz, CDCl3) 7.41-7.28 (m, 1H), 7.04 (s, 2H), 3.66-3.46 (m, 1H), 3.42-3.28 (m, 1H), 2.97-2.96 (m, 1H), 2.94 (s, 2H), 2.85-2.64 (m, 2H), 2.28-2.13 (m, 1H), 2.12-1.66 (m, 10H), 1.44 (d, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A109 | 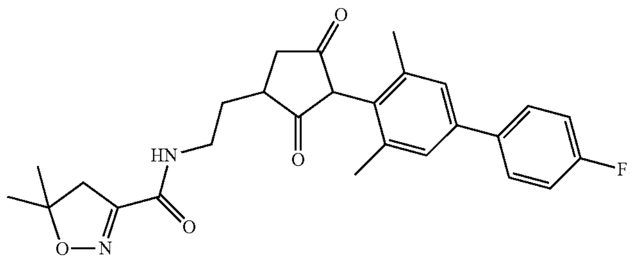 [SMILES: Cc1cc(-c2ccc(F)cc2)cc(C)c1C1C(=O)CC(CCNC(=O)C2=NOC(C)(C)C2)C1=O] | 1HNMR (400 MHz, CDCl3) 7.57-7.42 (m, 2H), 7.23 (s, 2H), 7.09 (s, 2H), 3.58-3.44 (m, 2H), 2.98 (s, 2H), 2.95-2.85 (m, 1H), 2.83-2.71 (m, 1H), 2.48-2.32 (m, 1H), 2.17 (d, 7H), 1.86-1.66 (m, 1H), 1.45 (s, 6H) |
| A110 | 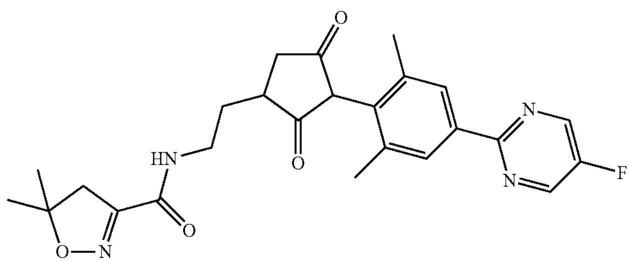 [SMILES: Cc1cc(-c2ncc(F)cn2)cc(C)c1C1C(=O)CC(CCNC(=O)C2=NOC(C)(C)C2)C1=O] | 1HNMR (400 MHz, CDCl3) 8.58 (s, 2H), 7.93 (s, 2H), 7.50-7.30 (m, 1H), 3.62-3.26 (m, 2H), 2.94 (s, 2H), 2.85-2.63 (m, 2H), 2.11 (d, 7H), 1.99-1.85 (m, 1H), 1.80-1.61 (m, 1H), 1.49-1.36 (m, 6H) |
| A111 | 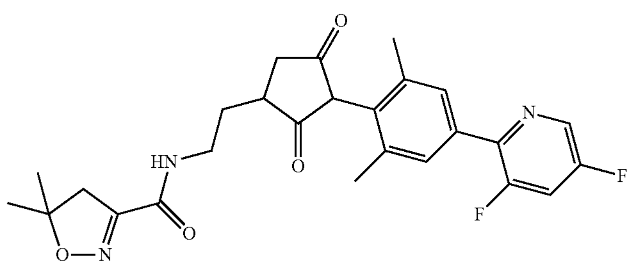 [SMILES: Cc1cc(-c2ncc(F)cc2F)cc(C)c1C1C(=O)CC(CCNC(=O)C2=NOC(C)(C)C2)C1=O] | 1HNMR (400 MHz, CDCl3) 8.32 (d, 1H), 7.56-6.89 (m, 4H), 3.65-3.24 (m, 2H), 2.95 (s, 2H), .85-2.6, (m, 2H), 22.11 (d, 7H), 2.00-1.85 (m, 1H), 1.82-1.65 (m, 1H), 1.53-1.36 (m, 6H) |
| A112 | 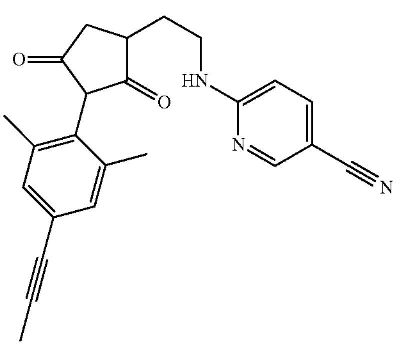 [SMILES: CC#Cc1cc(C)c(C2C(=O)CC(CCNc3ccc(C#N)cn3)C2=O)c(C)c1] | 1HNMR (400 MHz, CD3OD) 8.31 (dd, 1H), 7.58 (dd, 1H), 7.09-7.01 (m, 2H), 6.55 (dd, 1H), 3.61-3.47 (m, 2H), 2.95-2.87 (m, 1H), 2.81 (br.s., 1H), 2.52-2.39 (m, 1H), 2.25-2.11 (m, 1H), 2.05 (d, 6H), 2.01-1.98 (m, 3H), 1.79-1.63 (m, 1H) |
| A113 | 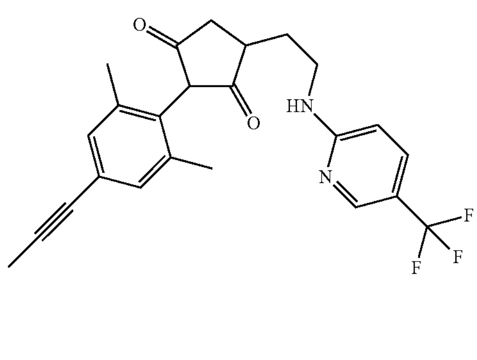 [SMILES: CC#Cc1cc(C)c(C2C(=O)CC(CCNc3ccc(C(F)(F)F)cn3)C2=O)c(C)c1] | 1HNMR (400 MHz, CD3OD) 8.24-8.15 (m, 1H), 7.60 (dd, 1H), 7.10-6.98 (m, 2H), 6.61 (d, 1H), 3.65-3.42 (m, 2H), 2.98-2.79 (m, 2H), 2.46 (dd, 1H), 2.22-2.09 (m, 1H), 2.08-2.03 (m, 6H), 1.99-1.96 (m, 3H), 1.85-1.57 (m, 1H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A114 | 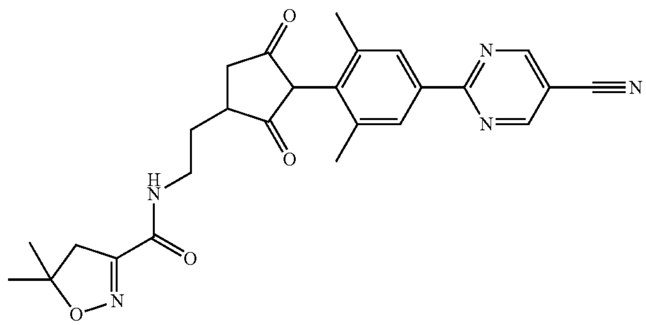 [SMILES: Cc1cc(-c2ncc(C#N)cn2)cc(C)c1C1C(=O)CC(CCNC(=O)C2=NOC(C)(C)C2)C1=O] | 1HNMR (400 MHz, CDCl3) 8.93 (s, 2H), 8.05 (s, 2H), 7.40-7.30 (m, 1H), 3.67-3.46 (m, 1H), 3.46-3.22 (m, 1H), 2.97 (s, 2H), 2.91-2.62 (m, 3H), 2.15 (d, 7H), 2.0-1.90 (m, 1H), 1.44 (d, 6H) |
| A115 | 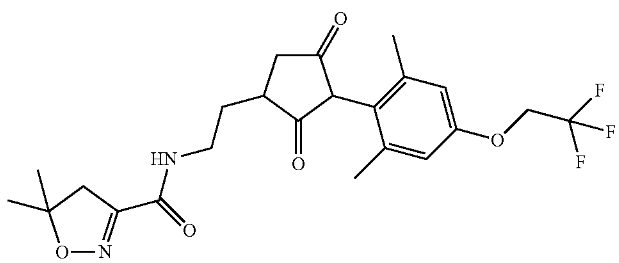 [SMILES: Cc1cc(OCC(F)(F)F)cc(C)c1C1C(=O)CC(CCNC(=O)C2=NOC(C)(C)C2)C1=O] | 1HNMR (400 MHz, CDCl3) 7.35 (s, 1H), 6.62 (s, 2H), 4.36-4.22 (m, 2H), 3.71-3.49 (m, 1H), 3.45-3.29 (m, 1H), 2.95 (s, 2H), 2.81 (d, 2H), 2.23 (d, 1H), 2.06 (s, 6H), 1.99-1.74 (m, 2H), 1.44 (d, 6H) |
| A116 | 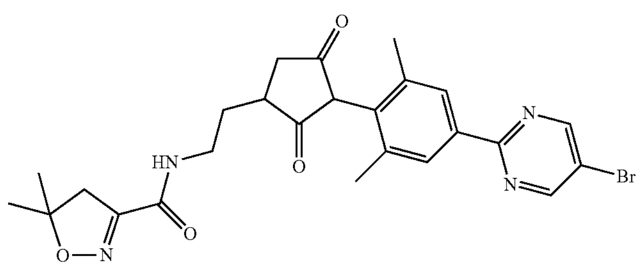 [SMILES: Cc1cc(-c2ncc(Br)cn2)cc(C)c1C1C(=O)CC(CCNC(=O)C2=NOC(C)(C)C2)C1=O] | 1HNMR (400 MHz, CDCl3) 8.80 (s, 2H), 8.10 (s, 2H), 4.09-3.88 (m, 1H), 3.44-3.23 (m, 1H), 3.01 (s, 4H), 2.26 (d, 7H), 1.96-1.78 (m, 1H), 1.49 (d, 7H) |
| A117 | 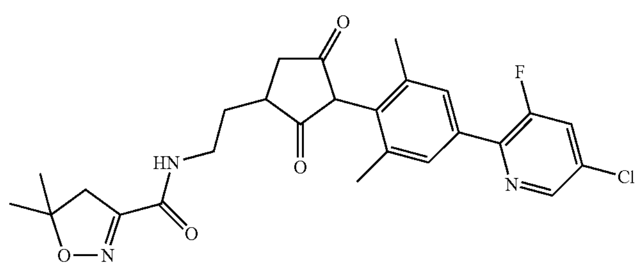 [SMILES: Cc1cc(-c2ncc(Cl)cc2F)cc(C)c1C1C(=O)CC(CCNC(=O)C2=NOC(C)(C)C2)C1=O] | 1HNMR (400 MHz, CDCl3) 8.36 (d, 1H), 7.55-7.13 (m, 4H), 3.64-3.26 (m, 2H), 2.95 (s, 2H), 2.85-2.65 (m, 2H), 2.30-2.04 (m, 7H), 2.01-1.87 (m, 1H), 1.84-1.65 (m, 1H), 1.52-1.35 (m, 6H) |
| A118 | 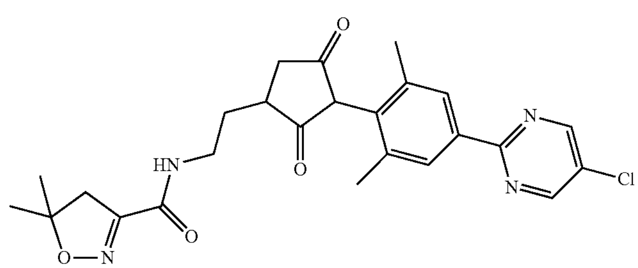 [SMILES: Cc1cc(-c2ncc(Cl)cn2)cc(C)c1C1C(=O)CC(CCNC(=O)C2=NOC(C)(C)C2)C1=O] | 1HNMR (400 MHz, CDCl3) 8.67 (s, 2H), 7.96 (br.s., 2H), 7.48-7.29 (m, 1H), 3.79-3.22 (m, 2H), 2.95 (s, 4H), 2.33-2.07 (m, 7H), 1.99-1.65 (m, 2H), 1.55-1.36 (m, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Chemical Structure | NMR |
|---|---|---|
| A119 | 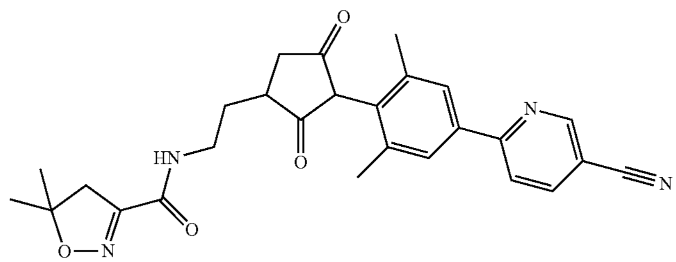 [SMILES: Cc1cc(-c2ccc(C#N)cn2)cc(C)c1C1C(=O)CC(CCNC(=O)C2=NOC(C)(C)C2)C1=O] | 1HNMR (400 MHz, CDCl3) 8.98-8.84 (m, 1H), 8.04-7.91 (m, 1H), 7.88-7.78 (m, 1H), 7.76-7.67 (m, 2H), 4.08-3.93 (m, 1H), 3.43-3.24 (m, 1H), 3.13-2.88 (m, 4H), 2.27 (d, 7H), 1.95-1.77 (m, 1H), 1.49 (d, 7H) |
| A120 | 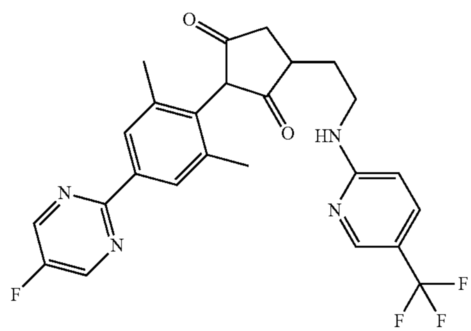 [SMILES: Cc1cc(-c2ncc(F)cn2)cc(C)c1C1C(=O)CC(CCNc2ccc(C(F)(F)F)cn2)C1=O] | 1HNMR (400 MHz, CD3OD) 8.80-8.69 (m, 2H), 8.29-8.17 (m, 1H), 8.13-8.02 (m, 2H), 7.60 (dd, 1H), 6.71-6.54 (m, 1H), 3.66-3.45 (m, 2H), 3.03-2.79 (m, 2H), 2.50 (dd, 1H), 2.25-2.11 (m, 7H), 1.85-1.73 (m, 1H) |
| A121 | 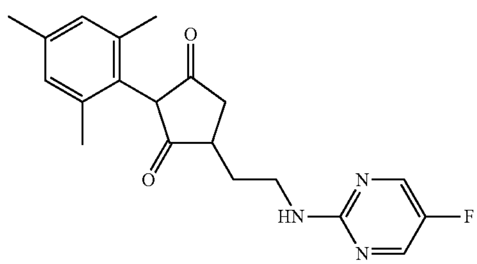 [SMILES: Cc1cc(C)c(C2C(=O)CC(CCNc3ncc(F)cn3)C2=O)c(C)c1] | 1HNMR (400 MHz, CD3OD) 8.22 (s, 2H), 6.90-6.64 (m, 2H), 3.57-3.45 (m, 2H), 2.93-2.75 (m, 2H), 2.52-2.38 (m, 1H), 2.24 (s, 3H), 2.21-2.11 (m, 1H), 2.04 (s, 6H), 1.79-1.60 (m, 1H) |
| A122 | 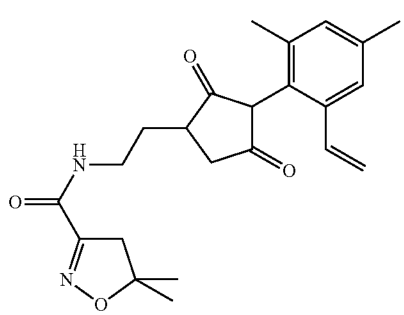 [SMILES: C=Cc1cc(C)cc(C)c1C1C(=O)CC(CCNC(=O)C2=NOC(C)(C)C2)C1=O] | 1HNMR (400 MHz, CD3OD) 7.26 (d, 1H), 7.02-6.92 (m, 1H), 6.59-6.42 (m, 1H), 5.60 (ddd, 1H), 5.15-5.04 (m, 1H), 3.50-3.37 (m, 2H), 3.01-2.97 (m, 2H), 2.95-2.71 (m, 2H), 2.47 (d, 1H), 2.33-2.26 (m, 3H), 2.21-2.08 (m, 1H), 2.05 (d, 3H), 1.72-1.60 (m, 1H), 1.46-1.39 (m, 6H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Chemical Structure | NMR |
|---|---|---|
| A123 | 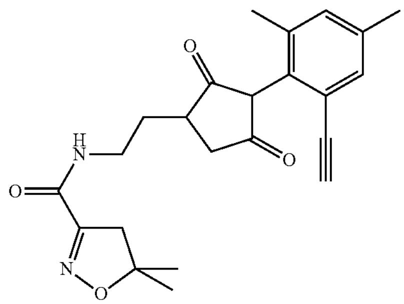 [SMILES: C#Cc1cc(C)cc(C)c1C1C(=O)CC(CCNC(=O)C2=NOC(C)(C)C2)C1=O] | 1HNMR (400 MHz, CD3OD) 7.38 (s, 1H), 7.25 (s, 1H), 3.57-3.38 (m, 2H), 3.04-2.94 (m, 2H), 2.97-2.82 (m, 1H), 2.79-2.66 (m, 1H), 2.47 (s, 1H), 2.43 (br.s., 1H), 2.38 (s, 3H), 2.15 (s, 3H), 2.14-2.05 (m, 1H), 1.81-1.60 (m, 1H), 1.42 (d, 6H) |
| A124 | 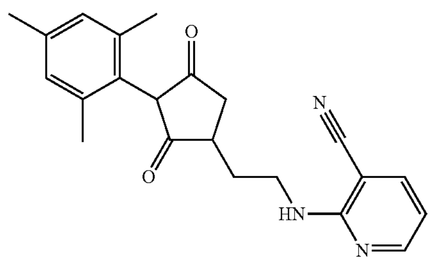 [SMILES: Cc1cc(C)c(C2C(=O)CC(CCNc3ncccc3C#N)C2=O)c(C)c1] | 1HNMR (400 MHz, CD3OD) 8.25 (dd, 1H), 7.78 (dd, 1H), 6.86 (s, 2H), 6.64 (dd, 1H), 3.64 (t, 2H), 2.96-2.86 (m, 1H), 2.79 (br.s., 1H), 2.48 (d, 1H), 2.24 (s, 3H), 2.22-2.14 (m, 1H), 2.05 (s, 6H), 1.80-1.64 (m, 1H) |
| A125 | 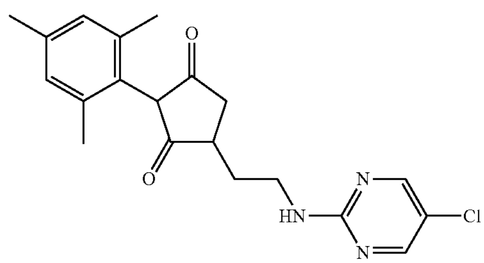 [SMILES: Cc1cc(C)c(C2C(=O)CC(CCNc3ncc(Cl)cn3)C2=O)c(C)c1] | 1HNMR (400 MHz, CD3OD) 8.26 (s, 2H), 6.88 (s, 2H), 3.59-3.49 (m, 2H), 2.97-2.88 (m, 1H), 2.85-2.74 (m, 1H), 2.49 (dd, 1H), 2.27 (s, 3H), 2.23-2.14 (m, 1H), 2.06 (d, 6H), 1.77-1.64 (m, 1H) |
| A126 | 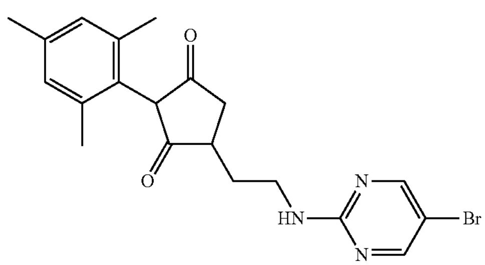 [SMILES: Cc1cc(C)c(C2C(=O)CC(CCNc3ncc(Br)cn3)C2=O)c(C)c1] | 1H NMR (400 MHz, CD3OD) δ = 8.30 (s, 2H), 6.92-6.74 (m, 2H), 3.56-3.43 (m, 2H), 2.95-2.85 (m, 1H), 2.79 (br. s., 1H), 2.46 (dd, J = 2.0, 17.7 Hz, 1H), 2.24 (s, 3H), 2.22-2.10 (m, 1H), 2.04 (d, J = 2.3 Hz, 6H), 1.76-1.63 (m, 1H) |

BIOLOGICAL EXAMPLES

Biological Example 1

Test-Glasshouse Assay for Herbicidal Activity

Seeds of a variety of monocotyledonous and dicotyledonous test plants are sown in standard soil in pots. The plants are cultivated for one day (for pre-emergence) or for about 12 days (for post-emergence) under controlled conditions in a glasshouse (warm climate species at 24/18° C., cool climate species at 20/16° C., both at day/night; 16 hours light; 65% humidity).

The test plants are then grown on, in a glasshouse (greenhouse) under controlled conditions (warm climate species at 24/18° C., cool climate species at 20/16° C., both at day/night; 16 hours light; 65% humidity) and are watered twice daily. 15 days after application of the test herbicide (15DAA) (for post-emergence), and 20 days after application of the test herbicide (20DAA) (for pre-emergence), the test plants are evaluated visually, and an assessed percentage phytotoxicity score is given for each herbicidal application on each plant species (with 100%=total damage to plant; 0%=no damage to plant).

The plant species tested are as follows: *Alopecurus myosuroides* (ALOMY), *Avena fatua* (AVEFA), *Lolium perenne* (LOLPE), *Echinochloa crus-galli* (ECHCG).

TABLE 1

Pre-/Post- emergence herbicidal activity (percentage phytotoxicity).

| Compound | Rate g/ha | LOLPE PRE | LOLPE POST | ALOMY PRE | ALOMY POST | ECHCG PRE | ECHCG POST | AVEFA PRE | AVEFA POST |
|---|---|---|---|---|---|---|---|---|---|
| A1 | 250 | 100 | 90 | 80 | 90 | 100 | 80 | 60 | 90 |
| A2 | 250 | 80 | 100 | 70 | 80 | 90 | 100 | 80 | 100 |
| A3 | 250 | 90 | 100 | 100 | 100 | 100 | 100 | 80 | 90 |
| A4 | 250 | 80 | 100 | 80 | 90 | 60 | 90 | 70 | 100 |
| A5 | 250 | 90 | 90 | 100 | 80 | 90 | 100 | 80 | 90 |
| A6 | 250 | 80 | 90 | 30 | 70 | 90 | 100 | 0 | 90 |
| A7 | 250 | 0 | 70 | 0 | 10 | 0 | 90 | 0 | 90 |
| A8 | 250 | 90 | 90 | 70 | 80 | 90 | 80 | 90 | 90 |
| A9 | 250 | 80 | 90 | 60 | 30 | 80 | 80 | 60 | 80 |
| A10 | 250 | 0 | 90 | 0 | 80 | 0 | 90 | 0 | 80 |
| A11 | 250 | 100 | 100 | 100 | 90 | 100 | 90 | 90 | 90 |
| A12 | 250 | 90 | 90 | 90 | 90 | 100 | 90 | 90 | 90 |
| A13 | 250 | 50 | 70 | 70 | 90 | 90 | 100 | 40 | 100 |
| A14 | 250 | 100 | 100 | 90 | 80 | 100 | 100 | 90 | 90 |
| A15 | 250 | 70 | 70 | 70 | 60 | 70 | 30 | 50 | 50 |
| A16 | 250 | 90 | 90 | 80 | 90 | 100 | 80 | 70 | 100 |
| A17 | 250 | 30 | 40 | 40 | 70 | 10 | 70 | 0 | 70 |
| A18 | 250 | 70 | 80 | 60 | 80 | 60 | 90 | 50 | 80 |
| A19 | 250 | 80 | 100 | 70 | 90 | 80 | 100 | 90 | 100 |
| A20 | 250 | 80 | 90 | 20 | 80 | 100 | 100 | 80 | 100 |
| A21 | 250 | 80 | 90 | 90 | 90 | 100 | 100 | 90 | 100 |
| A22 | 250 | 100 | 90 | 70 | 80 | 100 | 100 | 100 | 100 |
| A23 | 250 | 100 | 90 | 100 | 90 | 100 | 100 | 100 | 100 |
| A24 | 250 | 80 | 90 | 10 | 60 | 90 | 100 | 70 | 100 |
| A25 | 250 | 30 | 20 | 30 | 70 | 50 | 90 | 0 | 80 |
| A26 | 250 | 0 | 40 | 0 | 10 | 0 | 10 | 0 | 0 |
| A27 | 250 | 90 | 100 | 60 | 90 | 90 | 100 | 90 | 90 |
| A28 | 250 | 70 | 80 | 70 | 90 | 90 | 90 | 70 | 100 |
| A29 | 250 | 100 | 100 | 90 | 100 | 90 | 100 | 100 | 100 |
| A30 | 250 | 90 | 80 | 80 | 90 | 60 | 90 | 80 | 80 |
| A31 | 250 | 100 | 90 | 80 | 90 | 90 | 70 | 70 | 90 |
| A32 | 250 | 60 | 60 | 70 | 80 | 80 | 100 | 50 | 100 |
| A33 | 250 | 0 | 30 | 60 | 40 | 70 | 80 | 40 | 40 |
| A34 | 250 | 100 | 90 | 90 | 90 | 100 | 100 | 80 | 90 |
| A35 | 250 | 100 | 100 | 70 | 90 | 80 | 100 | 60 | 70 |
| A36 | 250 | 90 | 100 | 60 | 90 | 90 | 90 | 90 | 100 |
| A37 | 250 | 0 | 0 | 0 | 0 | 0 | 30 | 0 | 0 |
| A38 | 250 | 70 | 80 | 70 | 70 | 100 | 100 | 70 | 80 |
| A39 | 250 | 90 | 100 | 80 | 80 | 30 | 50 | 50 | 80 |
| A40 | 250 | 100 | 90 | 90 | 100 | 100 | 100 | 100 | 100 |
| A41 | 250 | 0 | 40 | 0 | 60 | 0 | 60 | 0 | 20 |
| A42 | 250 | 0 | 10 | 0 | 0 | 0 | 70 | 0 | 0 |
| A43 | 250 | 90 | 100 | 90 | 90 | 90 | 100 | 90 | 100 |
| A44 | 250 | 10 | 0 | 0 | 0 | 0 | 70 | 0 | 0 |
| A45 | 250 | 90 | 80 | 0 | 20 | 80 | 40 | 0 | 0 |
| A46 | 250 | 70 | 100 | 30 | 70 | 60 | 100 | 30 | 90 |
| A47 | 250 | 50 | 30 | 60 | 60 | 80 | 60 | 0 | 70 |
| A48 | 250 | 100 | 100 | 100 | 90 | 90 | 100 | 90 | 100 |
| A49 | 250 | 90 | 100 | 90 | 100 | 100 | 100 | 80 | 100 |
| A50 | 250 | 90 | 100 | 100 | 100 | 90 | 80 | 80 | 90 |
| A51 | 250 | 60 | 90 | 70 | 90 | 90 | 90 | 30 | 80 |
| A52 | 250 | 80 | 90 | 80 | 90 | 100 | 90 | 70 | 80 |
| A53 | 250 | 90 | 100 | 80 | 90 | 100 | 100 | 70 | 100 |
| A54 | 250 | 80 | 100 | 60 | 100 | 80 | 100 | 60 | 100 |
| A55 | 250 | 70 | 90 | 60 | 70 | 80 | 80 | 10 | 0 |
| A56 | 250 | 80 | 90 | 70 | 80 | 60 | 80 | 40 | 80 |
| A57 | 250 | 70 | 100 | 80 | 90 | 100 | 80 | 0 | 50 |
| A58 | 250 | 0 | 90 | 0 | 40 | 0 | 80 | 0 | 10 |
| A59 | 250 | 80 | 100 | 70 | 90 | 100 | 90 | 30 | 90 |
| A60 | 250 | 80 | 90 | 70 | 100 | 70 | 80 | 80 | 100 |
| A61 | 250 | 40 | 70 | 20 | 40 | 30 | 70 | 30 | 0 |
| A62 | 250 | 40 | 80 | 70 | 90 | 80 | 80 | 30 | 80 |
| A63 | 250 | 80 | 90 | 90 | 100 | 70 | 80 | 40 | 90 |
| A64 | 250 | 80 | 100 | 100 | 90 | 80 | 90 | 80 | 90 |

TABLE 1-continued

Pre-/Post- emergence herbicidal activity (percentage phytotoxicity).

| Compound | Rate g/ha | LOLPE PRE | LOLPE POST | ALOMY PRE | ALOMY POST | ECHCG PRE | ECHCG POST | AVEFA PRE | AVEFA POST |
|---|---|---|---|---|---|---|---|---|---|
| A65 | 250 | 80 | 100 | 80 | 100 | 70 | 80 | 70 | 90 |
| A66 | 250 | 40 | 80 | 20 | 70 | 10 | 60 | 0 | 30 |
| A67 | 250 | 20 | NT | 0 | NT | 30 | NT | 0 | NT |
| A68 | 250 | 30 | 80 | 0 | 50 | 10 | 70 | 10 | 0 |
| A69 | 250 | 80 | 100 | 80 | 100 | 70 | 70 | 80 | 90 |
| A70 | 250 | 60 | 100 | 50 | 20 | 100 | 90 | 40 | 90 |
| A71 | 250 | 40 | 80 | 30 | 20 | 0 | 80 | 20 | 50 |
| A72 | 250 | 10 | 80 | 20 | 30 | 0 | 80 | 20 | 90 |
| A73 | 250 | 70 | 60 | 70 | 40 | 30 | 30 | 0 | 60 |
| A74 | 250 | 70 | 60 | 70 | 50 | 70 | 60 | 90 | NC |
| A75 | 250 | 80 | 70 | 70 | 60 | 70 | 30 | 60 | 80 |
| A76 | 250 | 70 | 60 | 30 | 20 | 40 | 40 | 0 | 20 |
| A77 | 250 | 80 | 80 | 100 | 80 | 70 | 70 | 70 | 80 |
| A78 | 250 | 70 | 60 | 60 | 40 | 20 | 30 | 0 | 80 |
| A79 | 250 | 70 | 60 | 30 | 30 | 50 | 40 | 10 | 60 |
| A80 | 250 | 60 | 60 | 10 | 10 | 40 | 0 | 0 | 0 |
| A81 | 250 | 70 | 60 | 60 | 60 | 70 | 60 | 70 | 70 |
| A82 | 250 | 70 | 50 | 70 | 40 | 30 | 20 | 0 | 30 |
| A83 | 250 | 90 | 70 | 90 | 80 | 70 | 70 | 80 | 80 |
| A84 | 250 | 50 | 70 | 50 | 30 | 30 | 50 | 10 | 80 |
| A85 | 250 | 80 | 50 | 70 | 60 | 70 | 40 | 80 | 80 |
| A86 | 250 | 60 | 30 | 20 | 50 | 60 | 30 | 20 | 0 |
| A87 | 250 | 70 | 0 | 0 | 0 | 30 | 0 | 0 | 50 |
| A88 | 250 | 40 | 60 | 0 | 0 | 40 | 0 | 0 | 0 |
| A89 | 250 | 40 | 0 | 0 | 0 | 30 | 0 | 0 | 40 |
| A90 | 250 | 70 | 20 | 0 | 20 | 40 | 60 | 0 | 60 |
| A91 | 250 | 70 | 70 | 60 | 80 | 70 | 0 | 60 | 10 |
| A92 | 250 | 70 | 100 | 70 | 90 | 80 | 100 | 30 | 100 |
| A93 | 250 | 90 | 70 | 90 | 90 | 90 | 100 | 70 | 90 |
| A94 | 250 | 100 | 80 | 80 | 60 | 70 | 90 | 60 | 90 |
| A95 | 250 | 70 | 60 | 80 | 70 | 70 | 70 | 20 | 70 |
| A96 | 250 | 100 | 100 | 80 | 90 | 100 | 100 | 90 | 100 |
| A97 | 250 | 100 | 90 | 80 | 90 | 90 | 100 | 90 | 90 |
| A98 | 250 | 90 | 90 | 40 | 90 | 90 | 100 | 70 | 100 |
| A99 | 250 | 0 | 60 | 0 | 70 | 0 | 100 | 0 | 90 |
| A100 | 250 | 70 | 100 | 60 | 90 | 90 | 100 | 50 | 100 |
| A101 | 250 | 30 | 40 | 40 | 70 | 10 | 70 | 0 | 70 |
| A102 | 250 | 100 | 100 | 100 | 100 | 100 | 100 | 90 | 100 |
| A103 | 250 | 80 | 70 | 80 | 80 | 60 | 70 | 50 | 80 |
| A104 | 250 | 80 | 90 | 60 | 90 | 90 | 70 | 70 | 80 |
| A105 | 250 | 20 | 80 | 20 | 90 | 10 | 90 | 20 | 80 |
| A106 | 250 | 60 | 90 | 70 | 90 | 90 | 90 | 40 | 90 |
| A107 | 250 | 100 | 100 | 90 | 100 | 100 | 100 | 90 | 100 |
| A108 | 250 | 100 | 100 | 100 | 100 | 100 | 100 | 90 | 100 |
| A109 | 250 | 90 | 100 | 90 | 100 | 90 | 100 | 90 | 100 |
| A110 | 250 | 90 | 90 | 100 | 100 | 90 | 100 | 90 | 100 |
| A111 | 250 | 90 | 40 | 100 | 100 | 90 | 100 | 100 | 100 |
| A112 | 250 | 90 | 100 | 100 | 100 | 100 | 100 | 90 | 100 |
| A113 | 250 | 90 | 100 | 90 | 100 | 90 | 100 | 70 | 100 |
| A114 | 250 | 70 | 100 | 90 | 90 | 70 | 100 | 80 | 100 |
| A115 | 250 | 90 | 90 | 100 | 100 | 70 | 100 | 80 | 100 |
| A116 | 250 | 90 | 100 | 90 | 100 | 90 | 100 | 90 | 100 |
| A117 | 250 | 80 | 100 | 90 | 100 | 80 | 100 | 80 | 100 |
| A118 | 250 | 90 | 100 | 100 | 100 | 90 | 100 | 90 | 100 |
| A119 | 250 | 80 | 100 | 90 | 90 | 90 | 100 | 80 | 100 |
| A120 | 250 | 90 | 90 | 90 | 90 | 90 | 100 | 90 | 100 |
| A121 | 250 | 100 | 90 | 100 | 100 | 100 | 100 | 100 | 100 |
| A122 | 250 | 0 | 80 | 0 | 90 | 0 | 90 | 0 | 90 |
| A123 | 250 | 90 | 80 | 70 | 100 | 20 | 100 | 50 | 100 |
| A124 | 250 | 80 | 80 | 60 | 80 | 90 | 100 | 40 | 60 |
| A125 | 250 | 90 | 100 | 90 | 90 | 90 | 100 | 80 | 90 |
| A126 | 250 | 90 | 90 | 80 | 90 | 80 | 90 | 100 | 90 |

NT = not tested.

TABLE 2

Post-emergence herbicidal activity against cereal crops (wheat) +/− safener (cloquintocet-mexyl (CQC) applied at 50 g/ha) - Results (percentage phytotoxicity)
Post-emergence Crop Selectivity

| Compound | Rate (g/ha) | Wheat − CQC | +CQC |
|---|---|---|---|
| A1 | 250 | 80 | 20 |
| A2 | 250 | 80 | 80 |
| A3 | 250 | 90 | 60 |
| A4 | 250 | 90 | 50 |
| A5 | 250 | 50 | 20 |
| A6 | 250 | 10 | 10 |
| A7 | 250 | 20 | 0 |
| A8 | 250 | 70 | 10 |
| A9 | 250 | 40 | 10 |
| A10 | 250 | 70 | 20 |
| A11 | 250 | 80 | 70 |
| A12 | 250 | 90 | 80 |
| A13 | 250 | 70 | 40 |
| A14 | 250 | 60 | 30 |
| A15 | 250 | 40 | 30 |
| A16 | 250 | 80 | 50 |
| A17 | 250 | 50 | 10 |
| A18 | 250 | 60 | 0 |
| A19 | 250 | 80 | 80 |
| A20 | 250 | 80 | 0 |
| A21 | 250 | 90 | 70 |
| A22 | 250 | 80 | 30 |
| A23 | 250 | 90 | 80 |
| A24 | 250 | 80 | 70 |
| A25 | 250 | 60 | 0 |
| A26 | 250 | 0 | 10 |
| A27 | 250 | 80 | 70 |
| A28 | 250 | 80 | 20 |
| A29 | 250 | 90 | 70 |
| A30 | 250 | 70 | 40 |
| A31 | 250 | 70 | 10 |
| A32 | 250 | 60 | 10 |
| A33 | 250 | 40 | 10 |
| A34 | 250 | 80 | 70 |
| A35 | 250 | 80 | 60 |
| A36 | 250 | 80 | 10 |
| A37 | 250 | 20 | 10 |
| A38 | 250 | 70 | 30 |
| A39 | 250 | 60 | 10 |
| A40 | 250 | 90 | 80 |
| A41 | 250 | 60 | 20 |
| A42 | 250 | 0 | 10 |
| A43 | 250 | 90 | 50 |
| A44 | 250 | 30 | 10 |
| A45 | 250 | 0 | 0 |
| A46 | 250 | 80 | 70 |
| A47 | 250 | 50 | 0 |
| A48 | 250 | 60 | 50 |
| A49 | 250 | 90 | 90 |
| A50 | 250 | 90 | 90 |
| A51 | 250 | 80 | 80 |
| A52 | 250 | 80 | 30 |
| A53 | 250 | 90 | 80 |
| A54 | 250 | 90 | 80 |
| A55 | 250 | 30 | 0 |
| A56 | 250 | 80 | 70 |
| A57 | 250 | 80 | 20 |
| A58 | 250 | 80 | 20 |
| A59 | 250 | 90 | 80 |
| A60 | 250 | 80 | 70 |
| A61 | 250 | 70 | 40 |
| A62 | 250 | 80 | 70 |
| A63 | 250 | 80 | 80 |
| A64 | 250 | 90 | 80 |
| A65 | 250 | 80 | 40 |
| A66 | 250 | 80 | 40 |
| A67 | 250 | 0 | 0 |
| A68 | 250 | 90 | 0 |
| A69 | 250 | 90 | 80 |
| A70 | 250 | 80 | 80 |
| A71 | 250 | 80 | 20 |
| A72 | 250 | 80 | 70 |
| A73 | 250 | 0 | 10 |
| A74 | 250 | 10 | 0 |
| A75 | 250 | 0 | 0 |
| A76 | 250 | 0 | 0 |
| A77 | 250 | 80 | 10 |
| A78 | 250 | 0 | 0 |
| A79 | 250 | 30 | 0 |
| A80 | 250 | 0 | 0 |
| A81 | 250 | 0 | 0 |
| A82 | 250 | 0 | 0 |
| A83 | 250 | 80 | 10 |
| A84 | 250 | 0 | 0 |
| A85 | 250 | 20 | 10 |
| A86 | 250 | 20 | 0 |
| A87 | 250 | 20 | 0 |
| A88 | 250 | 0 | 0 |
| A89 | 250 | 10 | 0 |
| A90 | 250 | 0 | 20 |
| A91 | 250 | 70 | 70 |

The invention claimed is:

1. A compound of formula (I):

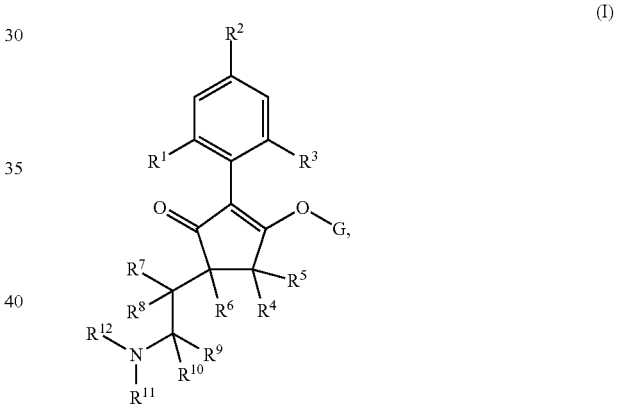

or an agrochemically acceptable salt thereof wherein:

$R^1$ is selected from the group consisting of methyl, ethyl, n-propyl, cyclopropyl, trifluoromethyl, vinyl, ethynyl, fluorine, chlorine, bromine, methoxy, ethoxy and fluoromethoxy;

$R^2$ is selected from the group consisting of hydrogen, methyl, ethyl, n-propyl, isopropyl, cyclopropyl, fluoromethyl, fluoroethyl, vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen, methoxy, prop-2-ynyloxy, and ($C_1$-$C_2$fluoroalkyl)-methoxy-; or $R^2$ is phenyl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro; or $R^2$ is monocyclic heteroaryl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro; and $R^3$ is selected from the group consisting of hydrogen, methyl, ethyl, n-propyl, cyclopropyl, trifluoromethyl, vinyl, ethynyl, fluorine, chlorine, bromine, methoxy, ethoxy, n-propoxy, isopropoxy, $C_1$-$C_2$fluoroalkoxy, $C_1$-$C_2$alkoxy-$C_1$-$C_3$alkoxy- and $C_1$fluoroalkoxy-$C_1$-$C_3$alkoxy-;

$R^4$, $R^5$ and $R^6$ are independently of each other, selected from the group consisting of hydrogen, $C_1$-$C_5$alkyl, $C_2$-$C_3$ alkenyl, $C_2$-$C_3$alkynyl, $C_1$-$C_2$fluoroalkyl and $C_1$-$C_2$alkoxy$C_1$-$C_2$alkyl;

$R^7$ and $R^8$ are independently of each other, selected from the group consisting of hydrogen, fluorine and $C_1$-$C_3$alkyl;

$R^9$ and $R^{19}$ are independently of each other, selected from the group consisting of hydrogen, fluorine and $C_1$-$C_3$alkyl;

$R^{11}$ is —(C=O)-5,5-dimethyl-4H-isoxazol-2-yl, $R^{12}$ is selected from the group consisting of hydrogen, $C_1$-$C_6$alkyl, $C_1$-$C_6$alkoxy and hydroxy;

and wherein:

G is hydrogen; an agriculturally acceptable metal, or an agriculturally acceptable sulfonium or ammonium group; or G is —C($X^a$)—$R^a$, —C($X^b$)—$X^c$—$R^b$, —C($X^d$)—N($R^c$)—$R^d$, —SO$_2$—$R^e$, —P($X^e$)($R^f$)—$R^9$, —CH$_2$—$X^f$—$R^h$, or —CH(Me)-$X^f$—$R^h$; or phenyl-CH$_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-CH$_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—CH$_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—CH$_2$—, $C_1$-$C_6$alkyl-C(O)—CH$_2$—, $C_1$-$C_6$alkoxy-C(O)—CH=CH—, $C_2$-$C_7$alken-1-yl-CH$_2$—, $C_2$-$C_7$alken-1-yl-CH($C_1$-$C_2$alkyl)-, $C_2$-$C_4$fluoroalken-1-yl-CH$_2$—, $C_2$-$C_7$alkyn-1-yl-CH$_2$—, or $C_2$-$C_7$alkyn-1-yl-CH($C_1$-$C_2$alkyl)-;

wherein $X^a$, $X^b$, $X^d$, $X^e$ and $X^f$ are independently of each other oxygen or sulfur; and wherein $R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_3$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; $C_1$-$C_6$alkoxy-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro.

2. The compound according to claim 1, wherein G is hydrogen.

3. The compound according to claim 1, wherein $R^5$, $R^6$, $R^7$, $R^8$, $R^9$ and $R^{10}$ are hydrogen.

4. The compound according to claim 1, wherein $R^2$ is selected from the group consisting of methyl, prop-1-ynyl and an optionally substituted monocyclic heteroaryl selected from the group consisting of $R^{2a}$ and $R^{2b}$:

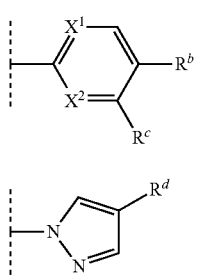

in which:
$X^1$ is N or CH;
$X^2$ is N or $CR^a$;

$R^a$ is selected from the group consisting of hydrogen, fluorine, chlorine and $C_1$fluoroalkyl;

$R^b$ is selected from the group consisting of hydrogen, fluorine, chlorine and $C_1$fluoroalkyl;

$R^b$ is selected from the group consisting of hydrogen, fluorine, chlorine, bromine, methyl, $C_1$fluoroalkyl and cyano; and $R^d$ is selected from the group consisting of hydrogen, fluorine, chlorine, bromine, methyl, $C_1$fluoroalkyl and cyano.

5. The compound according to claim 1, wherein $R^1$ and $R^3$ are methyl.

6. The compound according to claim 1, wherein $R^1$ is methyl, $R^2$ is methyl and $R^3$ is methyl.

7. The compound of claim 1, wherein the compound of formula (I) is a compound of formula (Ia):

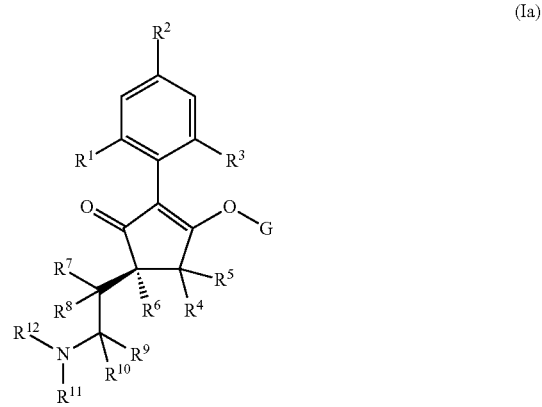

wherein $R^1$, $R^2$, $R^3$, $R^4$, $R^5$, $R^6$, $R^7$, $R^8$, $R^9$, $R^{10}$, $R^{11}$, $R^{12}$ and G are as defined therein.

8. The compound according to claim 7, wherein, more than 50% by molarity of the compound of formula (Ia) has the indicated stereochemistry at the ring-carbon atom bonded to $R^6$ and —$CR^7R^8$—$CR^9R^{10}$—$NR^{11}R^{12}$.

9. A herbicidal composition which comprises a compound of formula (I) as defined in claim 1, and an agrochemically acceptable carrier, diluent and/or solvent.

10. The herbicidal composition according to claim 9, which comprises one or more further herbicides and/or a safener.

11. A method of controlling grassy monocotyledonous weeds in crops of useful plants, comprising applying a herbicidal composition according to claim 9, to the weeds or to the locus thereof.

* * * * *